United States Patent
Truong et al.

(10) Patent No.: US 11,504,518 B2
(45) Date of Patent: Nov. 22, 2022

(54) REUSABLE ASEPTIC FLUID COUPLINGS

(71) Applicant: Colder Products Company, Roseville, MN (US)

(72) Inventors: Loi T. Truong, Savage, MN (US); Randall S. Williams, Minneapolis, MN (US)

(73) Assignee: Colder Products Company, Roseville, MN (US)

(*) Notice: Subject to any disclaimer, the term of this patent is extended or adjusted under 35 U.S.C. 154(b) by 0 days.

(21) Appl. No.: 17/090,178

(22) Filed: Nov. 5, 2020

(65) Prior Publication Data
US 2021/0052881 A1 Feb. 25, 2021

Related U.S. Application Data

(63) Continuation of application No. 16/445,911, filed on Jun. 19, 2019, now Pat. No. 10,828,481, which is a
(Continued)

(51) Int. Cl.
*A61M 39/10* (2006.01)
*A61M 39/16* (2006.01)
(Continued)

(52) U.S. Cl.
CPC ...... *A61M 39/1011* (2013.01); *A61M 39/105* (2013.01); *A61M 39/16* (2013.01);
(Continued)

(58) Field of Classification Search
CPC ............ A61M 39/1011; A61M 39/105; A61M 39/16; A61M 39/18; A61M 39/26;
(Continued)

(56) References Cited

U.S. PATENT DOCUMENTS 2,779,608 A 1/1957 Abbey
4,334,551 A 6/1982 Pfister
(Continued)

FOREIGN PATENT DOCUMENTS

CN 104507529 4/2015
EP 0028601 5/1981
(Continued)

OTHER PUBLICATIONS

European Extended Search Report in European Application No. EP16783779, dated Oct. 31, 2018, 9 pages.
(Continued)

*Primary Examiner* — Angelisa L. Hicks
(74) *Attorney, Agent, or Firm* — Fish & Richardson P.C.

(57) ABSTRACT

Some fluid coupling devices described herein are configured for use in fluid systems for purposes of providing a repeatable, aseptic fluid coupling system. Such repeatable, aseptic fluid coupling systems are configured to facilitate multiple connection and disconnection cycles while repeatably establishing a sterile fluid pathway through the coupling system. The repeatable, aseptic fluid coupling systems can repeatably establish a sterile fluid pathway through the coupling system even though the coupling system may be used in a non-sterile environment.

20 Claims, 35 Drawing Sheets

Related U.S. Application Data continuation of application No. 15/288,162, filed on Oct. 7, 2016, now Pat. No. 10,369,348.

(60) Provisional application No. 62/238,870, filed on Oct. 8, 2015.

(51) Int. Cl.
*A61M 39/18* (2006.01)
*A61M 39/26* (2006.01)
*F16L 37/35* (2006.01)

(52) U.S. Cl.
CPC ............ *A61M 39/18* (2013.01); *A61M 39/26* (2013.01); *F16L 37/35* (2013.01); *A61M 2039/1027* (2013.01); *A61M 2039/263* (2013.01); *F16L 2201/44* (2013.01)

(58) Field of Classification Search
CPC ..... A61M 2039/1027; A61M 2039/263; F16L 37/35; F16L 2201/44
See application file for complete search history.

(56) References Cited

U.S. PATENT DOCUMENTS

| | | | |
|---|---|---|---|
| 4,429,713 A | 2/1984 | Walter | |
| 4,664,148 A | 5/1987 | Magnuson | |
| 4,804,015 A | 2/1989 | Albinsson | |
| 5,806,564 A | 9/1998 | Wilcox | |
| 5,971,019 A | 10/1999 | Imal | |
| 6,161,578 A | 12/2000 | Braun et al. | |
| 6,237,631 B1 | 5/2001 | Giesler et al. | |
| 6,428,520 B1* | 8/2002 | Lopez | A61M 39/045 604/249 |
| 7,469,472 B2 | 12/2008 | deCler et al. | |
| 7,547,047 B2 | 6/2009 | deCler et al. | |
| 7,959,192 B2 | 6/2011 | Elton et al. | |
| 8,628,501 B2 | 1/2014 | Hadden | |
| 8,690,120 B2 | 4/2014 | Hartnett et al. | |
| 9,016,334 B2 | 4/2015 | Deo | |
| 10,022,532 B2 | 7/2018 | Burdge | |
| 2006/0035494 A1 | 2/2006 | Sugaya et al. | |
| 2007/0073215 A1 | 3/2007 | Wieslander | |
| 2008/0164296 A1 | 7/2008 | Shelton et al. | |
| 2008/0185056 A1 | 8/2008 | Diodati et al. | |
| 2009/0051161 A1 | 2/2009 | Eskstrom | |
| 2009/0076434 A1 | 3/2009 | Mischelevich | |
| 2010/0230950 A1 | 9/2010 | Scott et al. | |
| 2011/0071465 A1 | 3/2011 | Wang et al. | |
| 2011/0240158 A1 | 10/2011 | Py | |
| 2012/0031515 A1 | 2/2012 | Whitaker | |
| 2012/0220955 A1* | 8/2012 | Maseda | A61M 39/20 604/256 |
| 2013/0341904 A1 | 12/2013 | Lehmann et al. | |
| 2014/0345748 A1 | 11/2014 | Rogers et al. | |
| 2016/0022979 A1 | 1/2016 | Vigna | |
| 2016/0082245 A1 | 3/2016 | Gebauer et al. | |
| 2016/0158519 A1 | 6/2016 | Rhinehart | |
| 2018/0296817 A1 | 10/2018 | Burdge et al. | |
| 2021/0346672 A1* | 11/2021 | Grant | A61M 39/162 |

FOREIGN PATENT DOCUMENTS

| | | |
|---|---|---|
| WO | WO 1980/001507 | 7/1980 |
| WO | WO 2008/094707 | 8/2008 |
| WO | WO 2012/114105 | 8/2012 |
| WO | WO 2014/160756 | 10/2014 |
| WO | WO 2016/172229 | 10/2016 |

OTHER PUBLICATIONS

European Extended Search Report in European Application No. EP16854486, dated May 20, 2019, 7 pages.
International Preliminary Report on Patentability in International Application No. PCT/US2016/028467, dated Oct. 24, 2017 9 pages.
International Preliminary Report on Patentability in International Application No. PCT/US2016/056120, dated Apr. 10, 2018, 11 pages.
International Search Report and Written Opinion in International Application No. PCT/US2016/028467, dated Jul. 26, 2016, 9 pages.
International Search Report and Written Opinion in International Application No. PCT/US2016/056120, dated Dec. 13, 2016, 18 pages.

* cited by examiner

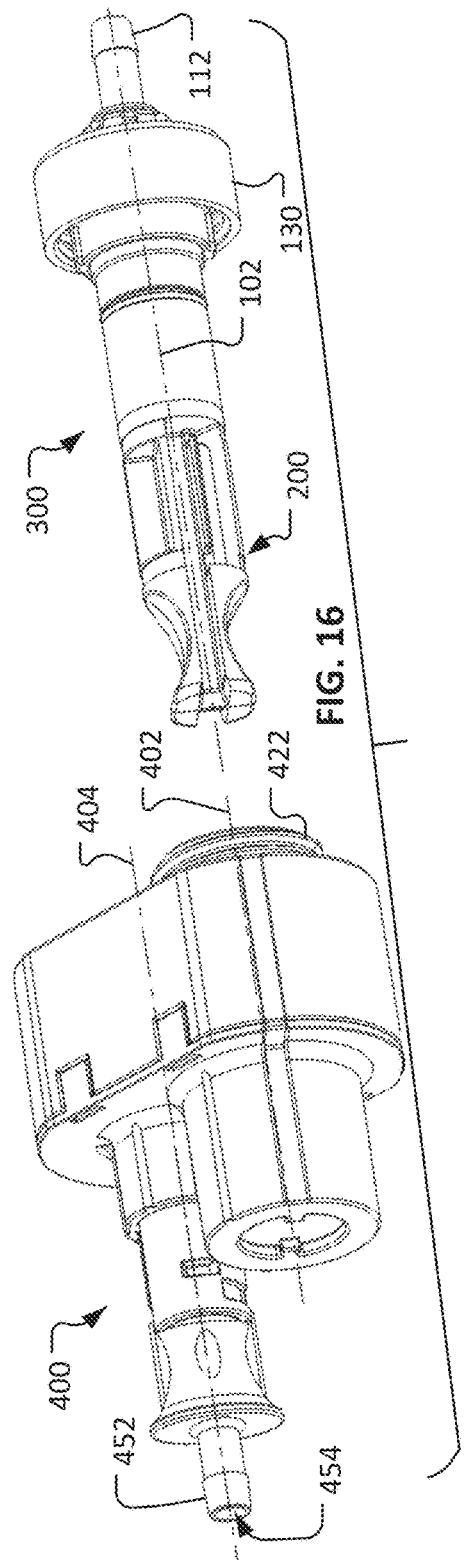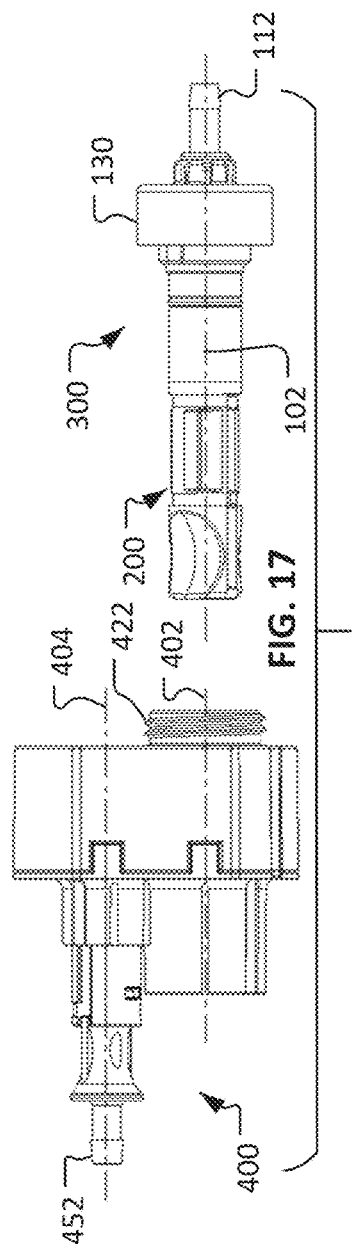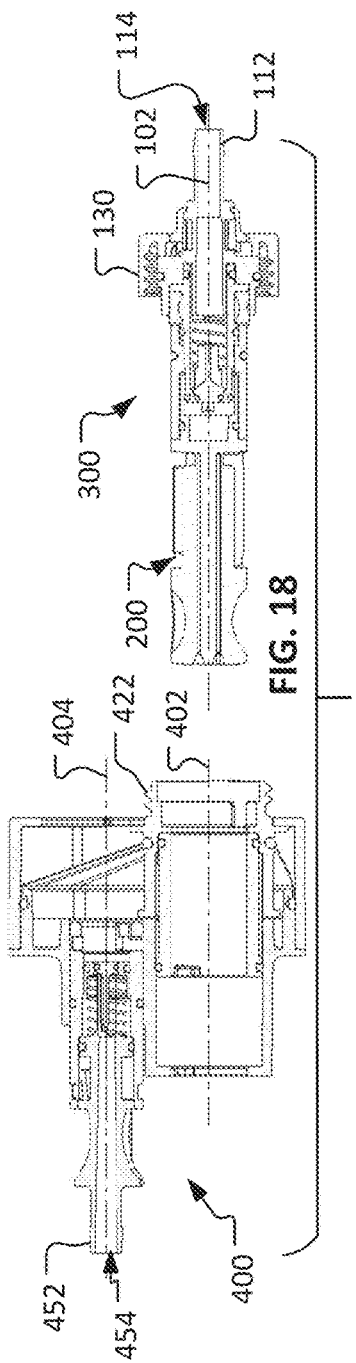

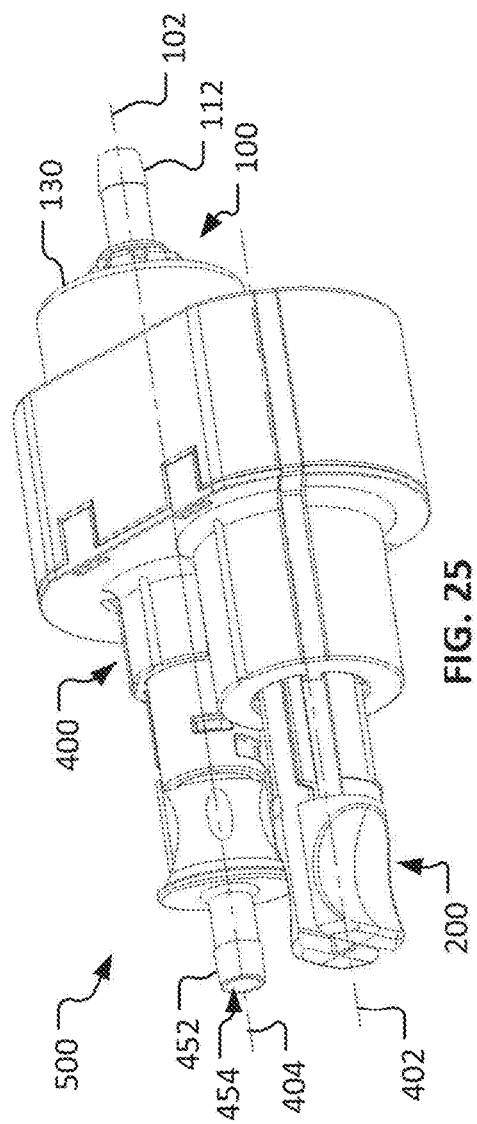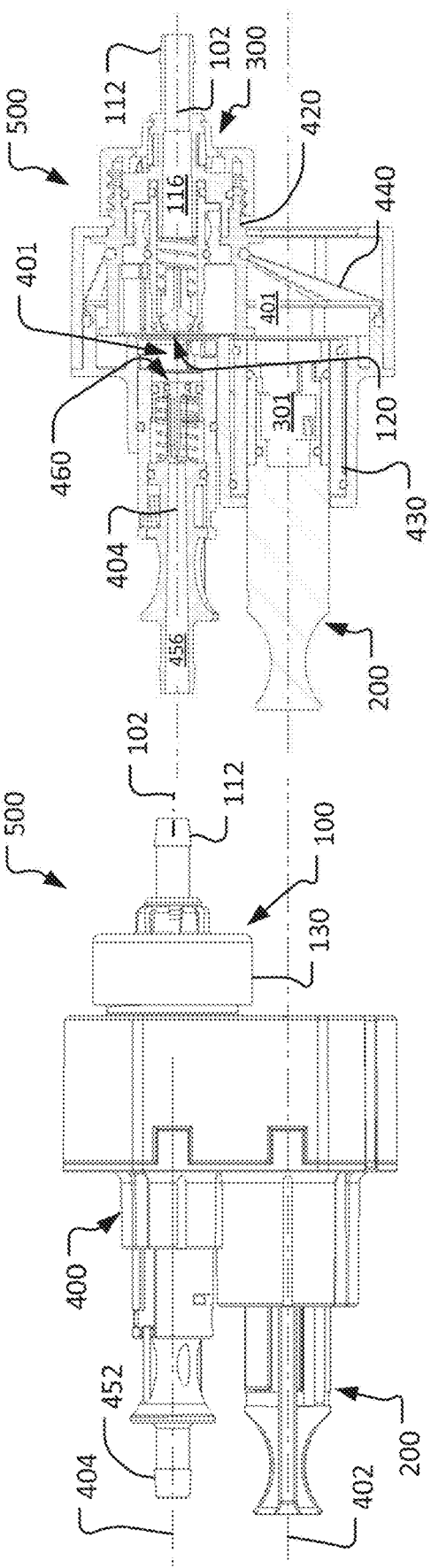
FIG. 25
FIG. 26
FIG. 27

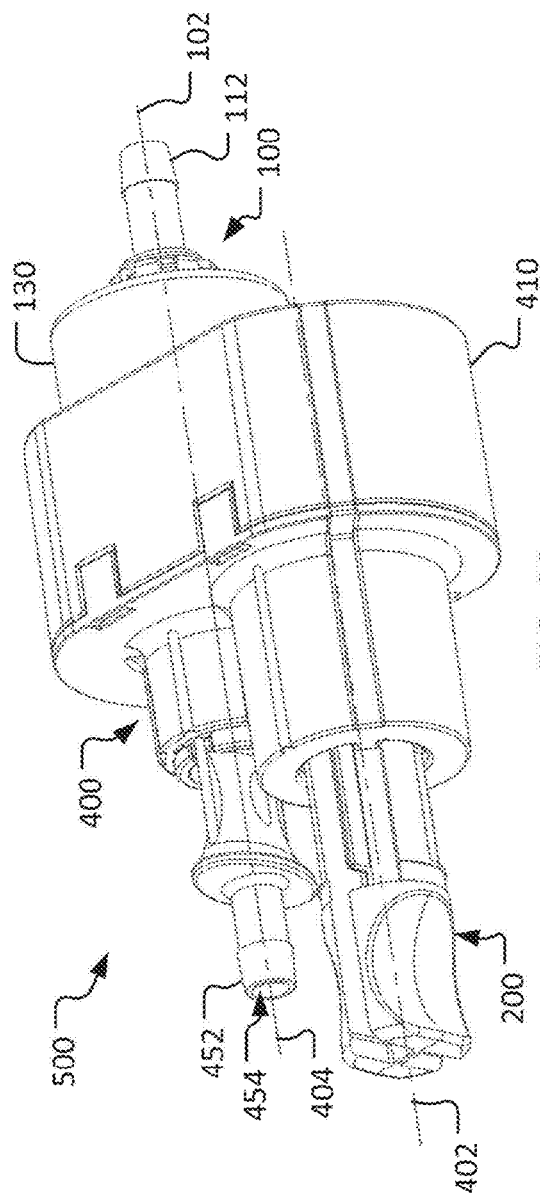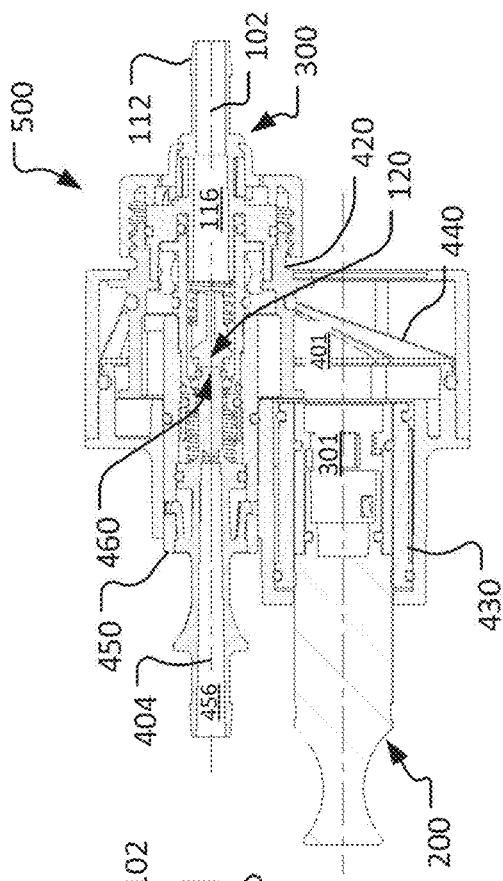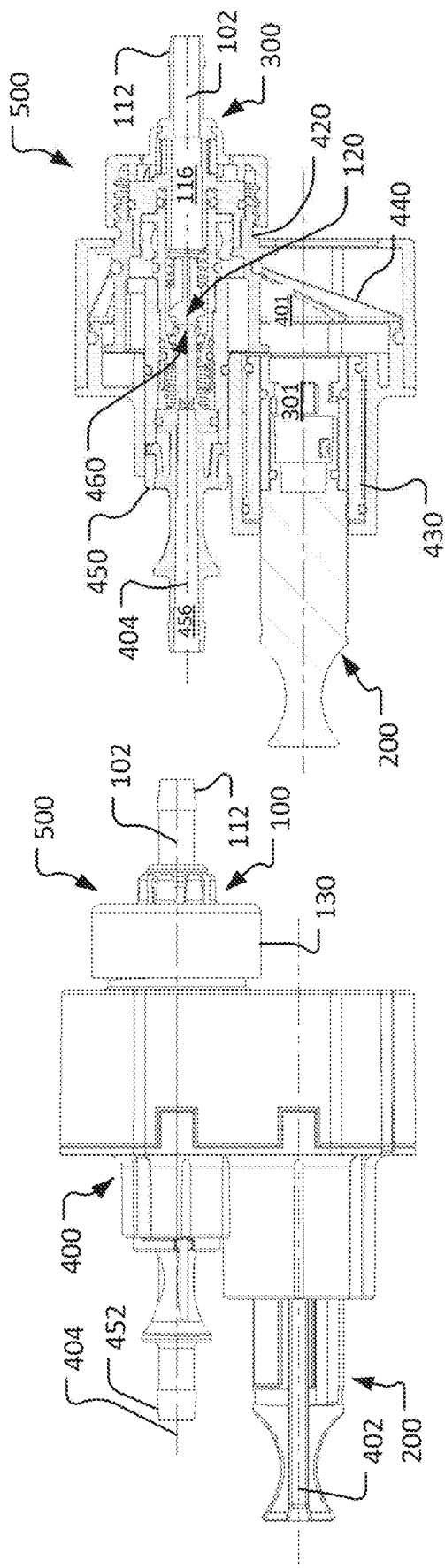
FIG. 28
FIG. 29
FIG. 30

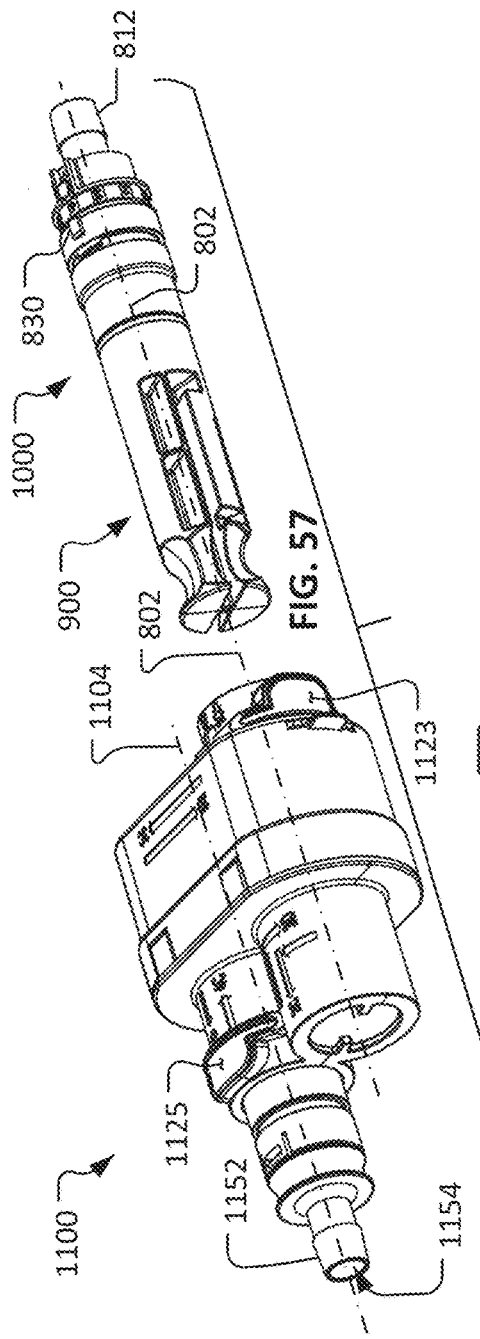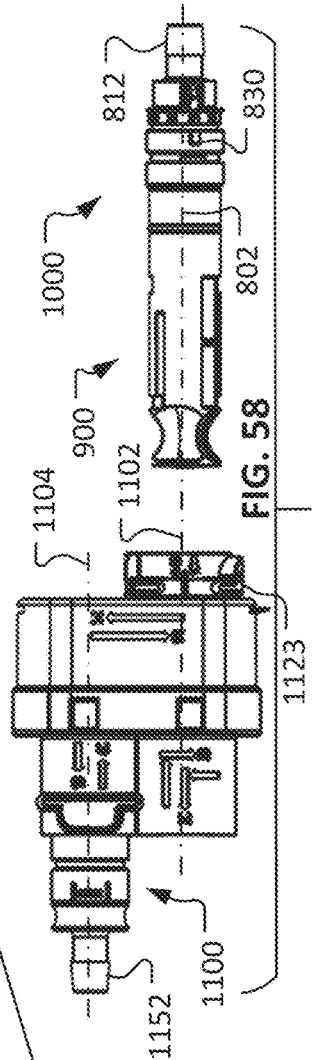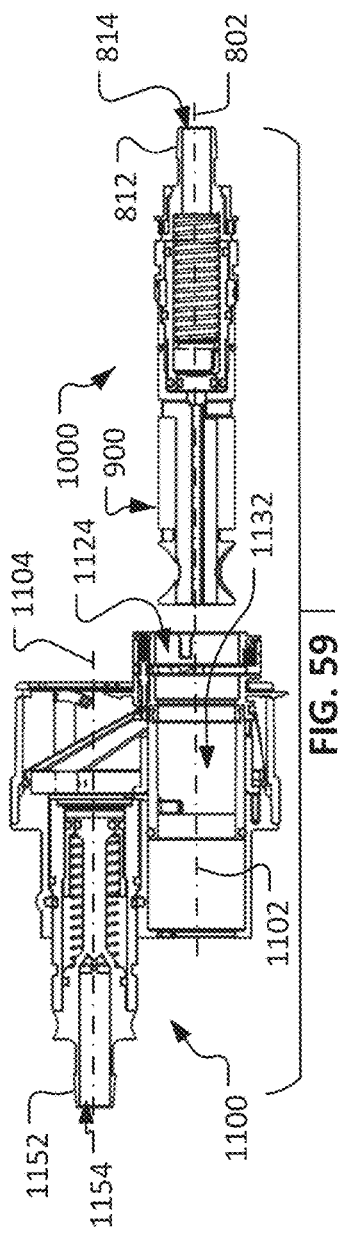

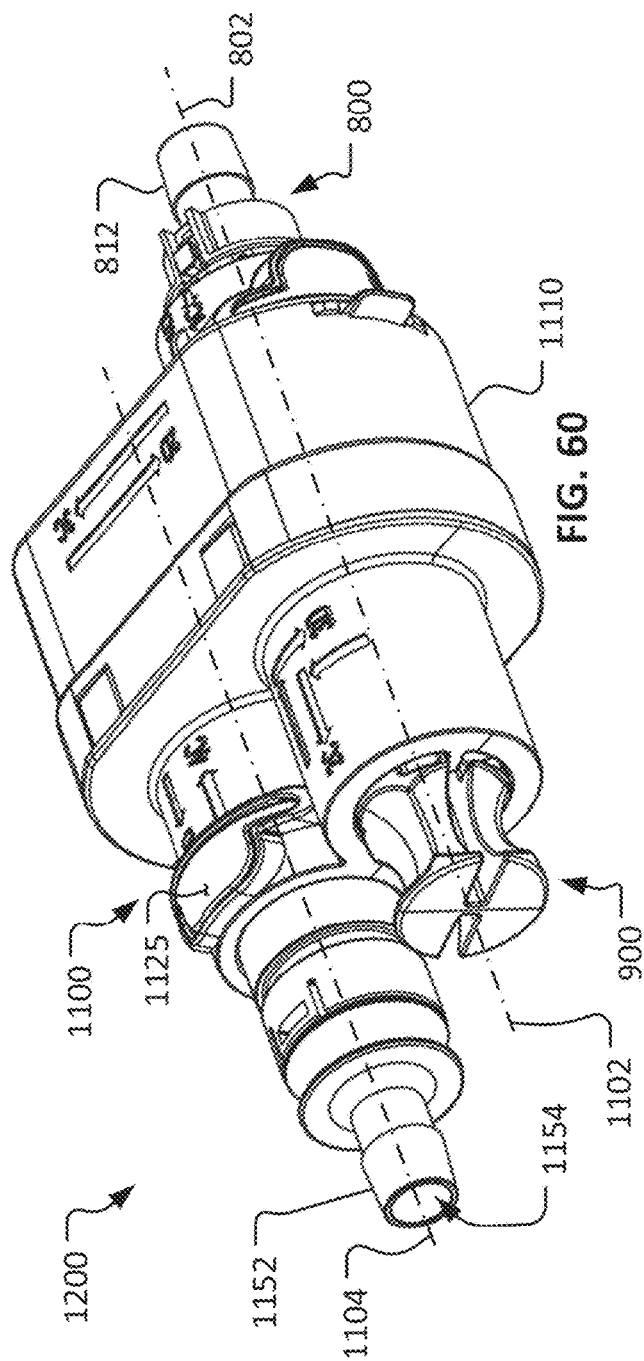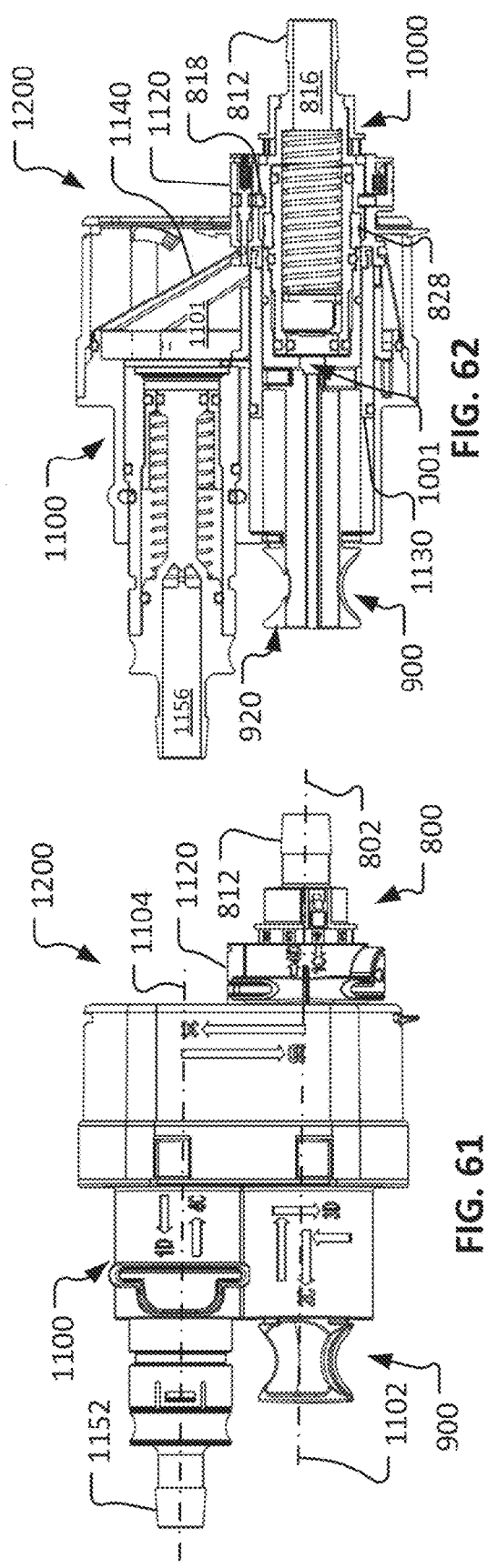

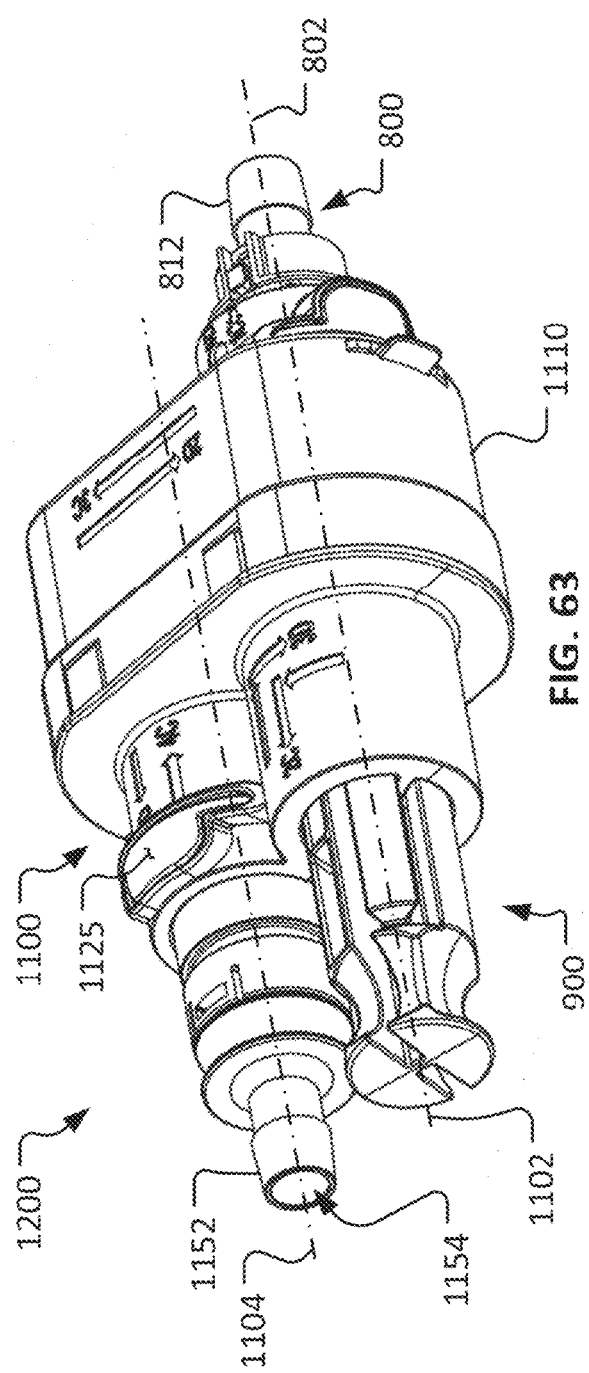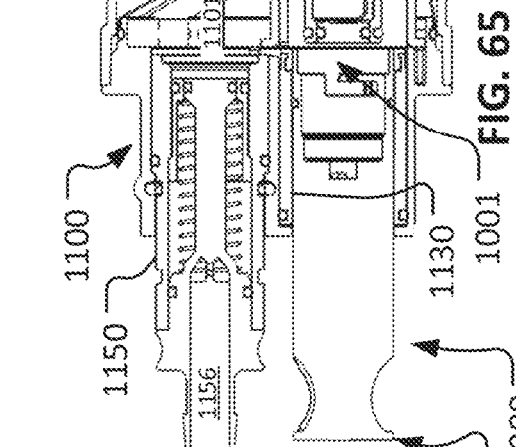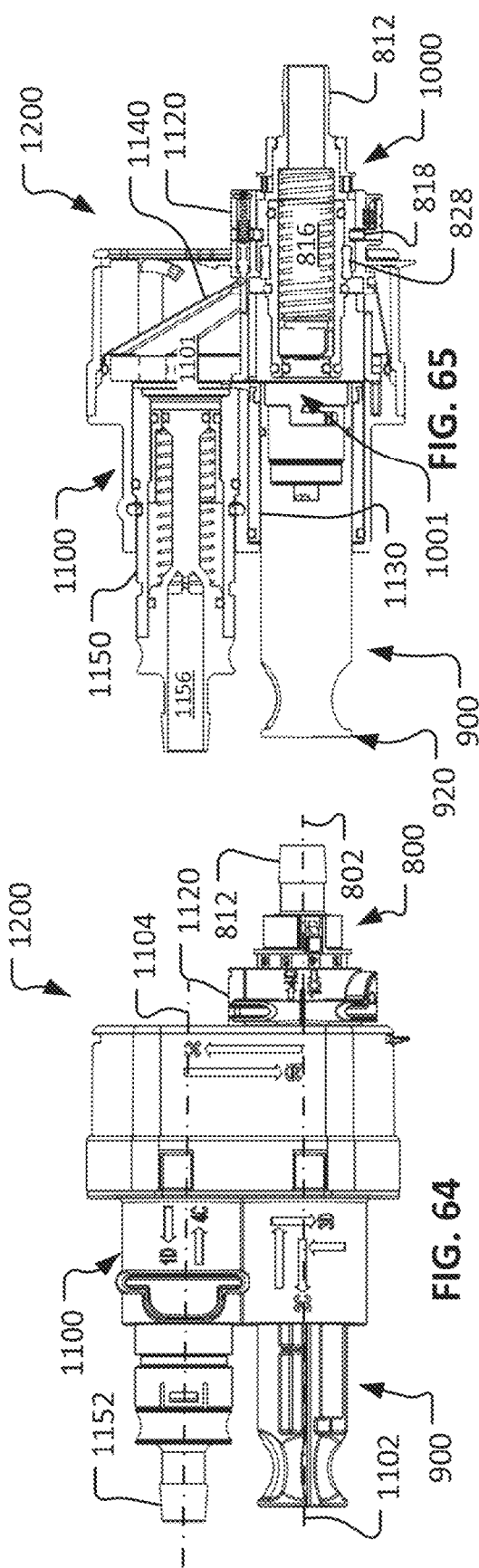

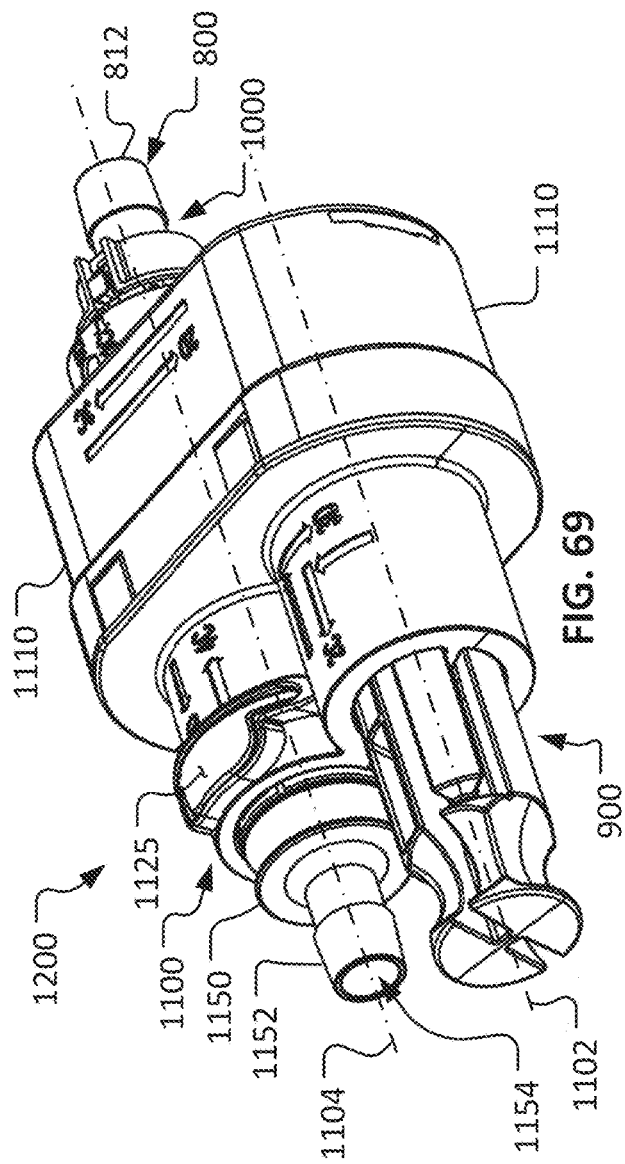
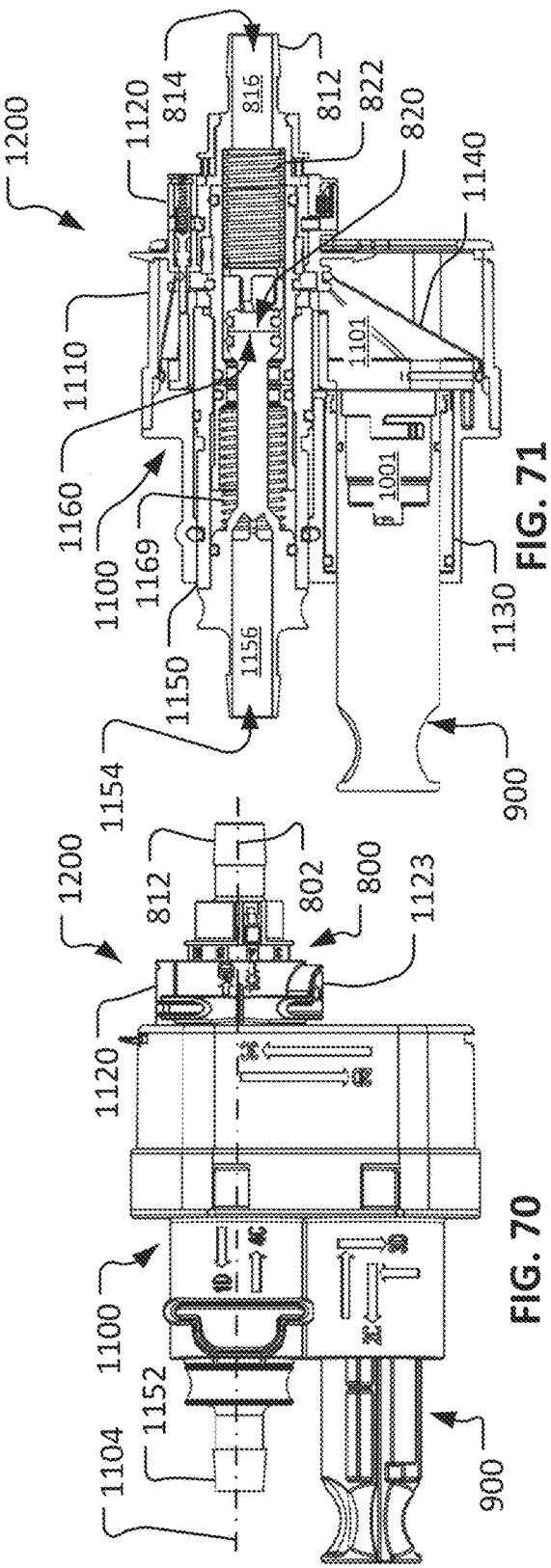

REUSABLE ASEPTIC FLUID COUPLINGS

CROSS-REFERENCE TO RELATED APPLICATIONS

This application is a continuation of U.S. application Ser. No. 16/445,911, filed Jun. 19, 2019, which is a continuation of U.S. application Ser. No. 15/288,162, filed Oct. 7, 2016, now U.S. Pat. No. 10,369,348, which claims the benefit of U.S. Provisional Application Ser. No. 62/238,870, filed Oct. 8, 2015. The disclosures of the prior applications are considered part of (and are incorporated by reference in) the disclosure of this application.

BACKGROUND

1. Technical Field

This document relates to fluid coupling devices for fluid systems and methods. For example, some embodiments described in this document relate to reusable aseptic fluid coupling devices that isolate fluids flowing through the coupling devices from the surrounding environment.

2. Background Information

In the bioprocessing field, manufacturers have been transitioning from fluid handling systems that use fixed, reusable equipment (e.g., made primarily of stainless steel) to single-use fluid handling equipment (e.g., made primarily of plastics). In some cases, the single-use fluid handling equipment is supplied pre-sterilized and is disposed of after use. With this type of equipment, there is a need to make connections and disconnections that maintain sterility during the connection and disconnection actions. The need is particularly acute in the context of lower classification (e.g., less sterile) environments.

There are fluid coupling technologies used in the bioprocessing field that can provide a sterile connection, and there are fluid coupling technologies that can provide a sterile disconnection. In many cases, however, these fluid coupling systems do not repeatably provide both a sterile connection and a sterile disconnection. As a result, in some cases complex single-use tubing assemblies are employed to make multiple sterile connections and disconnections. Such complex assemblies may tend to increase process equipment costs and to reduce processing efficiencies.

SUMMARY

This document describes a number of fluid coupling devices and systems for use in fluid handling systems and methods. In some embodiments, the fluid coupling devices and systems can be implemented as repeatable, aseptic fluid coupling systems. Such repeatable, aseptic fluid coupling systems are configured to facilitate multiple connection and disconnection cycles while maintaining the sterility/isolation of the fluid pathway through the coupling system, even while the fluid coupling systems are used in a non-sterile environment or an environment having other types of contaminants. For example, particular embodiments of these fluid coupling devices can be configured to improve bioprocessing fluid handling equipment because the fluid coupling devices can be repeatably connected and disconnected (e.g., multiple times) in a sterile, aseptic fashion. In the context of this disclosure, the term "fluid" includes both gases and liquids.

The fluid coupling systems provided herein can be further described as being configured to allow fluid transmission through the coupling in a manner that isolates the coupling's fluid flow path from regions outside of the fluid flow path. That is the case whether the coupling's fluid flow path is, at the time of initial use, sterile/aseptic or not. Hence, when a material is transmitted through the fluid flow path of the coupling, the material is protected/isolated from potential contaminants (including, but not limited to, microorganisms) from regions outside of the fluid flow path. In addition, the coupling portions of the fluid coupling systems provided herein can be disconnected and reconnected multiple times while maintaining the isolation of the coupling's fluid flow path (and the isolation of the material within the fluid flow path).

While the fluid coupling systems provided herein are generally referred to as sterile/aseptic fluid coupling systems, it should be understood that the fluid coupling systems can be used in a sterilized status and/or in a nonsterile status. When the fluid coupling systems are sterilized prior to the initial use, the coupling will maintain the sterility of sterile fluids transmitted through the coupling. In other words, the fluid coupling systems isolate a sterile fluid from a non-sterile environment while transmitting the sterile fluid through the coupling. Or, if a nonsterile fluid is being transmitted through the coupling, the fluid coupling system will isolate the nonsterile fluid from the environment outside of the coupling's fluid flow path. Hence, the fluid coupling systems provided herein are configured to isolate fluid flowing through the coupling from the surrounding environment (including, but not limited to, isolation from microorganisms), and to consistently maintain that isolation even while the coupling is connected and disconnected multiple times.

In one implementation, an aseptic fluid coupling system includes a first coupling portion and a second coupling portion configured to releasably couple with the first coupling portion. The first coupling portion includes a first valve body defining a first longitudinal axis and a first end port, a first valve member disposed within the first valve body, and a cap that is releasably coupleable to the first valve body. The cap encloses at least a portion of the first valve body while the cap is coupled to the first valve body. The second coupling portion includes a housing, a second valve body coupled with the housing (the second valve body defining a second longitudinal axis and a second end port), a second valve member disposed within the second valve body, and a connection member configured to releasably couple with the first coupling portion. The connection member is movably coupled with the housing between a first position and a second position.

Such an aseptic fluid coupling system may optionally include one or more of the following features. The second valve body may be slidably coupled with the housing. The second valve body may be slidable along the second longitudinal axis. The connection member may be slidably coupled with the housing. The connection member may be slidable between the first position and the second position along a path that is transverse to the second longitudinal axis. In some embodiments, while the connection member is in the second position, the connection member may be coaxial with the second longitudinal axis. In some embodiments, while the first coupling portion is coupled to the connection member, the first longitudinal axis is coincident with the second longitudinal axis. In particular embodiments, while the connection member is in the first position and the first coupling portion is coupled to the connection member, the first longitudinal axis may be spaced apart from the second longitudinal axis. The first longitudinal axis may be parallel to the second longitudinal axis. The cap may be releasably coupleable to the first valve body using a bayonet connection. In some embodiments, while the cap is coupled to the first valve body, a first seal exists between the cap and the first valve body, and the first seal may be configured to maintain sterility of a first sterile space enclosed within the cap and adjacent to the first valve member. In various embodiments, while the cap is uncoupled from the first valve body after the first coupling portion is coupled with the connection member, the sterility of the first sterile space is maintained. The second coupling portion may be sealed so as to maintain sterility of a second sterile space adjacent to the second valve member. In some embodiments, while the connection member is in the second position, the first sterile space is in fluid communication with the second sterile space. In particular embodiments, while the connection member is in the second position, the second valve body may be slidable along the second longitudinal axis such that the first valve member can become engaged with the second valve member to thereby open a fluid pathway between the first and second end ports. The fluid pathway may be a sterile fluid pathway. The aseptic fluid coupling system may further comprise a flexible member coupled to the housing and to the connection member. The flexible member may reconfigure while the connection member is moved between the first position and the second position. The flexible member may be configured to maintain a sterile seal of the second coupling portion while the connection member is moved between the first position and the second position. In some embodiments, while: (i) the first coupling portion is coupled with the connection member, (ii) the connection member is in the first position, and (iii) the cap is coupled with the first valve body, the connection member may be prevented from moving toward the second position. In various embodiments, while: (i) the first coupling portion is coupled with the connection member and (ii) the connection member is in the first position, the cap can be uncoupled from the first valve body by a cap movement comprising a translation of the cap along the first longitudinal axis. The cap movement may further comprise a rotation of the cap about the first longitudinal axis prior to the translation of the cap along the first longitudinal axis. In some embodiments, while: (i) the first coupling portion is coupled with the connection member, (ii) the connection member is in the first position, and (iii) the cap is uncoupled with the first valve body, the connection member may be free to move toward the second position. In particular embodiments, while: (i) the first coupling portion is coupled with the connection member and (ii) the connection member is in the second position, the first longitudinal axis is coincident with the second longitudinal axis, and a fluid flow path from the first end port to the second end port can be opened by a displacement of the second valve body in relation to the housing and toward the first valve body.

In another implementation, an aseptic fluid coupling system includes a first coupling portion and a second coupling portion configured to releasably couple with the first coupling portion. The first coupling portion includes a first valve body defining a first longitudinal axis and a first end port, a first valve member disposed within the first valve body, and a cap that is releasably coupleable to the first valve body. The second coupling portion includes a housing, a second valve body coupled with the housing (the second valve body defining a second longitudinal axis and a second end port), a second valve member disposed within the second valve body, and a connection member configured to releasably couple with the first coupling portion. The connection member is slidably coupled with the housing and slidable in relation to the housing between a first position and a second position. While the first coupling portion is coupled with the connection member, the first coupling portion is positionable in a first position where the first longitudinal axis is spaced apart from the second longitudinal axis and a second position where the first longitudinal axis is coincident with the second longitudinal axis.

Such an aseptic fluid coupling system may optionally include one or more of the following features. The second valve body may be slidably coupled with the housing. The second valve body may be slidable along the second longitudinal axis. The connection member may be slidable between the first position and the second position along a path that is transverse to the second longitudinal axis. The first longitudinal axis may be parallel to the second longitudinal axis. The cap may be releasably coupleable to the first valve body by a bayonet connection. In some embodiments, while the cap is coupled to the first valve body, a first seal exists between the cap and the first valve body. The first seal may be configured to maintain sterility of a first sterile space enclosed within the cap and adjacent to the first valve member. In various embodiments, while the cap is uncoupled from the first valve body after the first coupling portion is coupled with the connection member, the sterility of the first sterile space is maintained. The second coupling portion may be sealed so as to maintain sterility of a second sterile space adjacent to the second valve member. In some embodiments, while the connection member is in the second position, the first sterile space is in fluid communication with the second sterile space. In particular embodiments, while the connection member is in the second position, the second valve body is slidable along the second longitudinal axis such that the first valve member can become engaged with the second valve member to thereby open a fluid pathway between the first and second end ports. The fluid pathway may be a sterile fluid pathway. The aseptic fluid coupling system may further comprise a flexible member coupled to the housing and to the connection member. The flexible member may be configured to flex while the connection member is moved between the first position and the second position. The flexible member may be configured to maintain a sterile seal of the second coupling portion while the connection member is moved between the first position and the second position. In some embodiments, while: (i) the first coupling portion is coupled with the connection member, (ii) the connection member is in the first position, and (iii) the cap is coupled with the first valve body, the connection member may be prevented from moving toward the second position. In various embodiments, while: (i) the first coupling portion is coupled with the connection member and (ii) the cap is uncoupled from the first valve body, the connection member may be slidable orthogonally in relation to the second longitudinal axis between the first position and the second position. In particular embodiments, while: (i) the first coupling portion is coupled with the connection member and (ii) the connection member is in the first position, the cap may be uncoupleable from the first valve body by a cap movement comprising a translation of the cap along the first longitudinal axis. The cap movement may further comprise a rotation of the cap about the first longitudinal axis prior to the translation of the cap along the first longitudinal axis.

In another implementation, an aseptic fluid coupling system comprises a first coupling portion and a second coupling portion to releasably couple with the first coupling portion. The first coupling portion includes a first valve body defining a first longitudinal axis and a first end port, a first valve member disposed within the first valve body, and a cap that is releasably coupleable to the first valve body. The cap encloses at least a portion of the first valve body while the cap is coupled to the first valve body. The second coupling portion includes a housing, a second valve body coupled with the housing, the second valve body defining a second longitudinal axis and a second end port, a second valve member disposed within the second valve body, and a connection member configured to releasably couple with the first coupling portion. While the first coupling portion is coupled with the connection member, the cap can by uncoupled from the first valve body by a cap movement comprising a translation of the cap along the first longitudinal axis.

Such an aseptic fluid coupling system may optionally include one or more of the following features. The cap movement may further comprise a rotation of the cap about the first longitudinal axis prior to the translation of the cap along the first longitudinal axis. The first valve member may be movable between (i) an open position that allows fluid flow through the first valve body and (ii) a closed position that blocks fluid flow through the first valve body. The first valve member may be spring-biased to be located in the closed position. The second valve member may be movable between (i) an open position that allows fluid flow through the second valve body and (ii) a closed position that blocks fluid flow through the second valve body. The second valve member may be spring-biased to be located in the closed position. The second valve body may be slidably coupled with the housing. The second valve body may be slidable along the second longitudinal axis. The connection member may be slidably coupled with the housing. The connection member may be slidable between the first position and the second position along a path that is transverse to the second longitudinal axis. In some embodiments, while the connection member is in the second position, the connection member may be coaxial with the second longitudinal axis. In various embodiments, while the first coupling portion is coupled to the connection member, the first longitudinal axis is coincident with the second longitudinal axis. In particular embodiments, while the connection member is in the first position and the first coupling portion is coupled to the connection member, the first longitudinal axis may be spaced apart from the second longitudinal axis. The first longitudinal axis may be parallel to the second longitudinal axis. The cap may be releasably coupleable to the first valve body using a bayonet connection. In some embodiments, while the cap is coupled to the first valve body, a first seal exists between the cap and the first valve body. The first seal may be configured to maintain sterility of a first sterile space enclosed within the cap and adjacent to the first valve member. In various embodiments, while the cap is uncoupled from the first valve body after the first coupling portion is coupled with the connection member, the sterility of the first sterile space may be maintained. The second coupling portion may be sealed so as to maintain sterility of a second sterile space adjacent to the second valve member. In some embodiments, while the connection member is in the second position, the first sterile space is in fluid communication with the second sterile space. In particular embodiments, while the connection member is in the second position, the second valve body may be slidable along the second longitudinal axis such that the first valve member can become engaged with the second valve member to thereby open a fluid pathway between the first and second end ports. The fluid pathway may be a sterile fluid pathway. The aseptic fluid coupling system may further comprise a flexible member coupled to the housing and to the connection member. The flexible member may reconfigure while the connection member is moved between the first position and the second position. The flexible member may be configured to maintain a sterile seal of the second coupling portion while the connection member is moved between the first position and the second position. In some embodiments, while: (i) the first coupling portion is coupled with the connection member, (ii) the connection member is in the first position, and (iii) the cap is coupled with the first valve body, the connection member is prevented from moving toward the second position. In various embodiments, while: (i) the first coupling portion is coupled with the connection member, (ii) the connection member is in the first position, and (iii) the cap is uncoupled with the first valve body, the connection member may be free to move toward the second position. In particular embodiments, while: (i) the first coupling portion is coupled with the connection member and (ii) the connection member is in the second position, the first longitudinal axis may be coincident with the second longitudinal axis, and a fluid flow path from the first end port to the second end port can be opened by a displacement of the second valve body in relation to the housing and toward the first valve body.

In another implementation, a method of using a reusable, aseptic fluid coupling system includes connecting a first coupling portion of the aseptic fluid coupling system to a second coupling portion of the aseptic fluid coupling system, moving the connection member (with the first coupling portion coupled thereto) to a second position in relation to the housing, and engaging the first valve member with the second valve member to open a fluid pathway between the first and second end ports. The first coupling portion can include: (i) a first valve body defining a first longitudinal axis and a first end port; (ii) a first valve member disposed within the first valve body; and (iii) a cap that is releasably coupled to the first valve body. The second coupling portion can include: (a) a housing; (b) a second valve body coupled with the housing, the second valve body defining a second longitudinal axis and a second end port; (c) a second valve member disposed within the second valve body; and (d) a connection member releasably coupled with the first coupling portion and disposed at a first position in relation to the housing.

Such a method of using a reusable, aseptic fluid coupling system may optionally include one or more of the following features. The first valve member and the second valve member may be each sterile, and the fluid pathway may be a sterile fluid pathway. The method may also include, after opening the sterile fluid pathway, disengaging the first valve member from the second valve member to close the fluid pathway between the first and second end ports. The method may also include, after disengaging the first valve member from the second valve member, disconnecting the first coupling portion from the second coupling portion, wherein the first valve member and the second valve member each remain sterile. The method may also include, after disconnecting the first coupling portion from the second coupling portion, reconnecting the first coupling portion to the second coupling portion and re-opening the sterile fluid pathway, wherein the first valve member and the second valve member each remain sterile.

In another implementation, a fluid coupling device includes a first coupling portion and a second coupling portion. The first coupling portion includes a first valve body defining a first longitudinal axis and a first end port, and a cap that is releasably coupleable to the first valve body. The second coupling portion includes a housing, a second valve body coupled with the housing (the second valve body defining a second longitudinal axis and a second end port), and a connection member configured to releasably couple with the first coupling portion. The connection member is movably coupled with the housing between a first position in which the first and second longitudinal axes are dissimilar from each other and a second position in which the first and second longitudinal axes are coincident.

In another implementation, an aseptic fluid coupling system includes a first coupling portion, a second coupling portion that is releasably coupleable with the first coupling portion, and a middle coupling portion configured to releasably connect with the first coupling portion and with the second coupling portion. The first coupling portion includes a first valve body defining a first end port, a first valve member disposed within the first valve body, and a first cap that is releasably coupleable to the first valve body. The first cap encloses at least a portion of the first valve body while the first cap is coupled to the first valve body. The second coupling portion includes a second valve body defining a second end port, a second valve member disposed within the second valve body (the second valve member being engageable with the first valve member such that, while the first valve member and the second valve member are engaged, a fluid flow path is open between the first end port and the second end port), and a second cap that is releasably coupleable to the second valve body. The second cap encloses at least a portion of the second valve body while the second cap is coupled to the second valve body. The middle coupling portion defines an enclosure. The middle coupling portion is configured such that, while the first coupling portion and the second coupling portion are connected to the middle coupling portion, the first coupling portion and the second coupling portion can be coupled to each other within the enclosure.

Such an aseptic fluid coupling system may optionally include one or more of the following features. The middle coupling portion may further comprise a first cap trap and a second cap trap. The first cap trap may be releasably coupleable with the first cap and the second cap trap is releasably coupleable with the second cap. The first cap trap and the second cap trap may be disposed within the enclosure. In some embodiments, while the first coupling portion and the second coupling portion are coupled to each other within the enclosure, the first cap trap is coupled to the first cap and the second cap trap is coupled to the second cap. The first cap trap coupled to the first cap and the second cap trap coupled to the second cap may be each loosely contained within the enclosure.

In another implementation, an aseptic fluid coupling system includes a first coupling portion and a second coupling portion that is configured to releasably couple with the first coupling portion. The first coupling portion includes a first valve body defining a first end port and a first longitudinal axis, a first valve member disposed within the first valve body, and a first cap that is releasably coupleable to the first valve body. The first cap encloses at least a portion of the first valve body while the first cap is coupled to the first valve body. The second coupling portion includes an inner housing defining a second end port (the inner housing configured to releasably couple with the first cap), a second valve member coupled to the inner housing and defining a second longitudinal axis (the second valve member configured to releasably engage with the first valve member), and an outer housing that is rotatable and translatable in relation to the inner housing. The outer housing includes a connection structure that is configured to releasably couple with the first valve body. The connection structure defines a third longitudinal axis.

Such an aseptic fluid coupling system may optionally include one or more of the following features. The first coupling portion may be coupleable with the second coupling portion such that the first longitudinal axis and the third longitudinal axis are coincident and spaced apart from the second longitudinal axis. In some embodiments, while the first coupling portion is coupled with the second coupling portion, the inner housing is longitudinally translatable in relation to the outer housing. Longitudinal translation of the inner housing in relation to the outer housing may cause the cap to uncouple from the first valve body. In various embodiments, while the cap is uncoupled from the first valve body, the inner housing may be rotatable in relation to the outer housing such that the first longitudinal axis can be aligned coincident with the second longitudinal axis. In some embodiments, while the first longitudinal axis is aligned coincident with the second longitudinal axis, the first valve member can be engaged with the second valve member to establish a fluid pathway between the first end port and the second end port. The fluid pathway may be a sterile fluid pathway.

In another implementation, an aseptic fluid coupling system includes a first means for coupling to a first portion of a fluid line and a second means for coupling to a second portion of the fluid line and for repeatably connecting and disconnecting with the first means in a sterile, aseptic manner.

Particular embodiments of the subject matter described in this document can be implemented to realize one or more of the following advantages. First, in some embodiments the fluid coupling systems provided herein are configured to allow fluid flow therethrough in a sterile/isolated manner. Moreover, in some embodiments the fluid coupling systems provided herein are configured to allow multiple connection and disconnection cycles while maintaining the sterility/isolation of the fluid pathway through the coupling system, even while the fluid coupling systems are used in a non-sterile environment and/or in an environment containing materials considered as contaminants in relation to the fluid flowing through the coupling.

Second, in some embodiments the fluid coupling systems are configured to prevent undesired or improper movements during the coupling and/or decoupling processes of the fluid coupling portions. For example, in some embodiments the fluid coupling systems include physical features that preclude a user from implementing actions that are inconsistent with the proper process for coupling the portions of the fluid coupling systems to establish a sterile fluid pathway therethrough.

Third, in some embodiments, the fluid coupling systems may advantageously provide a user with audible and/or tactile feedback in reference to the motions performed for physically connecting and disconnecting the two portions of the fluid coupling systems from each other. Such audible and/or tactile feedback can provide the user with an efficient and conclusive indication or confirmation of the proper function and desired configuration of the fluid coupling systems.

Fourth, some embodiments of the fluid coupling systems provide an improved aseptic connection and disconnection capability that may optionally reduce or eliminate the need for sterile rooms or sterile benchtop environments in some cases. As such, these embodiments of the aseptic fluid coupling systems described herein may facilitate efficient and cost-effective operations or uses that would otherwise be high-cost or even cost prohibitive in some traditional settings that required the disconnection of particular fluid couplings in a sterile room or within a sterile flow-hood to prevent biological contamination.

Fifth, some embodiments of the fluid coupling devices provided herein are advantageously designed with a robust locking system. That is, when the two halves of the coupling system are operably connected with each other, they are also mechanically locked together. In some embodiments, to release the lock, two latches on the coupling must be simultaneously depressed. This redundant requirement (e.g., simultaneous actuation of two latches or other actuators) for unlocking the coupling portions may reduce the likelihood of unintentional disconnections (and the associated potential for unintentional contamination of the fluid flowing through the fluid coupling device).

Unless otherwise defined, all technical and scientific terms used herein have the same meaning as commonly understood by one of ordinary skill in the art to which this disclosure pertains. In addition, the materials, methods, and examples of the embodiments described herein are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 16 is an exploded perspective view of a repeatable sterile fluid coupling system, in accordance with some embodiments. The illustrated repeatable sterile fluid coupling includes the first fluid coupling portion of FIG. 10 and the second fluid coupling portion of FIG. 13.

FIG. 17 is an exploded longitudinal side view of the repeatable sterile fluid coupling system of FIG. 16.

FIG. 18 is an exploded longitudinal cross-section side view of the repeatable sterile fluid coupling system of FIG. 16.

FIG. 25 is a perspective view of the repeatable sterile fluid coupling system of FIG. 16 in a third configuration.

FIG. 26 is a longitudinal side view of the repeatable sterile fluid coupling system as configured in FIG. 25.

FIG. 27 is a longitudinal cross-sectional side view of the repeatable sterile fluid coupling system as configured in FIG. 25.

FIG. 28 is a perspective view of the repeatable sterile fluid coupling system of FIG. 16 in a fourth configuration. A fluid flow path exists through the repeatable sterile fluid coupling system in the fourth configuration.

FIG. 29 is a longitudinal side view of the repeatable sterile fluid coupling system as configured in FIG. 28.

FIG. 30 is a longitudinal cross-sectional side view of the repeatable sterile fluid coupling system as configured in FIG. 28.

FIG. 57 is an exploded perspective view of a repeatable sterile fluid coupling system, in accordance with some embodiments. The illustrated repeatable sterile fluid coupling includes the first fluid coupling portion of FIG. 51 and the second fluid coupling portion of FIG. 54.

FIG. 58 is an exploded longitudinal side view of the repeatable sterile fluid coupling system of FIG. 57.

FIG. 59 is an exploded longitudinal cross-section side view of the repeatable sterile fluid coupling system of FIG. 57.

FIG. 60 is a perspective view of the repeatable sterile fluid coupling system of FIG. 57 in a first configuration.

FIG. 61 is a longitudinal side view of the repeatable sterile fluid coupling system as configured in FIG. 60.

FIG. 62 is a longitudinal cross-sectional side view of the repeatable sterile fluid coupling system as configured in FIG. 60.

FIG. 63 is a perspective view of the repeatable sterile fluid coupling system of FIG. 57 in a second configuration.

FIG. 64 is a longitudinal side view of the repeatable sterile fluid coupling system as configured in FIG. 63.

FIG. 65 is a longitudinal cross-sectional side view of the repeatable sterile fluid coupling system as configured in FIG. 63.

FIG. 69 is a perspective view of the repeatable sterile fluid coupling system of FIG. 57 in a fourth configuration. A fluid flow path exists through the repeatable sterile fluid coupling system in the fourth configuration.

FIG. 70 is a longitudinal side view of the repeatable sterile fluid coupling system as configured in FIG. 69.

FIG. 71 is a longitudinal cross-sectional side view of the repeatable sterile fluid coupling system as configured in FIG. 69.

Like reference numbers represent corresponding parts throughout.

DETAILED DESCRIPTION OF ILLUSTRATIVE EMBODIMENTS

Figure 1:
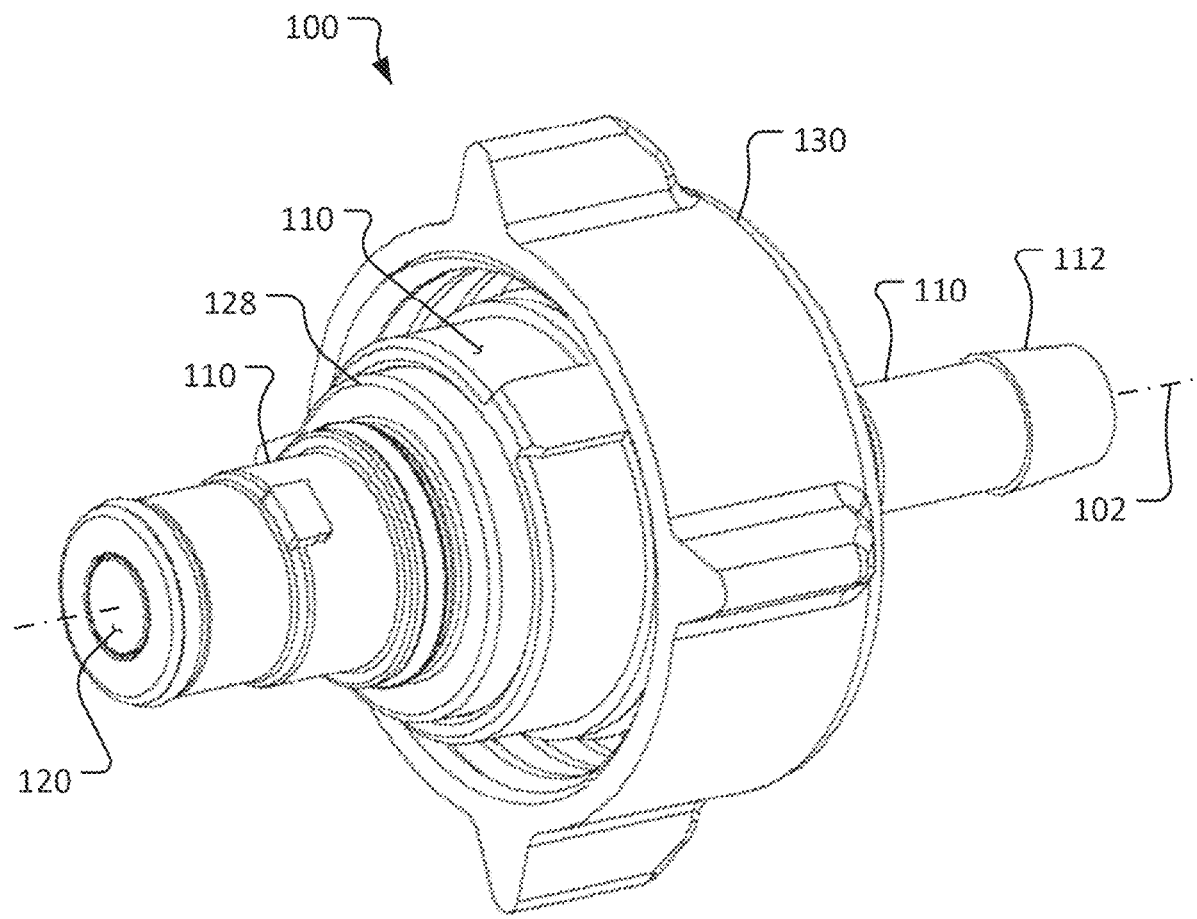
FIG. 1 is a perspective view of a fluid coupling device, in accordance with some embodiments provided herein.
Figure 2:
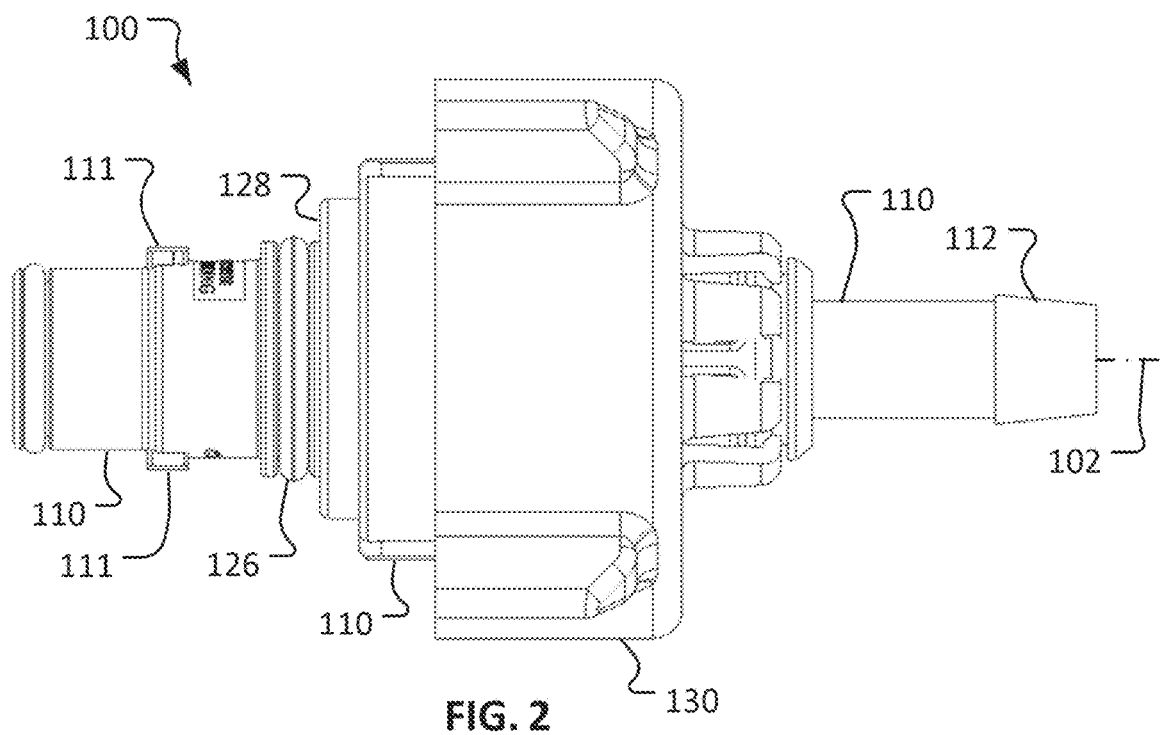
FIG. 2 is a longitudinal side view of the fluid coupling device of FIG. 1.
Figure 3:
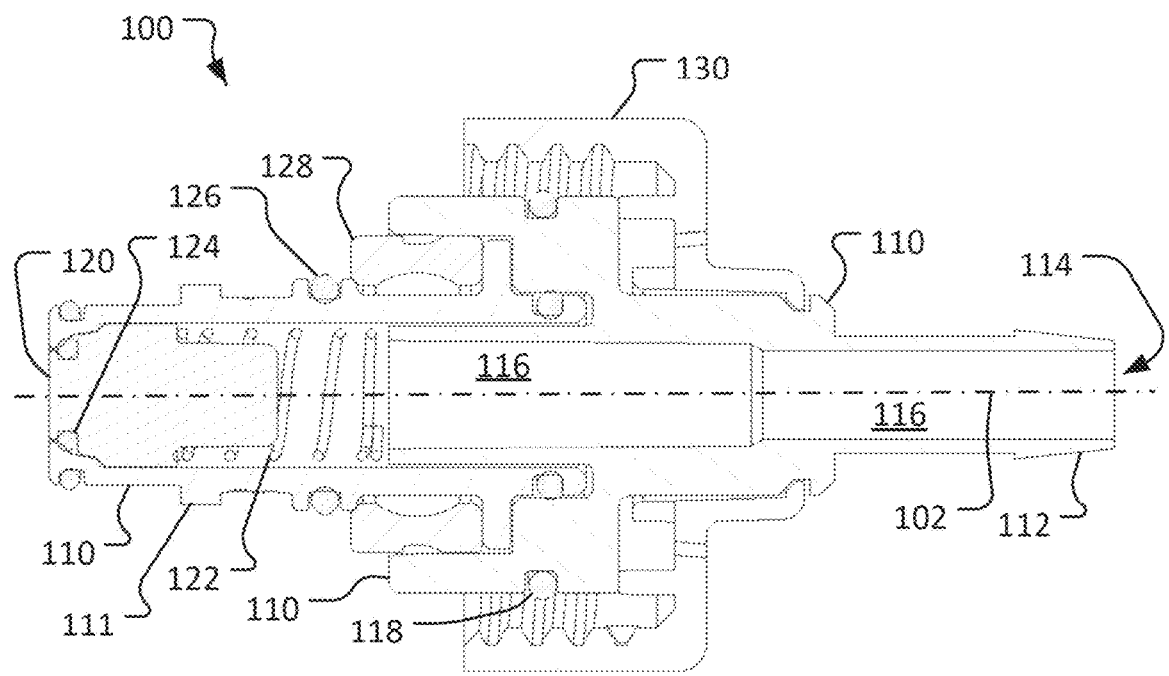
FIG. 3 is a longitudinal cross-section view of the fluid coupling device of FIG. 1.

Referring to FIGS. 1-3, some embodiments of a reusable aseptic fluid coupling system include a fluid coupling device 100. As described further below, the fluid coupling device 100 may be releasably coupleable with a cap that protects the sterility/isolation of the fluid flow path within the fluid coupling device 100 prior to mating the fluid coupling device 100 with another fluid coupling.

In the depicted embodiment, the fluid coupling device 100 includes a valve body 110, a valve member 120, and a connection structure 130. The valve member 120 is movably coupled in relation to the valve body 110. The connection structure 130 is coupled to the valve body 110, and in some embodiments the connection structure 130 is movably coupled in relation to the valve body 110.

In the depicted embodiment, the valve body 110 includes an end portion 112 that defines an end port 114. The end portion 112 may be configured for connecting the fluid coupling device 100 to another element of a fluid system, such as a tube, container, valve, fitting, and other types of fluid system components. Accordingly, end portion 112 may include various configurations such as, but not limited to, a barbed fitting (as shown), a luer fitting, a compression fitting, a threaded fitting (internal or external), a sanitary fitting, a pigtail, a T-fitting, a Y-fitting, a bag fitment, and any other suitable type of configuration such that the fluid coupling device 100 is suitable for connection to a fluid system as desired. In some embodiments, the fluid coupling device 100 may be supplied with a removable cap (not shown), or another type of component, that is releasably coupled with the end portion 112, and that covers end port 114.

The valve body 110 defines a fluid pathway 116 that terminates at the end port 114. In the depicted embodiment, the patency of the fluid pathway 116 is determined by the position of the valve member 120 in relation to the valve body 110. That is, the valve member 120 can move in relation to the valve body 110 to open the fluid pathway 116 through the fluid coupling device 100, or to close the fluid pathway 116 through the fluid coupling device 100. In the illustrated, non-limiting configuration, the valve member 120 can translate along a longitudinal axis 102 defined by the valve body 110. In some embodiments, the longitudinal axis 102 is coaxial with the fluid pathway 116, but such an arrangement is not required in all embodiments.

In the illustrated arrangement, the valve member 120 is positioned in a closed position in which the valve member 120 provides a fluidic-sealed occlusion of the fluid pathway 116. A spring member 122 is included, in the depicted embodiment, to bias the valve member 120 to the closed position. A peripheral elastomeric seal 124 (e.g., an o-ring) is included such that the fluid pathway 116 is sealed closed while the valve member 120 is in the closed position.

As described further below, in some embodiments the valve member 120 can be engaged by another valve member to force the valve member 120 to move in relation to the valve body 110 (e.g., toward the end portion 114), and to thereby open the fluid pathway 116 through fluid coupling device 100.

In the depicted embodiment, the valve member 120 is a poppet valve. In some embodiments, other types of valve members 120 are alternatively or additionally used in the valve body 110. For example, in some embodiments the valve member 120 is a type of valve such as, but not limited to, a butterfly valve, a ball valve, a duckbill valve, a diaphragm valve, a needle valve, a pinch valve, a plug valve, and the like.

In some embodiments, the materials from which one or more of the components of the fluid coupling device 100 are made of include thermoplastics. In particular embodiments, the materials from which the components of the fluid coupling device 100 are made of are thermoplastics, such as, but not limited to, polycarbonate, polysulfone, polyether ether ketone, polysulphide, polyester, polyvinylidene fluoride (PVDF), polyethylene, polyphenylsulfone (PPSU; e.g., Radel®), polyetherimide (PEI; e.g., Ultem®), polypropylene, polyphenylene, polyaryletherketone, and the like, and combinations thereof. In some embodiments, the materials from which one or more of the components of the fluid coupling device 100 are made of include metals such as, but not limited to stainless steel. In some embodiments, the fluid coupling device 100 is metallic-free. That is, in some embodiments no metallic materials are included in the fluid coupling device 100. For example, in some embodiments no metallic springs are included in the fluid coupling device 100. Alternatively, in some embodiments the spring member 122 is a metallic spring (e.g., spring steel, stainless steel, and the like). In some embodiments, the seals (e.g., seal 124 et al.) are made of materials such as, but not limited to, silicone, fluoroelastomers (FKM), ethylene propylene diene monomer (EPDM), and the like.

As described further below, in some embodiments portions of the fluid coupling device 100 are sterile, while other portions of the fluid coupling device 100 are non-sterile. For example, in some embodiments at least valve member 120 and fluid pathway 116 are sterile, whereas at least some other portions of the fluid coupling device 100 (e.g., connection structure 130) are non-sterile.

Figure 4:
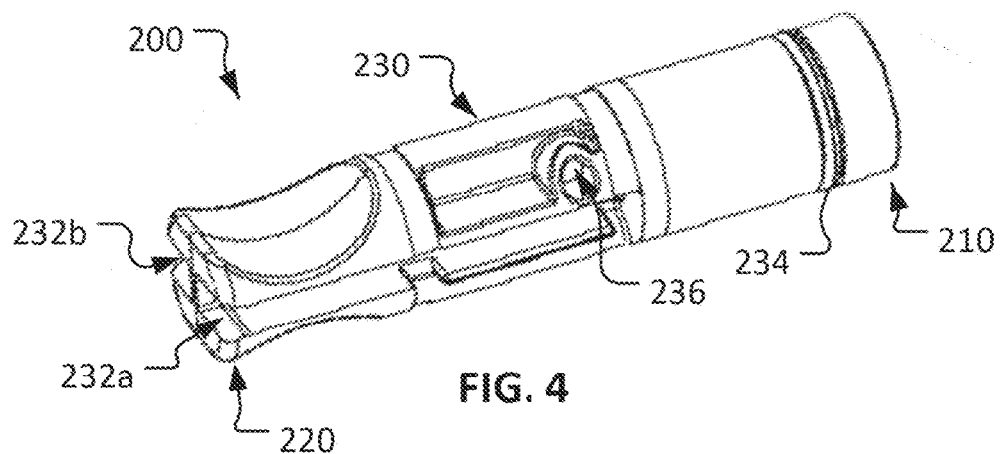
FIG. 4 is a perspective view of a cap that mates with the fluid coupling device of FIG. 1, in accordance with some embodiments provided herein.
Figure 5:
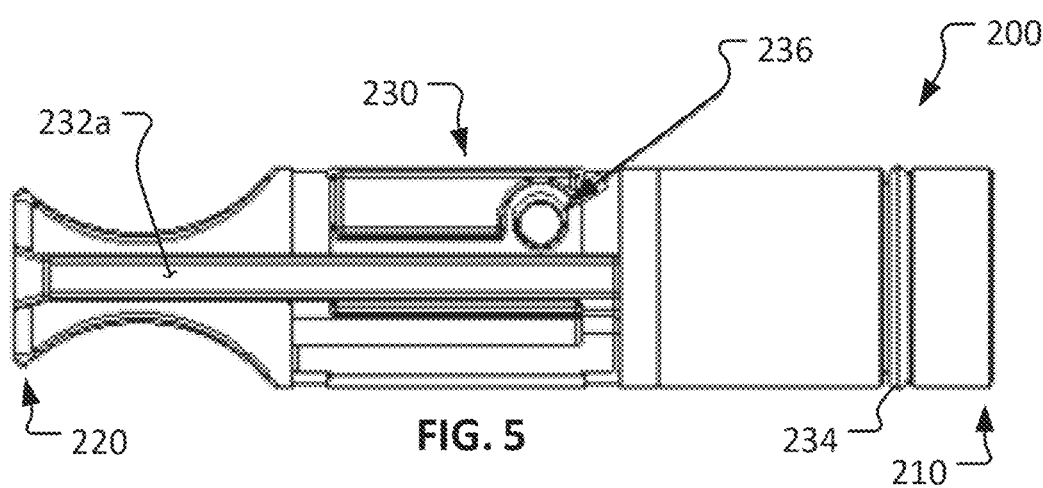
FIG. 5 is a longitudinal side view of the cap of FIG. 4.
Figure 6:
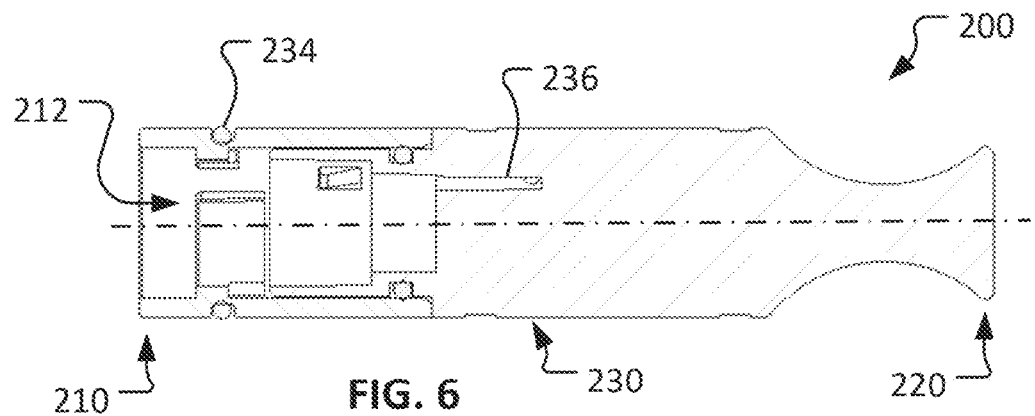
FIG. 6 is a longitudinal cross-sectional view of the cap of FIG. 4.
Figure 7:
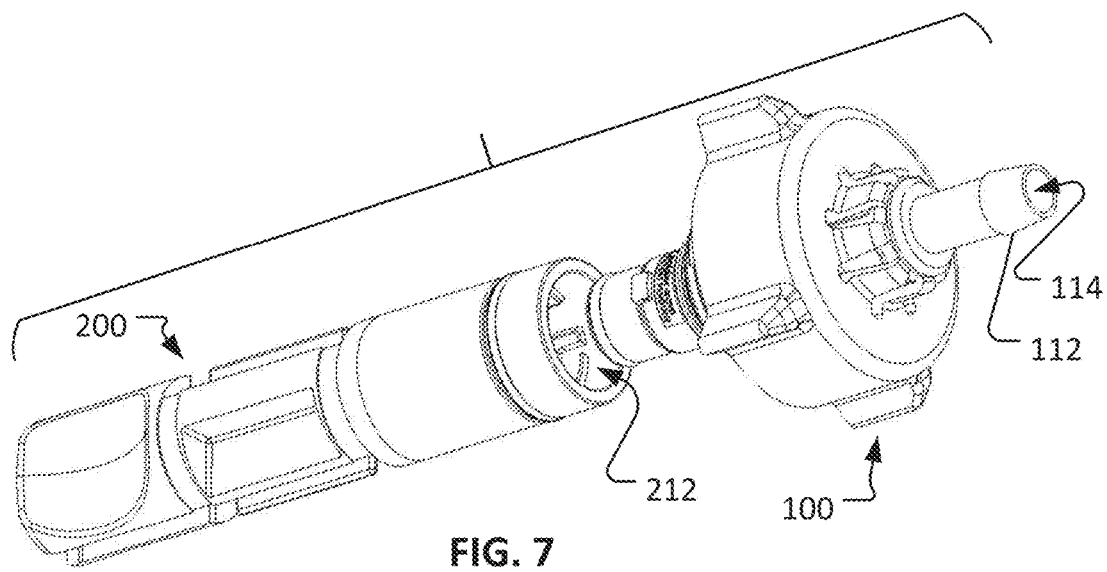
FIG. 7 is an exploded perspective view of the fluid coupling device of FIG. 1 and the cap of FIG. 4.
Figure 8:
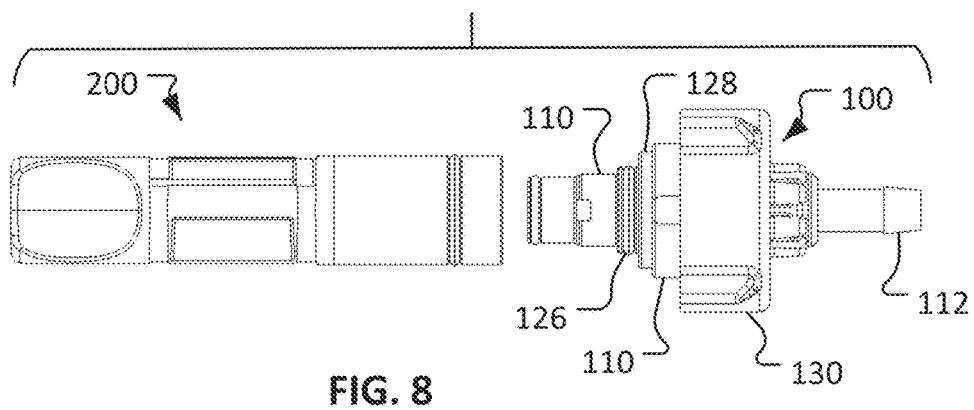
FIG. 8 is an exploded longitudinal side view of the fluid coupling device of FIG. 1 and the cap of FIG. 4.
Figure 9:
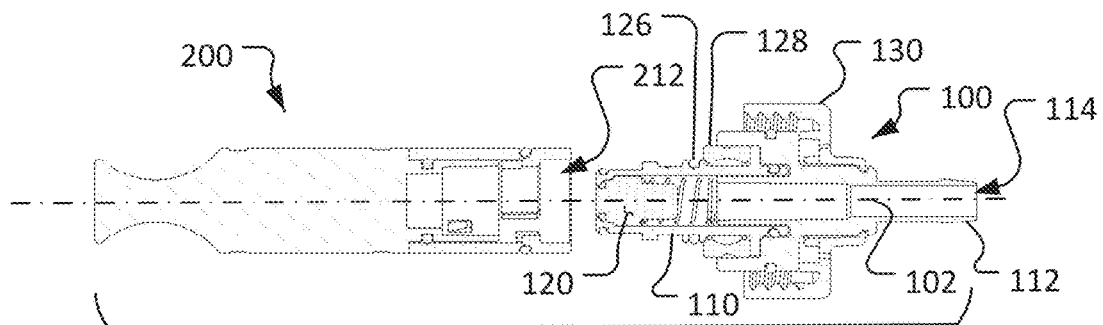
FIG. 9 is an exploded longitudinal cross-sectional view of the fluid coupling device of FIG. 1 and the cap of FIG. 4.
Figure 10:
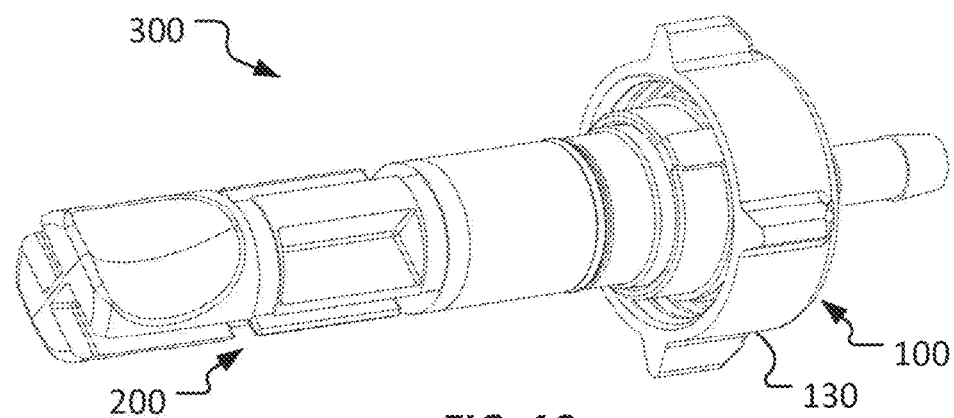
FIG. 10 is a perspective view of the fluid coupling device of FIG. 1 coupled with the cap of FIG. 4 to form a first fluid coupling portion of a repeatable sterile fluid coupling system in accordance with some embodiments.
Figure 11:
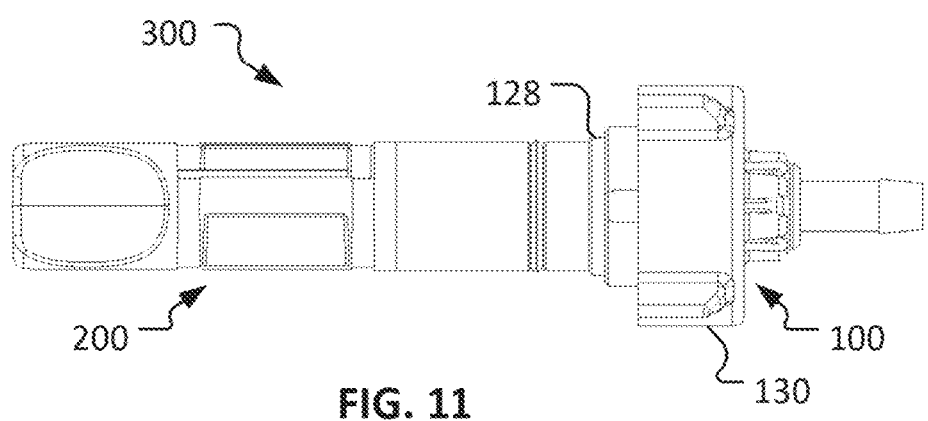
FIG. 11 is a longitudinal side view of the fluid coupling portion of FIG. 10.
Figure 12:
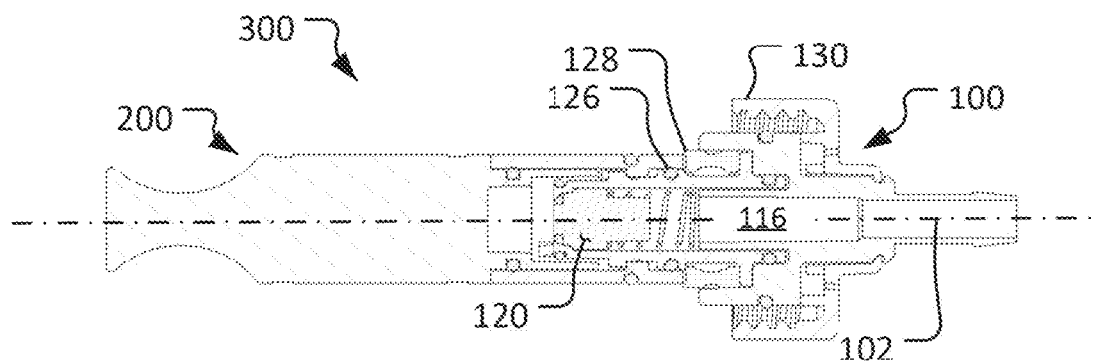
FIG. 12 is a longitudinal cross-sectional side view of the fluid coupling portion of FIG. 10.

Referring also to FIGS. 4-6, a cap 200 can be configured to releasably couple with the fluid coupling device 100. The cap 200 includes a first end 210, a second end 220, and a cap body 230 therebetween. In the depicted embodiment, an optional vent 236 is included.

The first end 210 can be configured to releasably couple (e.g., mate or engage) with the fluid coupling device 100. For example, in the depicted embodiment the first end 210 includes a bore 212 that is configured to receive a portion of the valve body 110, and to releasably couple with the valve body 110. In the depicted embodiment, the first end 210 and the valve body 110 are configured for interconnection using a bayonet-style coupling arrangement. The bayonet-style coupling arrangement includes one or more radial projections 111 on the valve body 110 that are releasably engageable with one or more complementary slots defined in the bore 212 of the cap 200. The one or more complementary slots defined in the bore 212 are L-shaped so that the process of engaging the one or more radial projections 111 within the slots includes a relative longitudinal movement followed by a relative rotational movement (i.e., a push-together motion and a turn-to-latch motion). The rotational movement is typically about a ¼ turn or less, but may be more than a ¼ turn in some embodiments. The bayonet-style coupling arrangement can include a detention aspect that provides a positive lock between the fluid coupling device 100 and the cap 200 when fully mated together. In some embodiments, other types of interconnections can be used such as, but not limited to, threaded connections, detent pin connections, latches, hinges, and the like, and combinations thereof.

In the depicted embodiment, the second end 220 is configured for convenient manual manipulation. That is, in the depicted embodiment the second end 220 includes surface contours that facilitate manual gripping and manipulations such as turning, pulling, pushing, and the like. In some embodiments, other types of features may be additionally or alternatively included to facilitate convenient manual gripping and manipulations of cap 200. Such features may include, but are not limited to, knurling, stippling, other types of texturing, flexible elastomeric inserts, and the like, and combinations thereof.

In some embodiments, such as the depicted embodiment, the cap 200 includes features that configure the cap 200 to restrictively mate with another coupling portion in one or more desired relative orientations (as described further below). For example, in the depicted embodiment the cap 200 includes slots 232a and 232b. The slots 232a and 232b are configured to receive one or more projections of the other coupling portion, and to thereby restrict the relative movements between the cap 200 and the other coupling portion to only particular relative movements as desired (e.g., like a key and keyway arrangement). In some embodiments, other features can be included on the cap 200 to achieve the purpose of restrictively mating with another coupling portion in one or more desired relative orientations. For example, in some embodiments features such as, but not limited to, gear teeth, splines, threads, compression fits, and the like, and combinations thereof can be included as part of the cap 200.

In the depicted embodiment, the cap 200 also includes the seal member 234. The seal member 234 surrounds the outer periphery of the cap body 230, and projects at least slightly proud therefrom. As described further below, the seal member 234 is configured to seal with a portion of another coupling portion, and to maintain the sterility of sterile portions of fluid coupling device 100 and/or the isolation of portions of the fluid coupling device 100 as desired.

The cap 200 can also include the optional vent 236 in some embodiments. The vent 236 provides an air-transmissible pathway between the bore 212 and the regions exterior of the cap 200. In some embodiments, a filter media or porous element is included within the vent 236. Such a filter or porous element can serve to inhibit transmission of particles and/or microorganisms, while still allowing transmission of air therethrough. In some embodiments, the filter media or porous element of the vent 236 allows the transmission of materials that are smaller than about 0.2 µm in size, while inhibiting the transmission of materials that are larger. In some embodiments, the filter media or porous element of the vent 236 inhibits the transmission of materials that are larger than about 0.1 µm, or about 0.3 µm, or about 0.4 µm, or about 0.5 µm, or larger than 0.5 µm, while allowing the transmission of materials that are smaller.

The cap 200 can be constructed of any of the materials described above in reference to fluid coupling device 100.

Referring to FIGS. 7-12, the fluid coupling device 100 and the cap 200 are configured to releasably couple with each other to become an assembled first coupling portion 300. In the coupled configuration of the first coupling portion 300, at least the portion of the valve body 110 that houses the valve member 120 is received in the bore 212 of the cap 200.

In some implementations, the assembled coupling portion 300 (and the other coupling portions described herein) is sterilized prior to use (e.g., using any suitable sterilization method such as gamma sterilization, ethylene oxide sterilization, e-beam sterilization, Noxilizer™ sterilization, Revox® sterilization, or using an autoclave, and the like). In some cases during the sterilization, a cap (not shown) may be included on the end portion 112 to seal the end port 114 (and, hence, the fluid pathway 116). In some cases the assembled coupling portion 300 may be coupled with tubing and/or other components prior to sterilization, and the assembly is sterilized in the coupled configuration. After sterilization, the cap 200 maintains the sterility of the portions of the fluid coupling device 100 that are within the bore 212, and of the fluid pathway 116. The sterility is maintained, while the cap 200 is coupled with the fluid coupling device 100, at least in part because of a gasket 126 and/or an optional seal 128 located between the cap 200 and the valve body 110. Hence, even while the sterilized coupling portion 300 is exposed to a non-sterile environment, the cap 200 can serve to maintain the sterility of the portions of the fluid coupling device 100 that will contact a fluid being transmitted through the fluid coupling device 100 (in the manner described further below).

In the depicted embodiment, the coupling mechanism between the cap 200 and the fluid coupling device 100 is a bayonet-style connection. In some embodiments, other types of coupling mechanisms are used such as, but not limited to, threaded connections, press-fit connections, latch connections, cam-lock connections, over-center connections, and the like, and combinations thereof.

Figure 13:
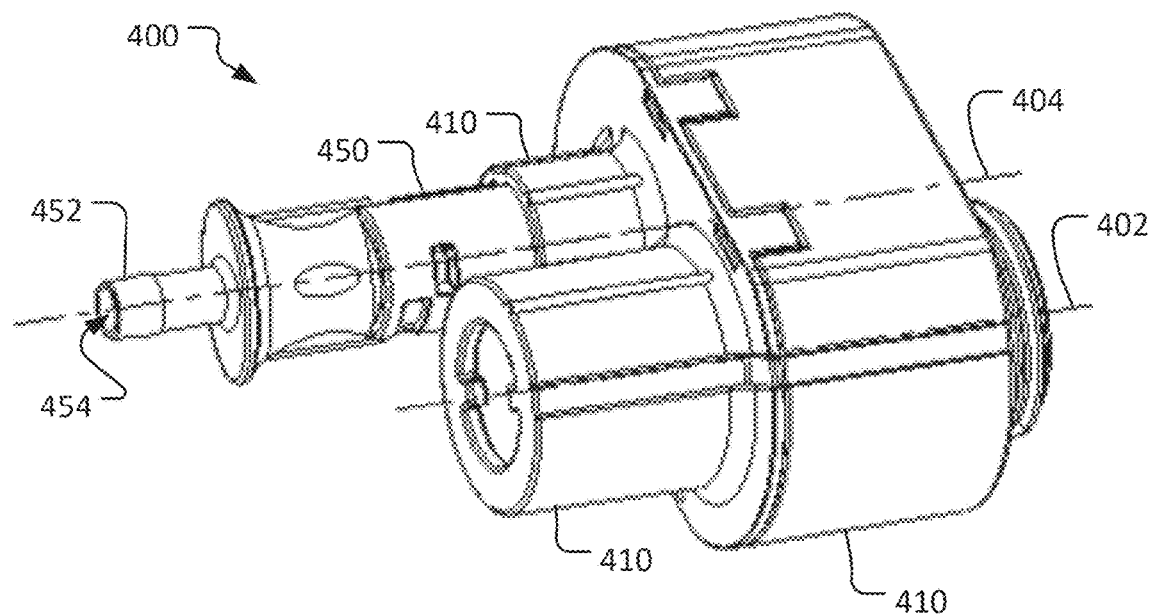
FIG. 13 is a perspective view of a second fluid coupling portion of a repeatable sterile fluid coupling, in accordance with some embodiments.
Figure 14:
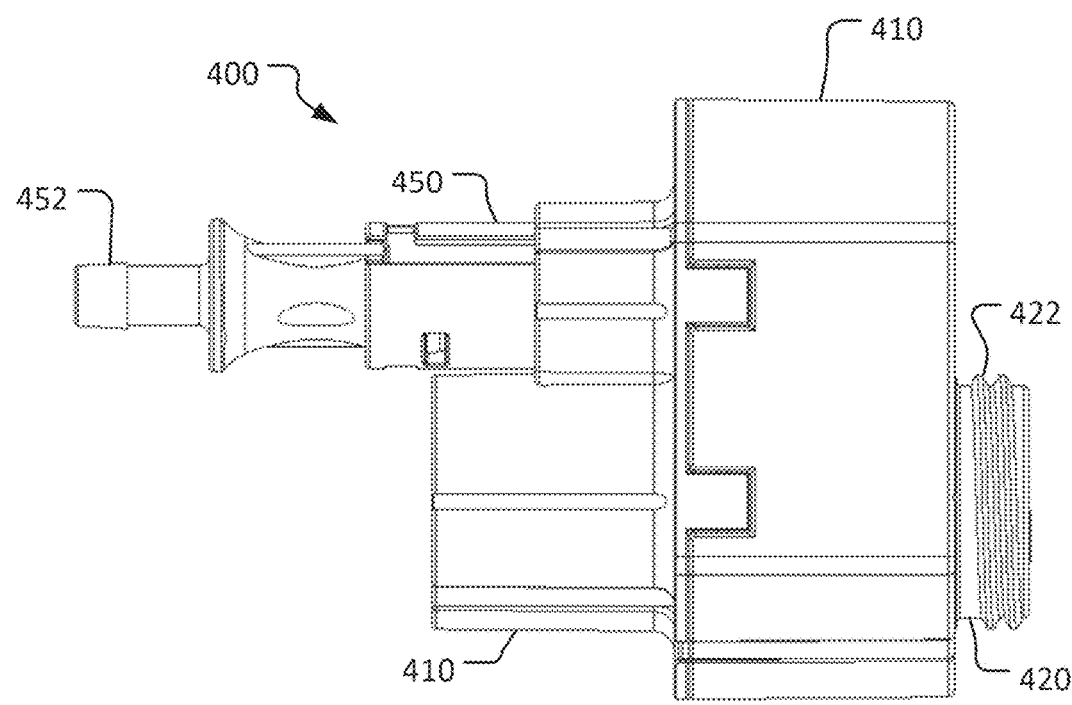
FIG. 14 is a longitudinal side view of the fluid coupling portion of FIG. 13.
Figure 15:
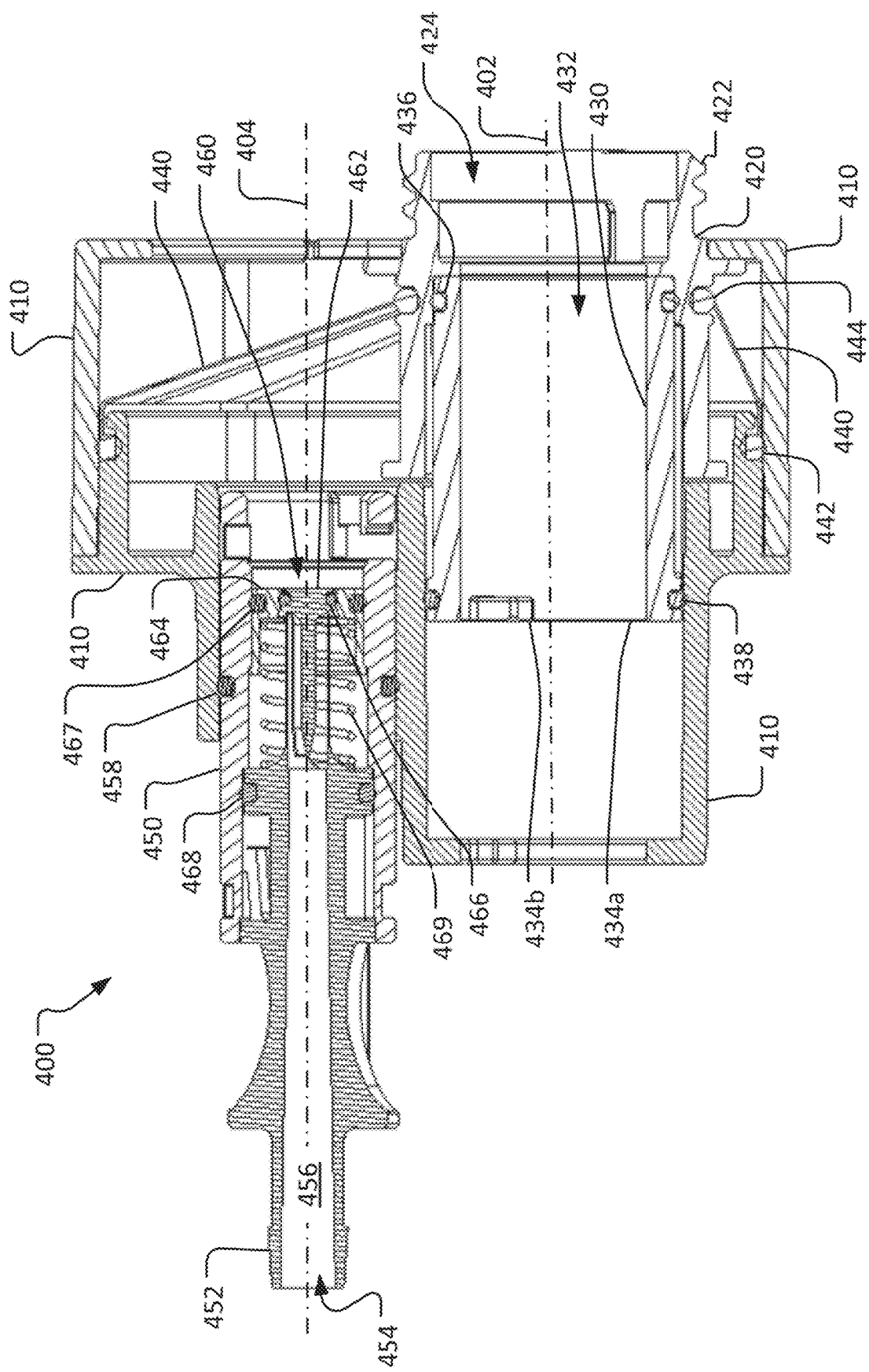
FIG. 15 is a longitudinal cross-sectional side view of the fluid coupling portion of FIG. 13.

Referring to FIGS. 13-15, a second coupling portion 400 can be configured to releasably mate with the first coupling portion 300 described above. As described further below, the coupling portions 300 and 400 provide a repeatably connectable aseptic fluid coupling system. In other words, the coupling portions 300 and 400 (when previously sterilized) can be connected to establish a sterile fluid flow path therethrough, and coupling portions 300 and 400 can thereafter be disconnected and reconnected multiple times such that the sterile fluid flow path is repeatably established. That sterile fluid flow path can be repeatably established through the coupling portions 300 and 400 even though the coupling portions 300 and 400 are disconnected and reconnected multiple times in a non-sterile environment.

In the depicted embodiment, the second coupling portion 400 includes a housing 410, a connection member 420, a sleeve 430, a flexible member 440, a valve body 450, and a valve member 460. The housing 410 defines a first longitudinal axis 402 and a second longitudinal axis 404. In the depicted embodiment, the first longitudinal axis 402 is parallel with the second longitudinal axis 404. The parallelism between the axes 402 and 404 is not required in all embodiments.

The connection member 420 can be movably coupled with the housing 410. In the depicted embodiment, the connection member 420 is slidably coupled with the housing 410. In particular (as described further below), the connection member 420 can translate laterally between a first position (as shown) that is coaxial with the first longitudinal axis 402 and a second position (e.g., FIGS. 25-30) that is coaxial with the second longitudinal axis 404. The connection member 420 can translate along a path that is transverse to one or both of the axes 402 and 404. In the depicted embodiment, the connection member 420 can translate along a path that is orthogonal to the axes 402 and 404.

The connection member 420 includes a connection structure 422 that is configured to releasably mate with the connection structure 130 of the fluid coupling device 100 (e.g., FIGS. 1-3). In the depicted embodiment, connection structures 130 and 422 are threaded members that can releasably mate with each other. In some embodiments, the connection structures 130 and 422 include other types of connection mechanisms such as, but not limited to, a snap connection, a thumb latch connection, a bayonet-style connection, a luer connection, a luer-lock connection, and the like, and combinations thereof.

The connection member 420 defines a connection member bore 424. In the depicted embodiment, the sleeve 430 is located within the connection member bore 424. The sleeve 430 is slidably engageable within the connection member 420. While the sleeve 430 is engaged with the connection member 420 (as shown), the sleeve 430 mechanically interferes with the connection member 420 such that the connection member 420 cannot move from the first position (as shown) that is coaxial with the first longitudinal axis 402.

As described further below, the sleeve 430 can be moved away from the connection member 420 such that the sleeve 430 becomes disengaged from the connection member 420. For example, in the depicted embodiment the sleeve 430 can be slidably translated (to the left in FIG. 15) along the first longitudinal axis 402 away from the connection member 420. When the sleeve 430 has been disengaged from the connection member 420, in some embodiments the connection member 420 is free to be moved from the first position that is coaxial with the first longitudinal axis 402 toward the second position that is coaxial with the second longitudinal axis 404.

The sleeve 430 defines a sleeve bore 432. The sleeve bore 432 can be configured to receive the cap 200 (FIGS. 4-12). The sleeve 430 can include features to releasably mate with the cap 200. For example, in the depicted embodiment the sleeve 430 includes a first projection 434a and a second projection 434b that extend within the sleeve bore 432. The first projection 434a and the second projection 434b can releasably mate with the slots 232a and 232b of the cap 200. While in the depicted embodiment projections and slots are used as the features whereby the sleeve 430 and the cap 200 can releasably mate with each other, in some embodiments other types of features can be included. Such features can include, but are not limited to, threads, snap-together connections, bayonet-style connections, compression connections, and the like, and combinations thereof.

The sleeve 430 may include one or more seals. For example, in the depicted embodiment the sleeve 430 includes a first seal 436 that can slidably engage with the bore 424 of the connection member 420 and/or the housing 410, and a second seal 438 that slidably engages with the housing 410. The seals 436 and 438 can extend around the entire periphery of the sleeve 430. As described further below, the seals 436 and 438 can provide sterility barriers and/or isolation barriers between sterile areas/surfaces and non-sterile areas/surfaces.

The second coupling portion 400 can also include the flexible member 440. The flexible member 440 acts as a seal that provides a sterility/isolation barrier between particular regions interior to the coupling portion 400, and regions external to the coupling portion 400. Moreover, the flexible member 440 provides the seal while accommodating the aforementioned movement of the connection member 420 in relation to the housing 410. Accordingly, at least some portions of the flexible member 440 are extendable and contractible to accommodate the movement of the connection member 420. In some embodiments, the flexible member 440 is elastic or otherwise reconfigurable such that the flexible member 440 stretches to accommodate the movement of the connection member 420. In some embodiments, the flexible member 440 may include folds, pleats, bellows, spring members, and the like, to help accommodate the movement of the connection member 420.

In the depicted embodiment, the flexible member 440 includes an outer periphery 442 and an inner periphery 444. The outer periphery 442 is affixed to the housing 410. The inner periphery 444 is affixed to the connection member 420.

The flexible member 440 can be made of any suitable material. For example, the flexible member 440 can be made of materials such as, but not limited to, silicone, ePTFE, EPDM, urethane, fluorosilicone, neoprene, nitrile, latex, and the like, and combinations thereof.

The second coupling portion 400 can also include the valve body 450 that houses the valve member 460. The valve body 450 includes an end portion 452 that defines an end port 454. As with the end portion 112 described above, end portion 452 can be configured for any suitable type of connection. Accordingly, end portion 452 may have various configurations such as, but not limited to, a barbed fitting (as shown), a luer fitting, a compression fitting, a threaded fitting (internal or external), a sanitary fitting, a pigtail, a T-fitting, a Y-fitting, a bag fitment, and any other suitable type of configuration such that the coupling portion 400 is suitable for connection to a fluid system as desired. In some embodiments, the second coupling portion 400 may be supplied with a removable cap (not shown) that is releasably coupled with the end portion 452, and that covers end port 454.

The valve body 450 defines a fluid pathway 456 that terminates at the end port 454. In the depicted embodiment, the patency of the fluid pathway 456 is determined by the positions of the components of the valve member 460 in relation to the valve body 450. That is, the components of the valve member 460 can move in relation to the valve body 450 to open the fluid pathway 456 through the second coupling portion 400, or to close the fluid pathway 456 through the second coupling portion 400. In the depicted arrangement of the components of the valve member 460, the fluid pathway 456 is occluded by the valve member 460. As described further below, while the connection member 420 is coaxial with the second longitudinal axis 404, and while the first coupling portion 300 and the second coupling portion 400 are mated together, the valve member 460 can engage with the valve member 120 (FIG. 3) to open a fluid pathway between end ports 114 and 454. In that manner a sterile fluid pathway can be established through both of the first coupling portion 300 and the second coupling portion 400, while the coupling portions 300 and 400 are mated together.

In the depicted embodiment, the valve member 460 includes a center stem 462, a spring-loaded movable valve sleeve 464, and a spring 469. In the illustrated arrangement, the valve member 460 is oriented in a closed position in which the valve member 460 provides a fluidic-sealed occlusion of the fluid pathway 456. The valve sleeve 464 can be forced away from the end of the center stem 462 (i.e., to the left in FIG. 15) to allow fluid flow past the valve member 460. The spring member 469 is included, in the depicted embodiment, to bias the movable valve sleeve 464 to the closed position. Peripheral elastomeric seals 466, 467, and 468 (e.g., o-rings) are included such that the fluid pathway 456 is sealed closed while the valve member 460 is in the closed orientation.

In the depicted embodiment, the valve member 460 is a poppet valve. In some embodiments, other types of valve members 460 are alternatively or additionally used in the valve body 450. For example, in some embodiments the valve member 460 is a type of valve such as, but not limited to, a butterfly valve, a ball valve, a duckbill valve, a diaphragm valve, a needle valve, a pinch valve, a plug valve, and the like.

In some embodiments, the valve body 450 is movable in relation to the housing 410. In the depicted embodiment, the valve body 450 can be slidably translated along the second longitudinal axis 404. For example, in the depicted embodiment the valve body 450 can be slidably translated (to the right in FIG. 15) along the first longitudinal axis 402 generally toward the connection member 420.

In the depicted embodiment, the valve body 450 is physically prevented (blocked) from being translated longitudinally toward the connection member 420 unless the connector member 420 is coaxial with the valve body 450. That is, unless the connection member 420 is in its second position (coaxial with the second longitudinal axis 404), the valve body 450 cannot move from its position as shown in FIG. 15.

The valve body 450 may include one or more seals. For example, in the depicted embodiment the valve body 450 includes a seal 458 that can slidably engage with the housing 410. The seal 458 can extend around the entire periphery of the valve body 450. As described further below, the seal 458 can provide sterility/isolation barriers between sterile areas/surfaces and non-sterile areas/surfaces.

In some embodiments, the materials from which the components of the second coupling portion 400 are made of include thermoplastics. In particular embodiments, the materials from which the components of the second coupling portion 400 are made of are thermoplastics, such as, but not limited to, polycarbonate, polysulfone, polyether ether ketone, polysulphide, polyester, polyphenylene, polyaryletherketone, and the like, and combinations thereof. In some embodiments, the second coupling portion 400 is metallic-free. That is, in some embodiments no metallic materials are included in the second coupling portion 400. For example, in some embodiments no metallic springs are included in the second coupling portion 400. Alternatively, in some embodiments the spring member 469 is a metallic spring (e.g., spring steel, stainless steel, and the like). In some embodiments, the seals (e.g., seal 436 et al.) are made of materials such as, but not limited to, silicone, fluoroelastomers (FKM), ethylene propylene diene monomer (EPDM), and the like.

In some implementations, the assembled coupling portion 400 (and the other coupling portions described herein) is sterilized prior to use (e.g., using any suitable sterilization method such as gamma sterilization, ethylene oxide sterilization, e-beam sterilization, Noxilizer™ sterilization, Revox® sterilization, or using an autoclave, and the like). In some cases during the sterilization, a cap (not shown) may be included on the end portion 452 to seal the end port 454. In some cases the assembled coupling portion 400 may be coupled with tubing and/or other components prior to sterilization, and the assembly is sterilized in the coupled configuration.

As described further below, in some embodiments portions of the second coupling portion 400 are sterile, while other portions of the second coupling portion 400 are non-sterile. For example, in some embodiments at least valve member 460 and fluid pathway 456 are sterile, whereas at least some other portions of the second coupling portion 400 (e.g., connection structure 422) are non-sterile.

FIGS. 16-30 illustrate a sequential process of connecting the first coupling portion 300 with the second coupling portion 400 so as to establish a sterile/isolated fluid pathway therethrough (between end ports 114 and 454). Thereafter, to disconnect the first coupling portion 300 from the second coupling portion 400, the process can be reversed. It should be understood that the steps for the connection and disconnection processes are described primarily in relation to a particular example embodiment (the first coupling portion 300 with the second coupling portion 400), and that variations of the steps are also envisioned within the scope of this disclosure.

The coupling portions 300 and 400 (and the other coupling portions of the other coupling embodiments described herein) are designed to be functionally interchangeable coupling portions. For example, the coupling portion 300 is designed such that it can be coupled with two or more of the coupling portions 400 (at individual times), if so desired. That is, the first coupling portion 300 may be coupled with a particular second coupling portion 400, then uncoupled, and then coupled with a different second coupling portion 400, and so on for still other second coupling portions 400 as desired. Likewise, the second coupling portion 400 may be coupled with a particular first coupling portion 300, then uncoupled, and then coupled with a different first coupling portion 300, and so on for still other first coupling portions 300 as desired. In each instance of coupling and uncoupling, the isolation from the surrounding environment of the fluids in the various coupling portions 300 and 400 can be maintained.

Referring to FIGS. 16-18, the first coupling portion 300 and the second coupling portion 400 can be selectively mated with each other, and unmated from each other. In the depicted embodiment, the cap 200 of the first coupling portion 300 can be inserted into the bores 424 and 432 of the connection member 420 and the sleeve 430 respectively (FIG. 15). The projections 434a and 434b can be oriented in alignment with the slots 232a and 232b (FIG. 4) to facilitate proper, full engagement between the first coupling portion 300 and the second coupling portion 400. To initiate the process of engaging the first coupling portion 300 and the second coupling portion 400, the connection structures 130 and 422 can be mated together. For example, in the depicted embodiment the connection structure 130 is rotated in relation to the housings 110 and 410 such that connection structure 130 is threaded into engagement with the connection structure 422.

In some implementations, the first coupling portion 300 and the second coupling portion 400 are each sterilized prior to use. That is, at least some interior regions/surfaces of the first coupling portion 300 and the second coupling portion 400 are sterile prior to mating the first coupling portion 300 and the second coupling portion 400 together. As described further below, the first coupling portion 300 and the second coupling portion 400 are configured such that the sterile regions/surfaces remain sterile throughout the processes of connecting and disconnecting the first coupling portion 300 and the second coupling portion 400.

In some implementations, the repeatable sterile fluid coupling system made up of the first coupling portion 300 mated with the second coupling portion 400 is configured to, for example, releasably connect a first fluid system equipment or container to a second fluid system equipment or container. In one non-limiting example, the repeatable sterile fluid coupling systems described herein can provide a reusable, aseptic connection and disconnection capability for a fluid path between a bioreactor system (e.g., connected directly to one coupling portion 300/400, or connected via a fluid tube) and a fluid container in the form of a media bag (e.g., connected directly to the other coupling portion 300/400, or connected via a fluid tube).

Figure 19:
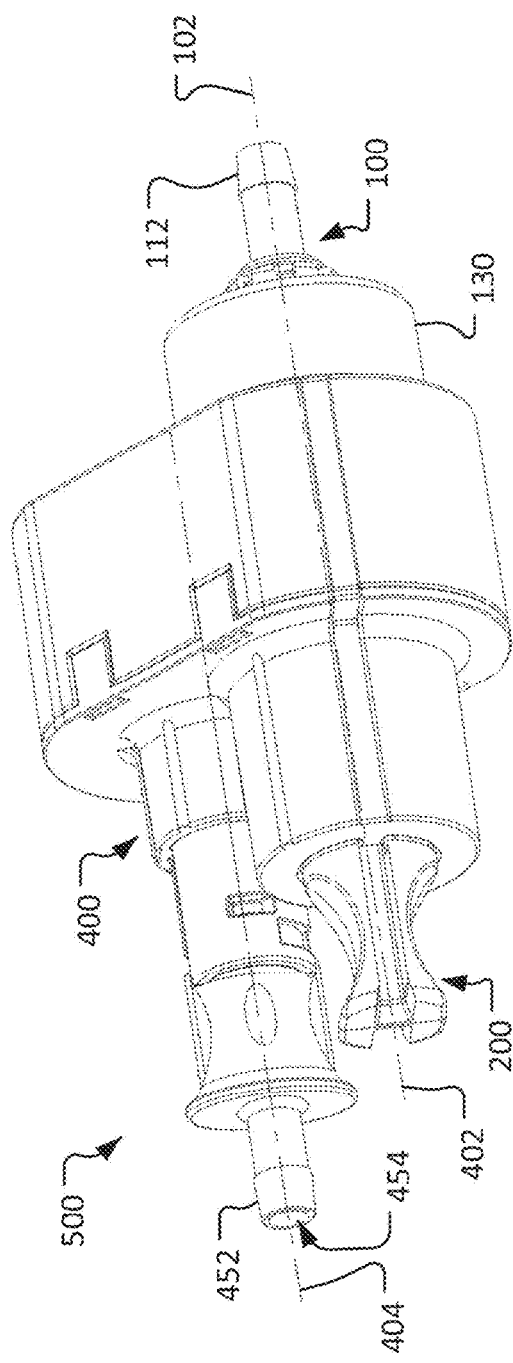
FIG. 19 is a perspective view of the repeatable sterile fluid coupling system of FIG. 16 in a first configuration.
Figure 21:
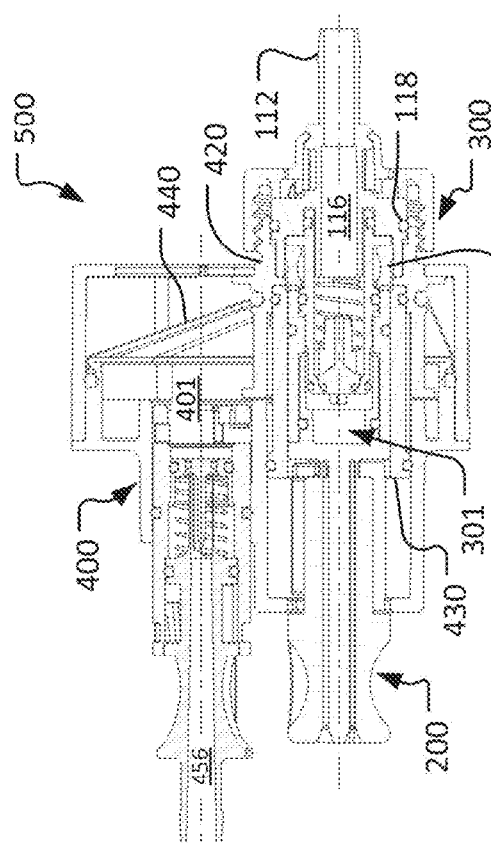
FIG. 21 is a longitudinal cross-sectional side view of the repeatable sterile fluid coupling system as configured in FIG. 19.
Figure 20:
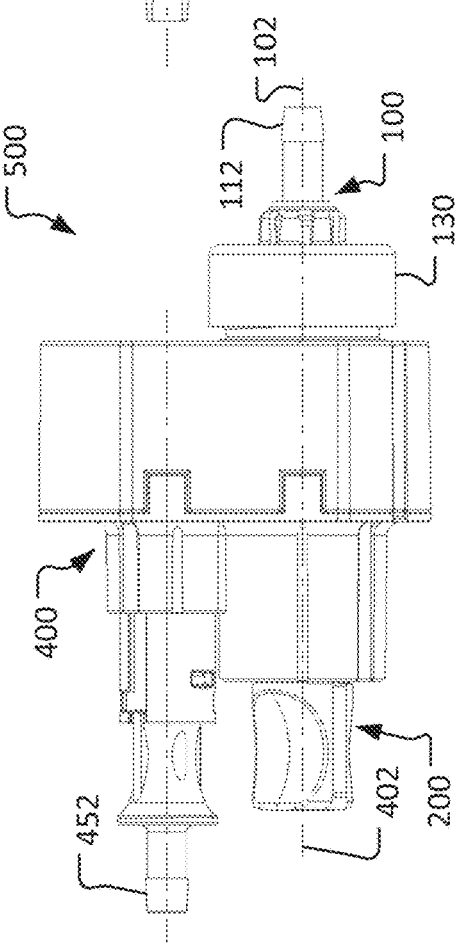
FIG. 20 is a longitudinal side view of the repeatable sterile fluid coupling system as configured in FIG. 19.

Referring to FIGS. 19-21, after completing the interconnection of the first coupling portion 300 and the second coupling portion 400 as described above, the depicted fluid coupling system 500 is arranged in the configuration as shown. In this arrangement, the longitudinal axis 102 of the first coupling portion 300 is coincident with the first longitudinal axis 402 of the second coupling portion 400. The seal 118 provides an airtight seal between the first coupling portion 300 and the second coupling portion 400. The sleeve 430 is positioned so as to restrict the movement of the connection member 420 away from the position shown (e.g., a translational movement of the connection member 420 and first fluid coupling portion 300 toward the second longitudinal axis 404).

As described above, the first coupling portion 300 and the second coupling portion 400 can be previously sterilized. Accordingly, the first coupling portion 300 can have a first sterile region 301, and the second coupling portion 400 can have a second sterile region 401. The sterile regions 301 and 401 are in addition to the sterile fluid pathways 116 and 456. The first sterile region 301 includes the spaces and surfaces between the cap 200 and the fluid coupling device 100. In some embodiments, the gasket 126 serves to seal the first sterile region 301 from the other, outer surfaces of the first coupling portion 300 that may be unsterile. The second sterile region 401, in general, includes the spaces and surfaces defined between the flexible member 440, the connection member 420, and the housing 410.

In the configuration as shown, the cap 200 is still engaged with the fluid coupling device 100. The second end 220 of the cap 200 is projecting out from the housing 410 of the second coupling portion 400. In this arrangement, the second end 220 is accessible to a user such that the cap 200 can be manipulated.

The next step in the process of coupling the first coupling portion 300 with the second coupling portion 400 to create a fluid flow pathway therethrough is to remove the cap 200 from the fluid coupling device 100. In the depicted embodiment, the cap 200 can be removed from the fluid coupling device 100 by first rotating the cap 200 and then pulling the cap 200 off from the fluid coupling device 100 along the first longitudinal axis 402. As the cap 200 is rotated and then pulled (by a user of the fluid coupling system 500), the projections 434a and 434b travel within the slots 232a and 232b. The projections 434a and 434b and slots 232a and 232b are configured to facilitate the desired movements of the cap 200 in relation to the first and second coupling portions 300/400, so as to properly remove the cap 200 from the fluid coupling device 100. As the cap 200 is pulled away from engagement with the fluid coupling device 100, the sleeve 430 will also travel with the cap 200.

Figure 22:
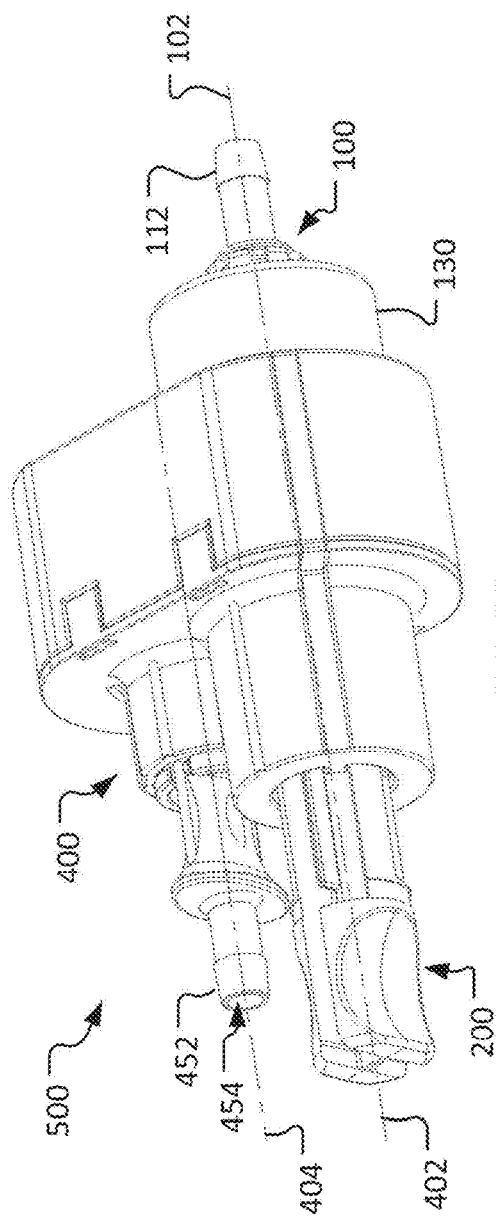
FIG. 22 is a perspective view of the repeatable sterile fluid coupling system of FIG. 16 in a second configuration.
Figure 24:
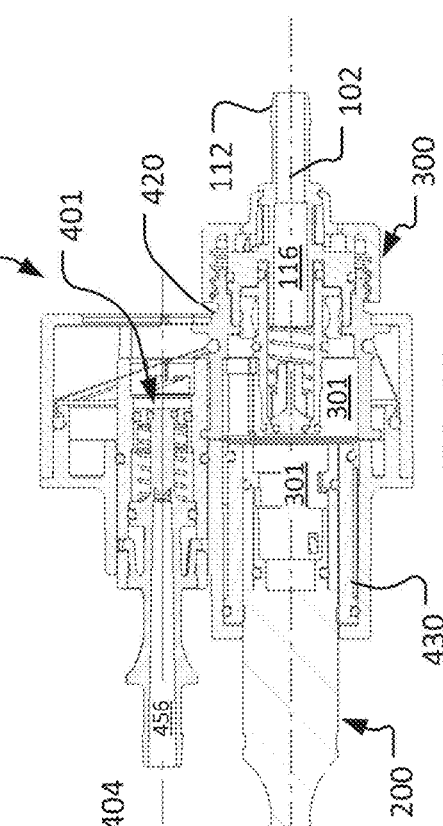
FIG. 24 is a longitudinal cross-sectional side view of the repeatable sterile fluid coupling system as configured in FIG. 22.
Figure 23:
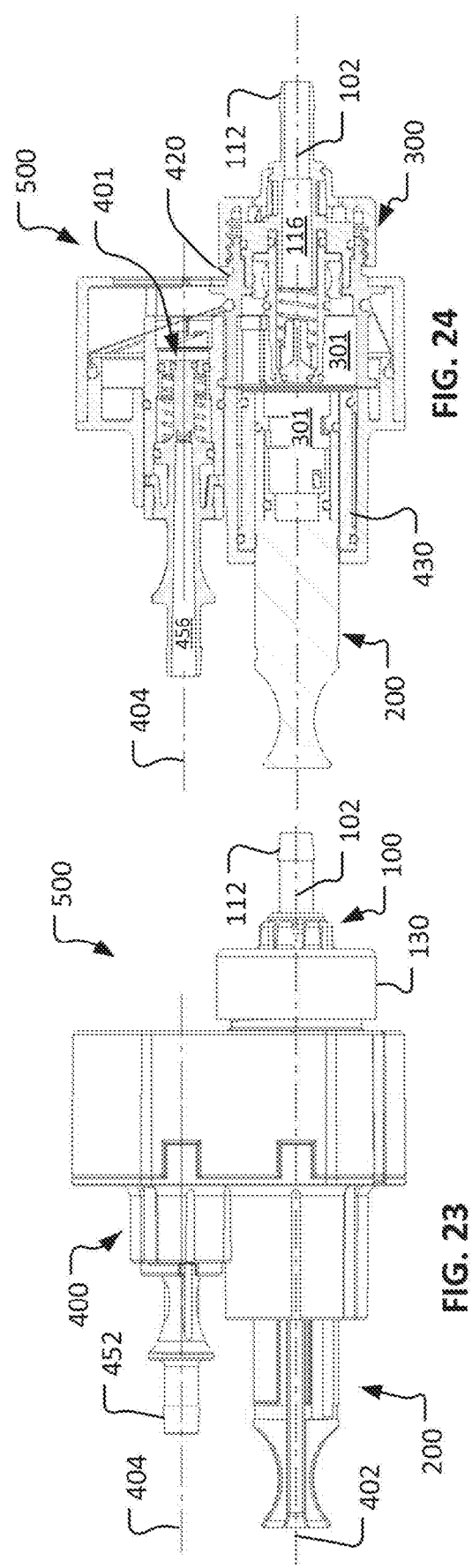
FIG. 23 is a longitudinal side view of the repeatable sterile fluid coupling system as configured in FIG. 22.

Referring to FIGS. 22-24, after completing the disengagement of the cap 200 from the fluid coupling device 100 as described above, the depicted fluid coupling system 500 is then arranged in the configuration as shown. The cap 200 and the sleeve 430 have been pulled away from engagement with the first coupling portion 300. Consequently, the sleeve 430 will no longer restrict the movement of the connection member 420 away from the connection member's first position that is coaxial with the first longitudinal axis 402. That is, with the sleeve 430 located in the position shown, the connection member 420 and the fluid coupling device 100 are free to be slid towards the second position of the connection member 420 where the connection member 420 is coaxial with the second longitudinal axis 404. It should be understood that until the connection member 420 is located in the second position where the connection member 420 is coaxial with the second longitudinal axis 404, the valve body 450 is physically restricted from moving from the orientation as shown.

Referring to FIGS. 25-27, after the user moves the connection member 420 and the fluid coupling device 100 to the connection member's second position that is coaxial with the second longitudinal axis 404, the depicted fluid coupling system 500 is then arranged in the configuration as shown. The sterile regions 301 and 401 are now in fluid communication with each other.

As the connection member 420 and the fluid coupling device 100 are moved between the first position that is coaxial with the first longitudinal axis 402 and the second position that is coaxial with the second longitudinal axis 404, the flexible member 440 conforms as needed to facilitate the movement, while maintaining a sterile barrier and/or isolation barrier.

While the connection member 420 and the fluid coupling device 100 are in the second position as shown, the longitudinal axis 102 of the fluid coupling device 100 is coincident with the second longitudinal axis 404. In that arrangement, the valve member 120 of the first coupling portion 300 is in alignment with the valve member 460 of the second coupling portion 400. Therefore, by moving the valve body 450 that houses the valve member 460 toward the valve member 120 of the first coupling portion 300, the two valve members 120 and 460 can engage with each other so that a fluid flow pathway is opened.

Referring to FIGS. 28-30, after the user moves the valve body 450 toward the valve member 120 of the first coupling portion 300, the two valve members 120 and 460 engage with each other to open a fluid flow pathway, and the depicted fluid coupling system 500 is then arranged in the configuration as shown.

As the two valve members 120 and 460 engage with each other, the center stem 462 of the valve member 460 makes face-to-face contact with the valve member 120. In addition, the spring-loaded movable valve sleeve 464 makes contact with a portion of the valve body 110 that surrounds the valve member 120. Such contact results in compression of spring member 122 and of spring member 469, and a sterile/isolated fluid flow pathway is opened between the end ports 114 and 454.

In the depicted embodiment, the user can push the valve body 450 toward the first coupling portion 300. As the valve body 450 is pushed by the user, the spring members 122 and 469 will become compressed and provide resistance to the pushing. The valve body 450 and the housing 410 can be configured to allow the valve body 450 to be releasably locked in relation to the housing 410 while the spring members 122 and 469 are compressed. For example, in the depicted embodiment, after pushing the valve body 450 toward the first coupling portion 300 along the longitudinal axis 404 so as to compress the spring members 122 and 469, the user can then twist the valve body 450 to lock the valve body 450 to the housing 410. In result, the user can release the valve body 450 and housing 410 and the sterile fluid flow pathway will remain open between end ports 114 and 454. In the depicted embodiment, a bayonet-style coupling is used to releasably lock the valve body 450 to the housing 410. In some embodiments, other types of mechanisms can be used to releasably lock the valve body 450 to the housing 410 such as, but not limited to, a pin/hole, a clip, a latch, a threaded connection, and the like, and combinations thereof.

While in the depicted embodiment the two valve members 120 and 460 are made to engage with each other by pushing the valve body 450 toward the first coupling portion 300, in some embodiments the engagement can be made by pushing the first coupling portion 300 (or portions thereof) toward the valve body 450. That is, in some embodiments the valve body 450 is fixed in relation to the housing 410, and the first coupling portion 300 is translatable along axes 102 and 404 when the first coupling portion 300 is in the second portion (where the two valve members 120 and 460 are coaxial).

With the fluid coupling system 500 arranged in the illustrated configuration, fluids can flow through the fluid coupling system 500 between the end ports 114 and 454. The fluid pathway between the end ports 114 and 454 is a sterile/isolated fluid pathway.

If desired, the fluid coupling system 500 can be uncoupled by following the reverse of the process described above for coupling the fluid coupling system 500. As the fluid coupling system 500 is uncoupled (such that the first coupling portion 300 is separated from the second coupling portion 400), the sterility/isolation of the first sterile region 301 and the second sterile region 401 is maintained. For example, as part of the process for separating the first coupling portion 300 from the second coupling portion 400, the cap 200 is reinstalled on the fluid coupling device 100, and the coupling portions 300 and 400 are configured as shown in FIGS. 16-18 once again. Thereafter, if desired, the fluid coupling system 500 can be recoupled by following the process described above for coupling the fluid coupling system 500. Once again, a sterile/isolated fluid pathway between the end ports 114 and 454 will be established. One of skill in the art will recognize that the repeatable, aseptic fluid coupling system 500 can be connected, disconnected, reconnected, and so on, for multiple cycles. In each case, while the first coupling portion 300 is connected to the second coupling portion 400 as shown in FIGS. 28-30, a sterile/isolated fluid pathway between the end ports 114 and 454 exists.

Figure 31:
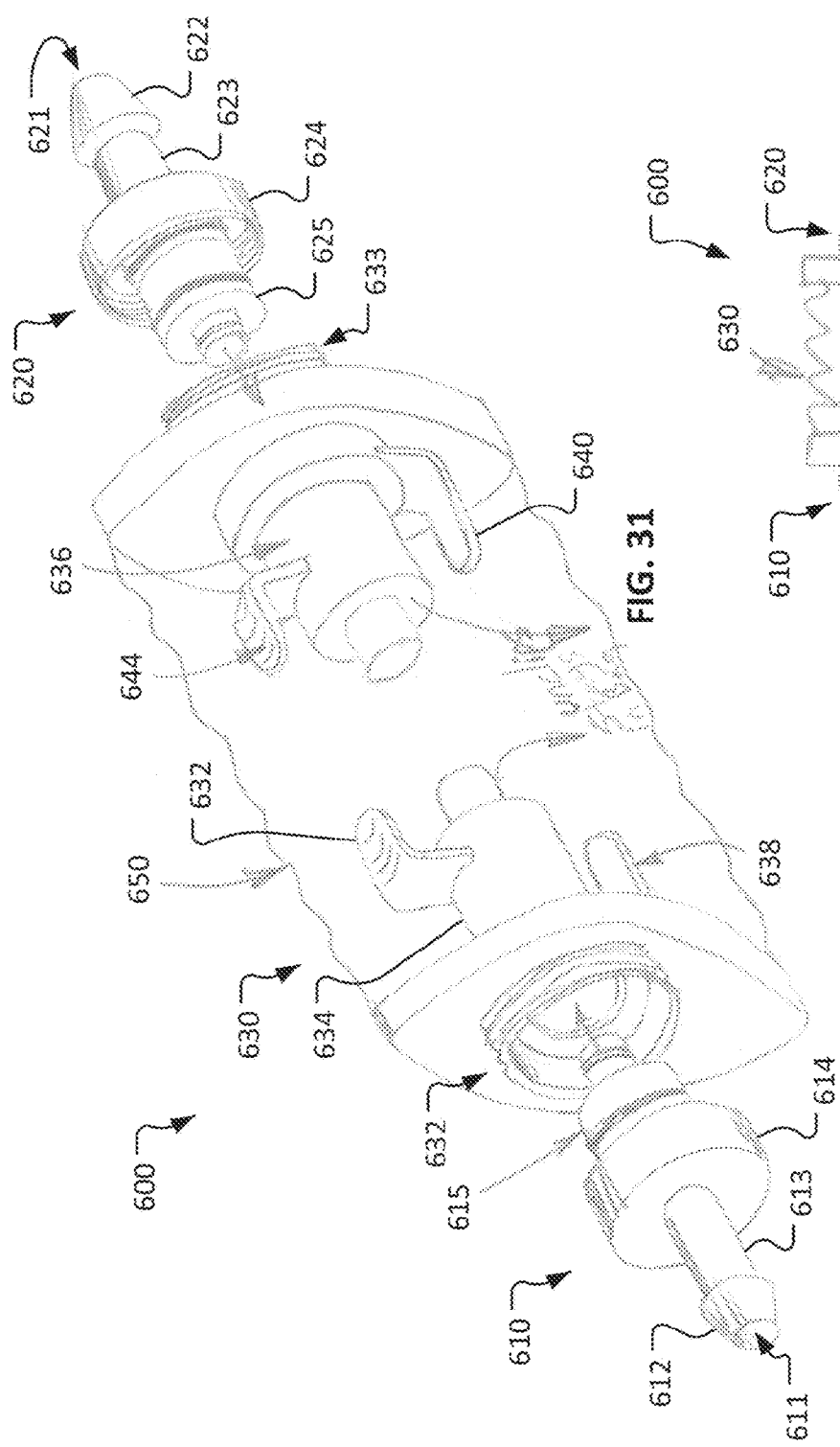
FIG. 31 is a perspective view of another example repeatable sterile fluid coupling system in accordance with some embodiments. The repeatable sterile fluid coupling system is in an uncoupled configuration.

Referring to FIG. 31, another example fluid coupling system 600 can provide an aseptic/isolated fluid connection that can be coupled and uncoupled multiple times. The fluid coupling system 600 includes a first end fluid coupling portion 610, a second end fluid coupling portion 620, and a middle fluid coupling portion 630. The first end fluid coupling portion 610 can be releasably connected to a first end 632 of the middle fluid coupling portion 630, and the second end fluid coupling portion 620 can be releasably connected to a second end 633 of the middle fluid coupling portion 630. As described further below, the fluid coupling system 600, in its fully connected configuration (FIG. 32), establishes a sterile/isolated fluid pathway between a first end port 611 and a second end port 621.

In some embodiments, such as the depicted embodiment, the first end fluid coupling portion 610 and the second end fluid coupling portion 620 are configured the same as each other. Alternatively, in some embodiments the first end fluid coupling portion 610 and the second end fluid coupling portion 620 can be configured differently from each other. For example, while each of the end fluid coupling portions 610 and 620 are depicted as having a barbed connection 612 and 622, in some embodiments one or both of connections 612 and 622 have other types of configurations such as, but not limited to, a luer fitting, a compression fitting, a threaded fitting (internal or external), a sanitary fitting, a pigtail, a T-fitting, a Y-fitting, a bag fitment, and any other suitable type of configuration such that the fluid coupling system 600 is suitable for connection to a fluid system as desired.

In the depicted embodiment, each of the fluid coupling portions 610 and 620 also include a valve body 613 and 623 respectively, a connection structure 614 and 624 respectively, and a cap 615 and 625 respectively. The caps 615 and 625 are selectively coupleable with the valve bodies 613 and 623 respectively. In the illustration, portions of the valve bodies 613 and 623 are obscured from view by the caps 615 and 625 respectively. The portion of the valve bodies 613 and 623 that are obscured from view house valve members (e.g., in some embodiments like valve members 120 and 460 of fluid coupling system 500 described above) that are configured to engage with each other as described further below.

While not shown, it should be understood that in some embodiments each end fluid coupling portion 610 and 620 may include a removable end cap (not shown), or another type of component, that is coupled to the connections 612 and 622 respectively. The fluid coupling portions 610 and 620 with end caps or other types of components coupled to the connections 612 and 622 may be sterilized so that the fluid pathways and valve members within each end fluid coupling portion 610 and 620 are sterile (in a manner analogous to that of first coupling portion 300 as described above).

In some embodiments, such as the depicted embodiment, the middle fluid coupling portion 630 includes a first cap trap 634, a second cap trap 636, a first cap trap release 638, a second cap trap release 640, a first cap release 642, and a second cap release 644. The middle fluid coupling portion 630 can also include a flexible housing 650 defining an enclosure in which the cap traps 634 and 636 are disposed.

In the depicted embodiment, the flexible housing 650 is deformable by the manipulations of a user of the fluid coupling system 600. In some embodiments, the flexible housing 650 is configured as a bag-like member. The material of the flexible housing 650 (or portions thereof) can be transparent or semi-transparent and flexible to allow for manual manipulation of the components housed within the flexible housing 650. The material of the flexible housing 650 is also suitable for sterilization (e.g., gamma sterilization, autoclave, EtO, e-beam, etc.). For example, in some embodiments the material of the flexible housing 650 (or portions thereof) is polyester, and other suitable materials. The ends 632 and 633 can be coupled to the flexible housing 650 so that the connection structures of the ends 632 and 633 are accessible on the exterior of the flexible housing 650. As described further below, the flexible housing 650 is deformable so that the user can move the ends 632 and 633 toward each other to couple the fluid coupling portions 610 and 620 together within the flexible housing 650.

The first cap trap release 638 can be activated to release the first cap trap 634 from engagement with the first end 632. The second cap trap release 640 can be activated to release the second cap trap 636 from engagement with the second end 633. The first cap release 642 can be activated to release the first cap 615 from engagement with the first cap trap 634. The second cap release 644 can be activated to release the second cap 625 from engagement with the second cap trap 636.

In some embodiments, the process for connecting the fluid coupling system 600 to create a sterile fluid pathway between the first end port 611 and the second end port 621 is as follows. The user can connect the first end fluid coupling portion 610 and the second end fluid coupling portion 620 to the first end 632 and the second end 633 of the middle fluid coupling portion 630 respectively (or, in some embodiments, in the opposite relationship if so desired). In doing so, the caps 615 and 625 become releasably locked inside of the first cap trap 634 and the second cap trap 636 respectively. Then, the user can manipulate the first cap trap release 638 and the first cap trap 634 through the flexible housing 650 such that the first cap trap 634 (with the first cap 615 locked therein) becomes unlocked and removed from the first end 632. The first cap trap 634 (with the first cap 615 locked therein) can be released by the user and allowed to remain loose within the flexible housing 650. Next, the user can manipulate the second cap trap release 640 and the second cap 636 through the flexible housing 650 such that the second cap trap 636 (with the second cap 625 locked therein) becomes unlocked and removed from the second end 633. The second cap trap 636 (with the second cap 625 locked therein) can be released by the user and allowed to remain loose within the flexible housing 650.

By removing the caps 615 and 625, the sterile portions of the first end fluid coupling portion 610 and the second end fluid coupling portion 620 are exposed within the sterile confines of the flexible housing 650. For example, the valve member contained in each of the first end fluid coupling portion 610 and the second end fluid coupling portion 620 are exposed within the sterile confines of the flexible housing 650.

Figure 32:
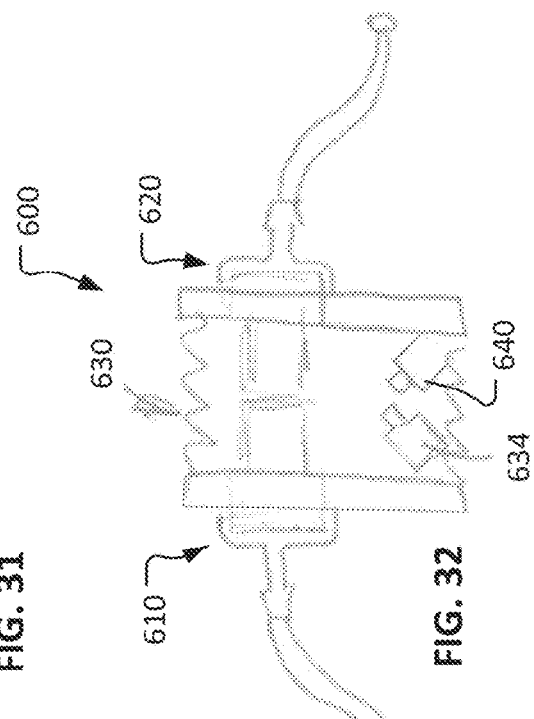
FIG. 32 is a side view of the repeatable sterile fluid coupling system of FIG. 31 in a coupled configuration.

Referring also to FIG. 32, with the valve members of the coupling portions 610 and 620 exposed to each other within the sterile confines of the flexible housing 650, the user can move the first end fluid coupling portion 610 and the second end fluid coupling portion 620 toward each other and can couple the valve members together. The flexible housing 640 can flex and/or act like an accordion member to accommodate the movement of the coupling portions 610 and 620 into a coupled arrangement. With the coupling portions 610 and 620 in the coupled arrangement, a sterile fluid pathway between first end port 611 and second end port 621 of the fluid coupling system 600 is established. In some embodiments, the first cap trap 634 (with the first cap 615 locked therein) and the second cap trap 636 (with the second cap 625 locked therein) can remain loosely contained within the flexible housing 650. In some embodiments, the first cap trap 634 (with the first cap 615 locked therein) and the second cap trap 636 (with the second cap 625 locked therein) can be releasably coupled with respective receptacles located within the flexible housing 650 rather than being loosely contained therein. For example, posts (not shown) within the flexible housing 650 can be provided within the flexible housing 650 with which the first cap trap 634 (with the first cap 615 locked therein) and the second cap trap 636 (with the second cap 625 locked therein) can be engaged. Hence, in some embodiments the first cap trap 634 (with the first cap 615 locked therein) and the second cap trap 636 (with the second cap 625 locked therein) can be rigidly contained within the flexible housing 650.

To uncouple the fluid coupling system 600 from coupled arrangement shown in FIG. 32, the user can perform the following process steps. First, the user can uncouple the valve members of the coupling portions 610 and 620. Next, the user can engage the first cap trap 634 (with the first cap 615 locked therein) onto the first end fluid coupling portion 610 and the second cap trap 636 (with the second cap 625 locked therein) onto the second end fluid coupling portion 620. Next, the user can activate the first cap release 642 and then uncouple the first connection structure 614 from the first end 632 of the middle fluid coupling portion 630 (to attain the arrangement shown in FIG. 31). Likewise, the user can activate the second cap release 644 and then uncouple the second connection structure 624 from the second end 633 of the middle fluid coupling portion 630 (to attain the arrangement shown in FIG. 31). The caps 615 and 625 maintain the sterility of the sterile portions of the coupling portions 610 and 620 (e.g., the valve members). The cap traps 634 and 636 maintain the sterility of the sterile portions of the middle fluid coupling portion 630 (e.g., the interior surfaces of the flexible housing 650 and the exterior surfaces of the cap traps 634 and 636). Thereafter, the user can reconnect the components of the fluid coupling system 600 to reestablish a sterile fluid pathway between first end port 611 and second end port 621 if so desired.

One of skill in the art will recognize that the repeatable, aseptic fluid coupling system 600 can be connected, disconnected, reconnected, and so on, for multiple cycles. In each case, while the coupling portions 610 and 620 are connected within the middle fluid coupling portion 630 as shown in FIG. 32, a sterile/isolated fluid pathway between the end ports 611 and 621 exists.

Figure 33:
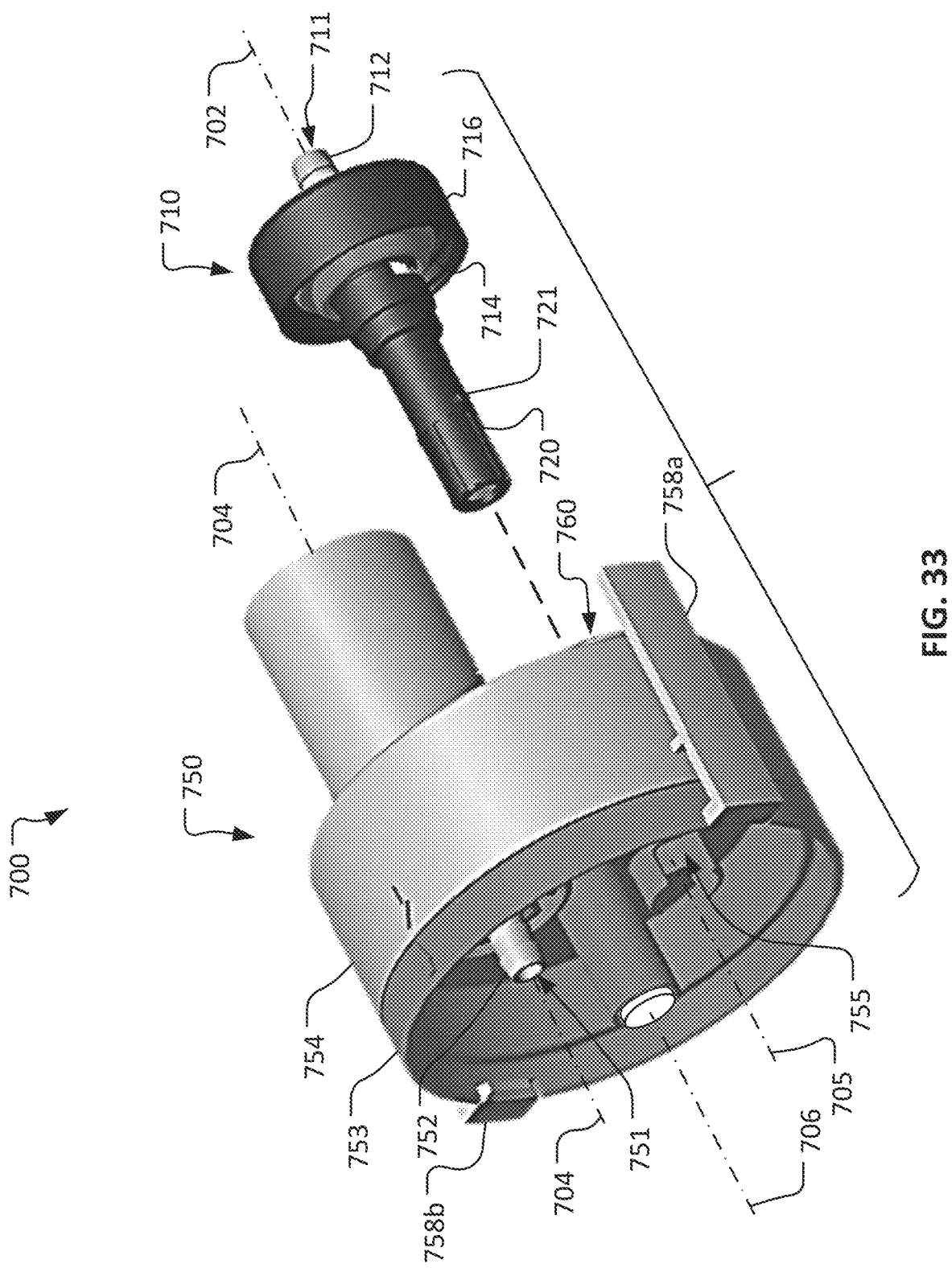
FIG. 33 is an exploded perspective view of another example repeatable sterile fluid coupling system in accordance with some embodiments.

Referring to FIG. 33, another example fluid coupling system 700 can provide an aseptic/isolated fluid connection that can be coupled and uncoupled for multiple cycles. The fluid coupling system 700 includes a first coupling portion 710 and a second coupling portion 750. The first coupling portion 710 can be releasably connected to the second coupling portion 750. In some implementations, prior to connecting the first coupling portion 710 to the second coupling portion 750, the coupling portions 710 and 750 are sterilized such that some inner regions and surfaces of the coupling portions 710 and 750 are sterile. As described further below, the fluid coupling system 700, in its fully connected configuration (FIGS. 40 and 41), can establish a sterile/isolated fluid pathway between a first end port 711 and a second end port 751.

In some embodiments, the first coupling portion 710 is configured with at least some of the same types of structural features as the first coupling portion 300 described above. For example, in the depicted embodiment the first coupling portion 710 includes an end portion 712, a valve body 714, a connection structure 716, and a cap 720, which are analogous to structural features of the first coupling portion 300. Therefore, structural features of the first coupling portion 710 can be any of the different types and variations of the analogous structural features described above regarding the first coupling portion 300. The materials of construction of the first coupling portion 710 can be any of the materials described above regarding the first coupling portion 300. As with the cap 200 of the first coupling portion 300, the cap 720 is removably coupled to the valve body 714.

The valve body 714 houses a first valve member 718 (not visible in this view; refer to FIG. 36) that, in some embodiments, can be analogous to valve member 120 described above. The first coupling portion 710 includes the connection structure 716 that is configured to selectively mate with a complementary connection structure of the second coupling portion 750. The first coupling portion 710 defines a longitudinal axis 702.

In the depicted embodiment, the second coupling portion 750 includes an inner housing portion 753 and an outer housing portion 754. As described further below, the inner housing portion 753 and the outer housing portion 754 are both longitudinally slidable in relation to each other, and rotatable in relation to each other. In particular, inner housing portion 753 and the outer housing portion 754 are rotatable in relation to each other about a central axis 706. The relative rotation and the longitudinal elongation between inner housing portion 753 and the outer housing portion 754 are releasably retained by a first latch 758a and a second latch 758b.

The second coupling portion 750 includes an end portion 752 and a valve body 756 that define a longitudinal axis 704. The valve body 756 houses a second valve member 757 (not visible in this view; refer to FIG. 36) that, in some embodiments, can be analogous to valve member 460 described above. The second coupling portion 750 includes the connection structure 760 that is configured to selectively mate with the complementary connection structure 716 of the first coupling portion 710.

The second coupling portion 750 includes a port 755 in which the first coupling portion 710 can be releasably received. The port 755 defines a longitudinal axis 705. When the first coupling portion 710 is engaged in the port 755 of the second coupling portion 750, the longitudinal axis 702 is coincident with the longitudinal axis 705.

In some embodiments, the materials from which the components of the fluid coupling system 700 are made of include thermoplastics. In particular embodiments, the materials from which the components of the fluid coupling system 700 are made of are thermoplastics, such as, but not limited to, polycarbonate, polysulfone, polyether ether ketone, polysulphide, polyester, polyvinylidene fluoride (PVDF), polyethylene, polyphenylsulfone (PP SU; e.g., Radel®), polyetherimide (PEI; e.g., Ultem®), polypropylene, polyphenylene, polyaryletherketone, and the like, and combinations thereof. In some embodiments, the materials from which one or more of the components of the fluid coupling system 700 are made of include metals such as, but not limited to stainless steel. In some embodiments, the fluid coupling system 700 is metallic-free. That is, in some embodiments no metallic materials are included in the fluid coupling system 700. For example, in some embodiments no metallic springs are included in the fluid coupling system 700. Alternatively, in some embodiments the spring member(s) is a metallic spring (e.g., spring steel, stainless steel, and the like). In some embodiments, the seals and/or gaskets are made of materials such as, but not limited to, silicone, fluoroelastomers (FKM), ethylene propylene diene monomer (EPDM), and the like.

FIGS. 34-41 illustrate a sequential process of connecting the first coupling portion 710 with the second coupling portion 750 so as to establish a sterile fluid pathway therethrough (between end ports 711 and 751). Thereafter, to disconnect the first coupling portion 710 from the second coupling portion 750, the process can be reversed. It should be understood that the steps for the connection and disconnection processes are described primarily in relation to a particular example embodiment (the first coupling portion 710 with the second coupling portion 750), and that variations of the steps are also envisioned within the scope of this disclosure.

Figure 34:
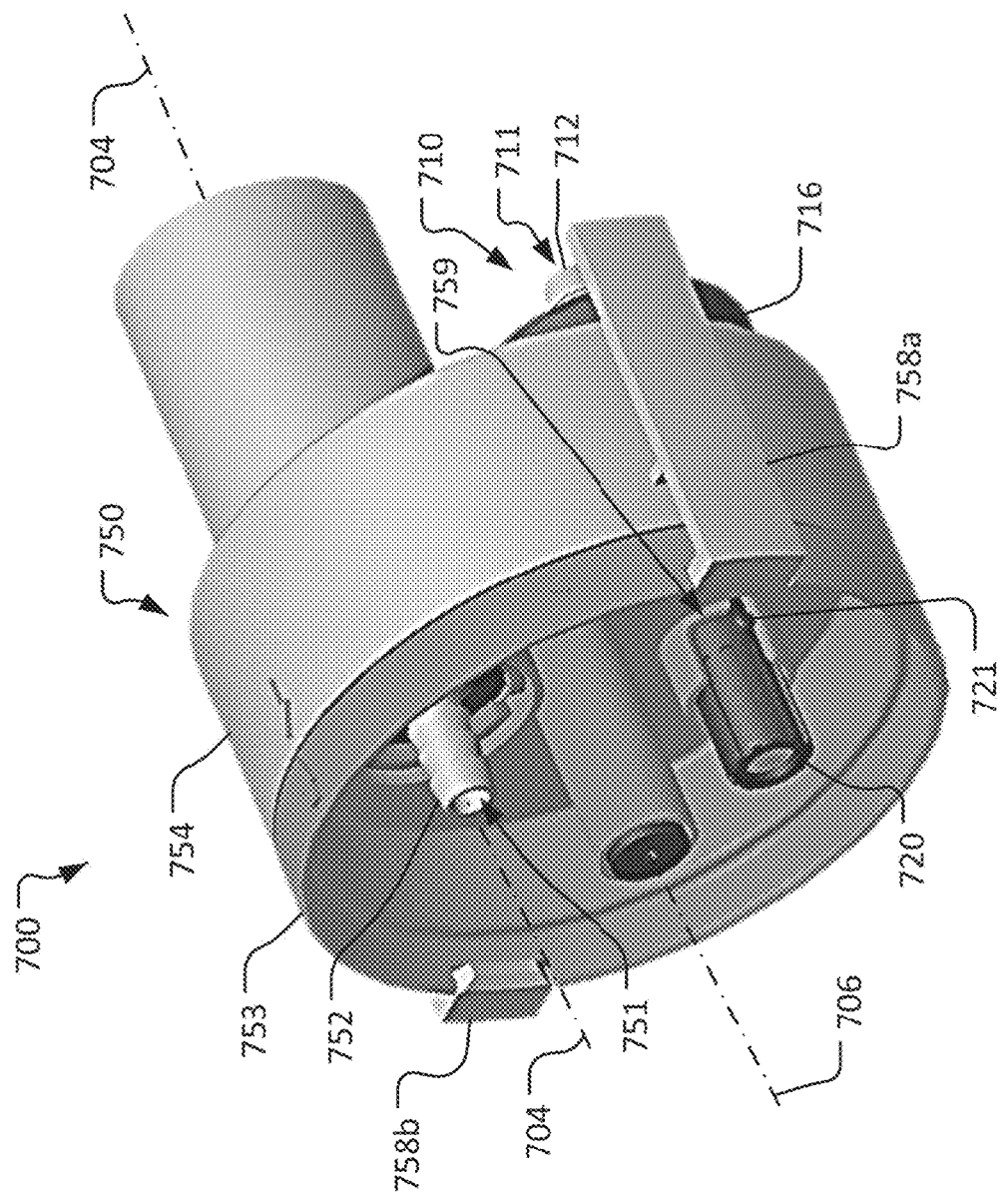
FIG. 34 is a perspective view of the repeatable sterile fluid coupling system of FIG. 33 in a first configuration.
Figure 35:
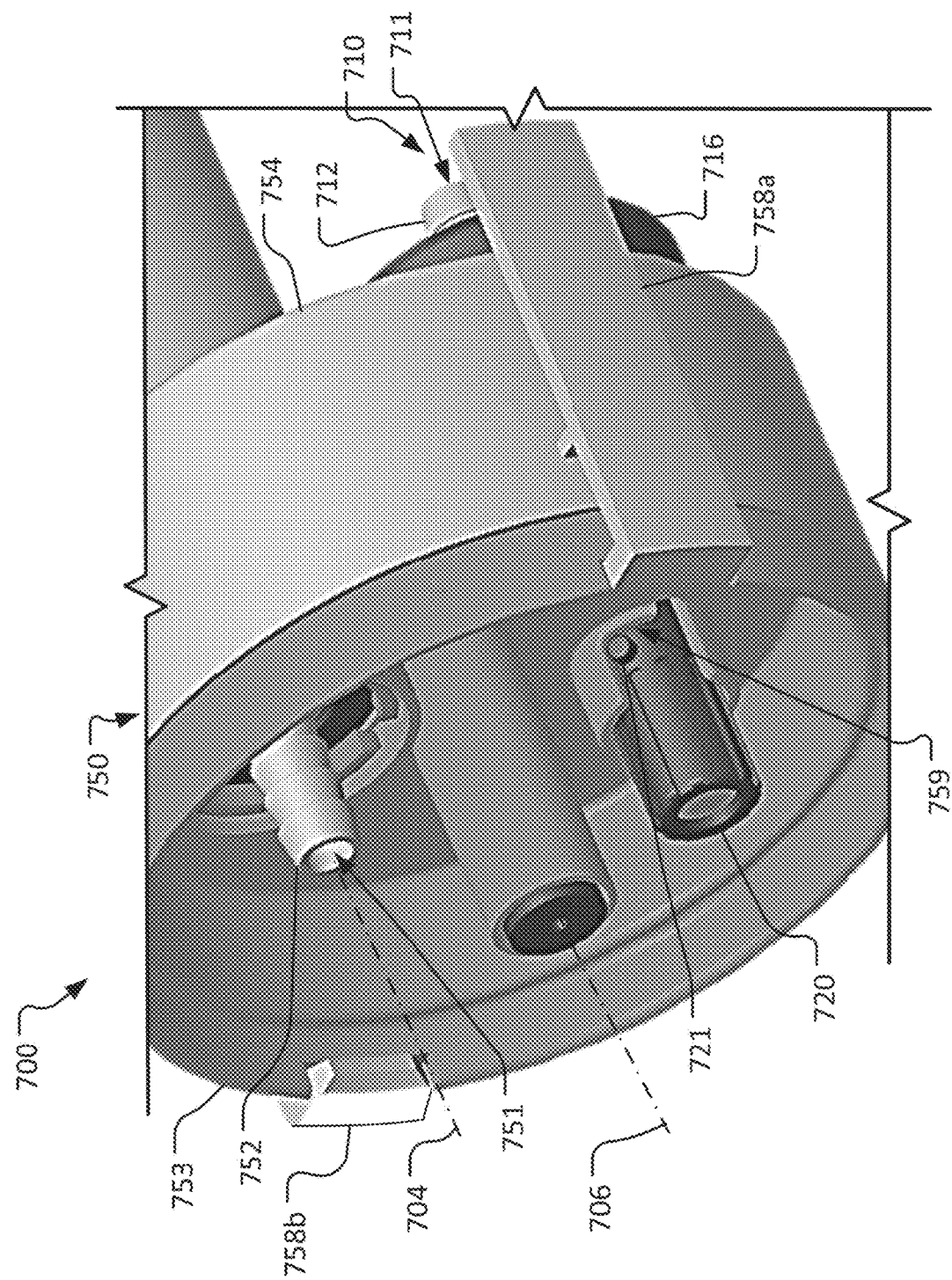
FIG. 35 is a partial perspective view of the repeatable sterile fluid coupling system of FIG. 33 in a second configuration.

Referring to FIGS. 34 and 35, a user of the fluid coupling system 700 can releasably engage the first coupling portion 710 with the second coupling portion 750. For example, a structural feature, such as a protrusion 721 on the cap 720, can be used to releasably engage the first coupling portion 710 with the second coupling portion 750. In the depicted embodiment, the protrusion 721 is mateable with a complementary structural feature 759 of the inner housing portion 753. In this example, the first coupling portion 710 can be releasably engaged with the second coupling portion 750 by pushing the first coupling portion 710 into engagement with the second coupling portion 750, and then rotating the first coupling portion 710 in relation to the second coupling portion 750. In doing so, the protrusion 721 on the cap 720 will become releasably engaged with the complementary structural feature 759 of the inner housing portion 753, resulting in engagement of the first coupling portion 710 with the second coupling portion 750.

Figure 36:
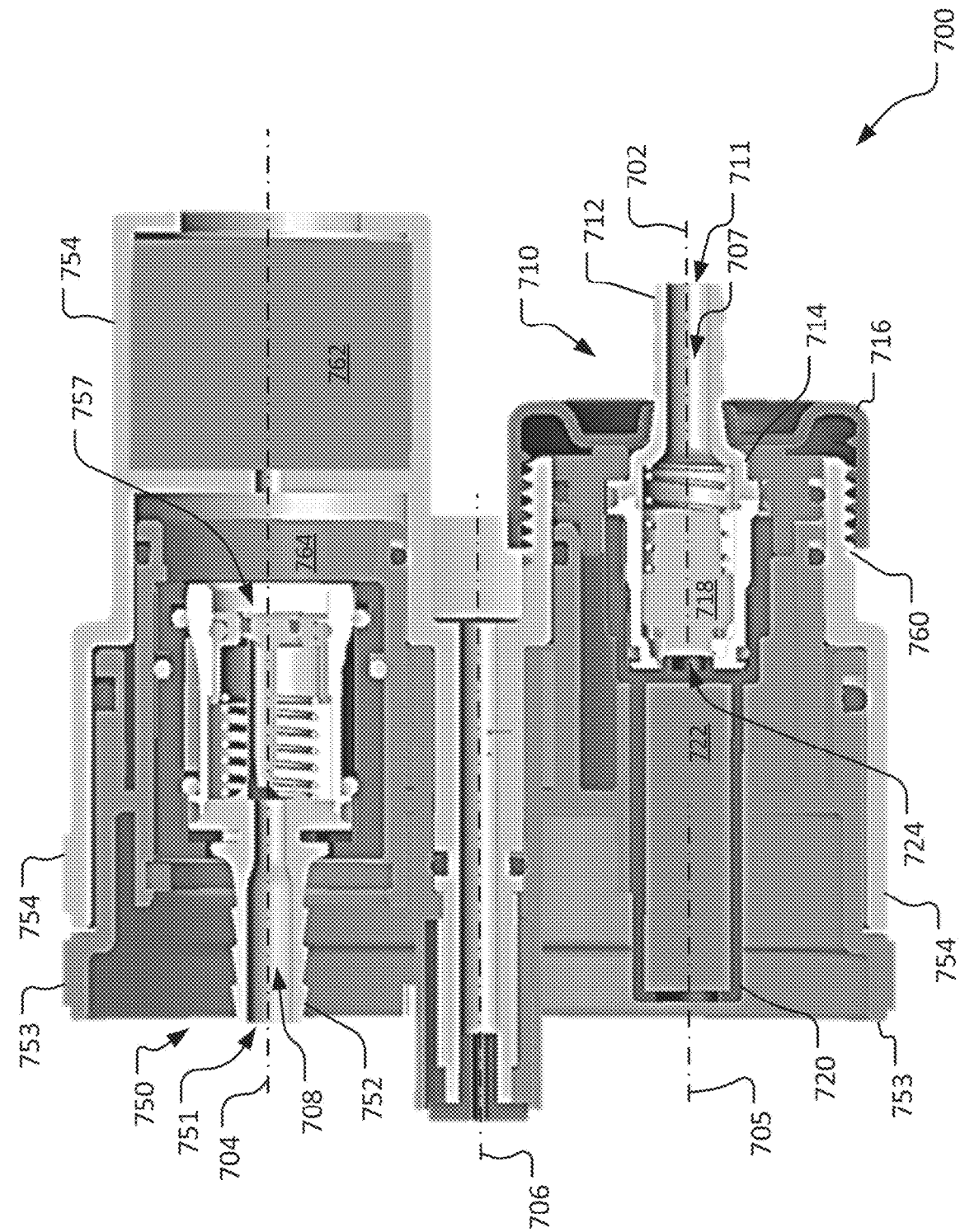
FIG. 36 is a longitudinal cross-sectional side view of the repeatable sterile fluid coupling system of FIG. 33 in the second configuration.

FIG. 36 provides a longitudinal cross-sectional view of the fluid coupling system 700 with the first coupling portion 710 in engagement with the second coupling portion 750. The valve members 718 and 757 of the first coupling portion 710 and the second coupling portion 750 respectively are visible. It can be seen that the valve members 718 and 757 are unaligned in relation to each other in the depicted configuration.

As described above, the first coupling portion 710 and the second coupling portion 750 can be previously sterilized. Accordingly, the first coupling portion 710 can have a first sterile region 724, and the second coupling portion 750 can have a second sterile region 764. The sterile regions 724 and 764 are sterile areas in addition to sterile fluid pathways 707 and 708. The first sterile region 724 includes the spaces and surfaces between the cap 720 and the valve body 714. The second sterile region 764, in general, includes the spaces and surfaces adjacent to the face of the second valve member 757. One or more seals and/or gaskets can be included to separate the sterile regions 724 and 764 from other regions that may be unsterile.

In the depicted embodiment, the first coupling portion 710 and the second coupling portion 750 include optional vents 722 and 762 respectively. Such vents may be included in any of the fluid coupling system embodiments described herein. The material of the vents 722 and 762 may allow for air/gas transmission while preventing through-flow (e.g., ingress) of bacteria and/or other contaminants. The material of the vents 722 and 762 can be porous and configured to allow the transmission of materials that are smaller than about 0.2 µm in size, while inhibiting the transmission of materials that are larger. In some embodiments, the filter media or porous element of the vents 722 and 762 inhibits the transmission of materials that are larger than about 0.1 or about 0.3 or about 0.4 or about 0.5 or larger than 0.5 while allowing the transmission of materials that are smaller.

As with the fluid coupling system 500 described above, the fluid coupling system 700 includes multiple seals and/or gaskets that act as barriers to isolate inner sterile regions of the fluid coupling system 700 from other unsterile regions, and/or as fluid flow seals.

Figure 37:
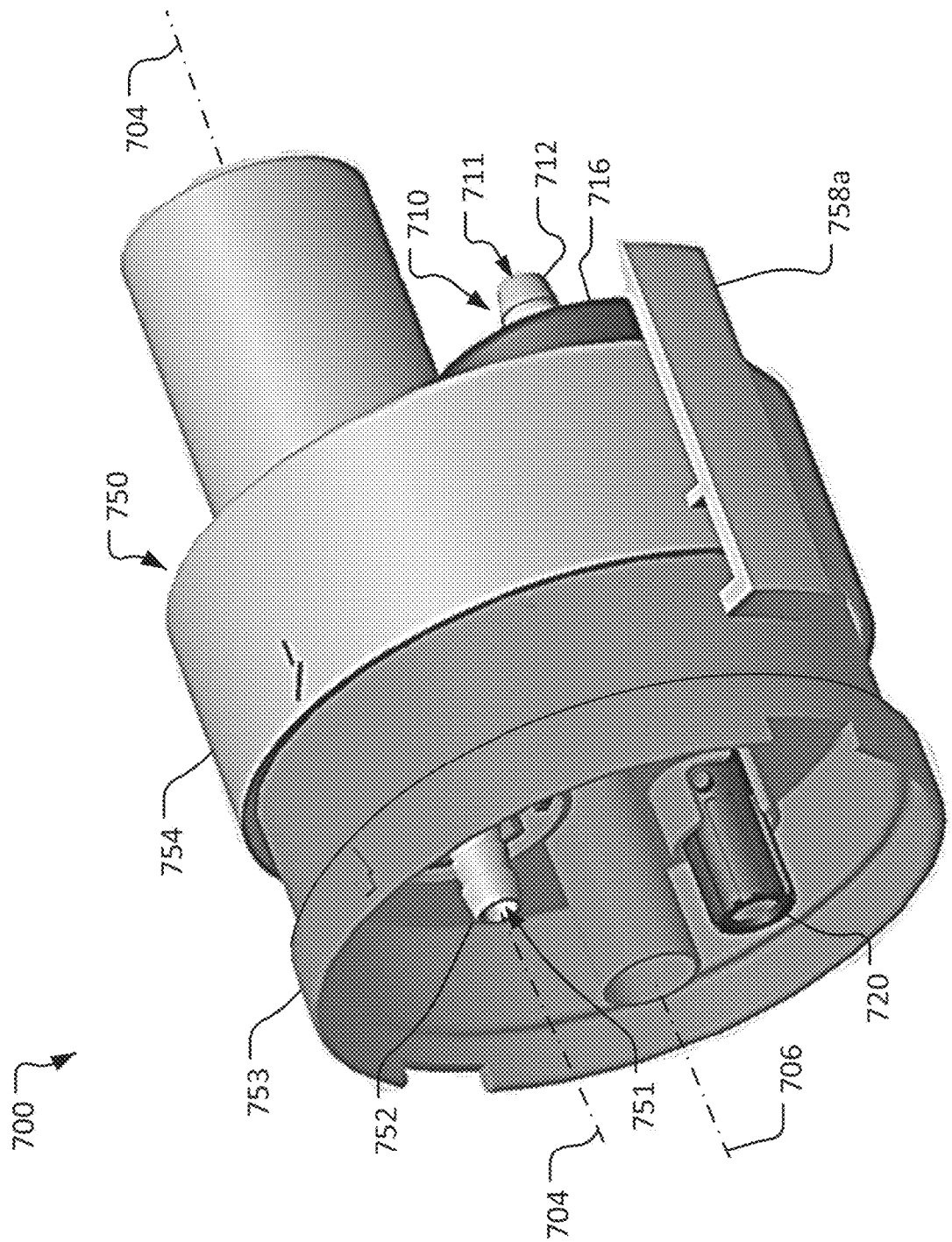
FIG. 37 is a perspective view of the repeatable sterile fluid coupling system of FIG. 33 in a third configuration.

Referring to FIG. 37, a user of the fluid coupling system 700 can longitudinally translate the inner housing portion 753 in relation to the outer housing portion 754. In essence, the longitudinal translation of the inner housing portion 753 in relation to the outer housing portion 754 is similar to a telescoping movement. Prior to performing the longitudinal translation, the user will deactivate any latch or coupling mechanism(s) between the inner housing portion 753 and the outer housing portion 754. For example, in the depicted embodiment, the user would deactivate the latches 758a and 758b. With the latches 758a and 758b decoupled from the inner housing portion 753, the user can then pull the inner housing portion 753 in relation to the outer housing portion 754 to result in the depicted configuration. Built in structural travel-stop features serve to limit the longitudinal elongation of the fluid coupling system 700.

As the inner housing portion 753 is longitudinally translated in relation to the outer housing portion 754, the cap 720 becomes removed and longitudinally separated from the rest of the first coupling portion 710.

Figure 38:
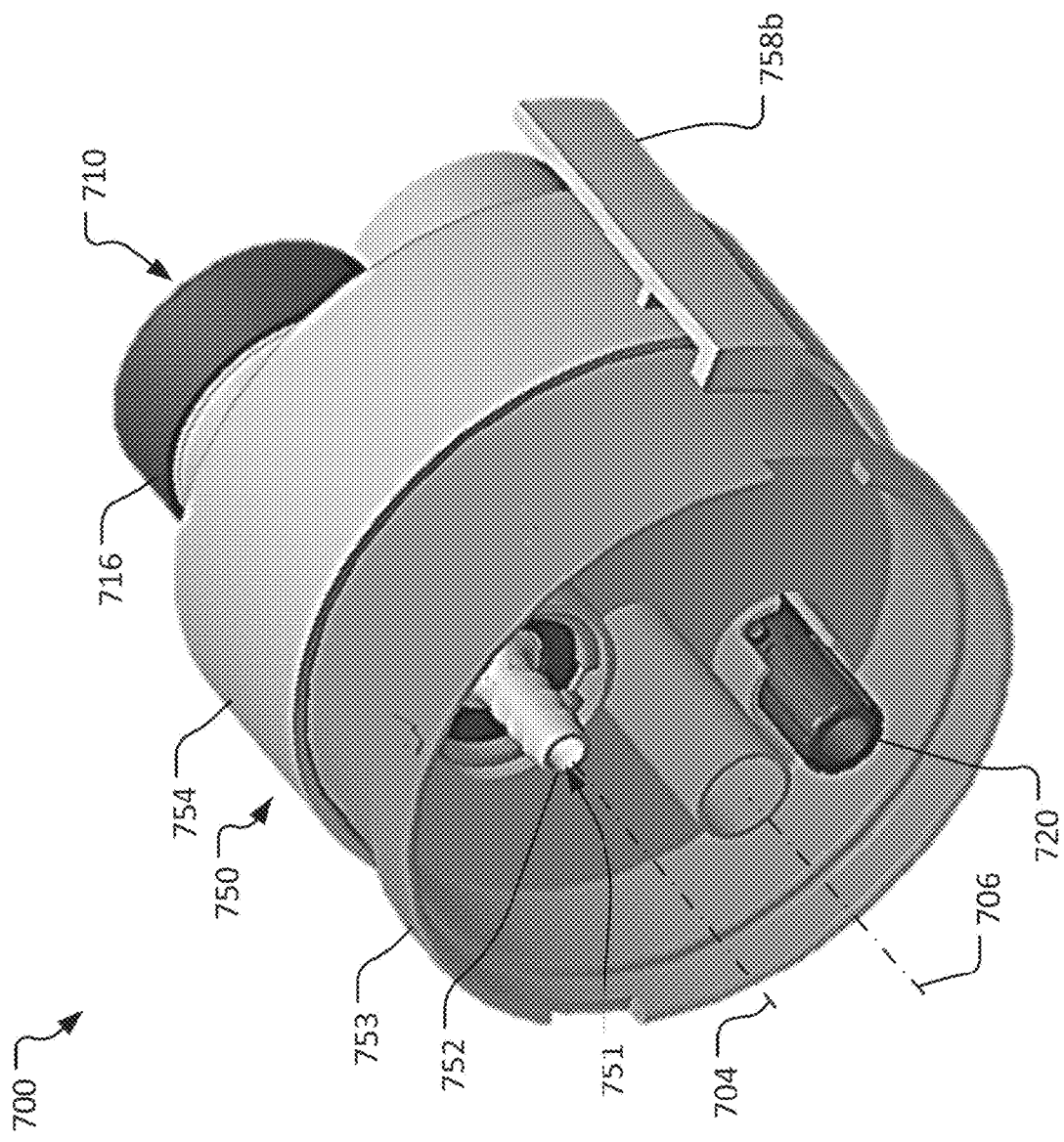
FIG. 38 is a perspective view of the repeatable sterile fluid coupling system of FIG. 33 in a fourth configuration.
Figure 39:
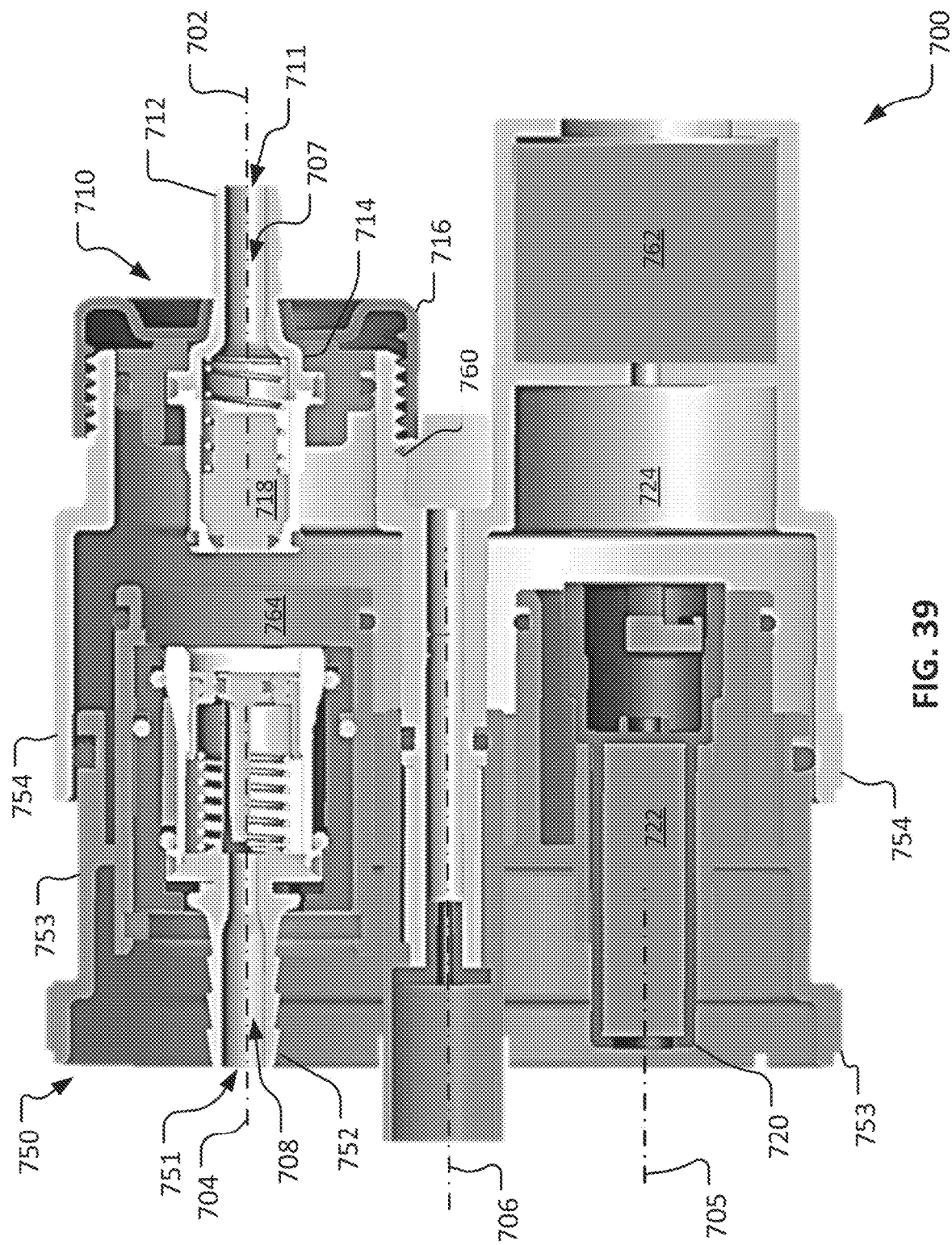
FIG. 39 is a longitudinal cross-sectional side view of the repeatable sterile fluid coupling system of FIG. 33 in the fourth configuration.

Referring to FIGS. 38 and 39, the next step in the process of connecting the first coupling portion 710 with the second coupling portion 750 so as to establish a sterile fluid pathway between end ports 711 and 751 is for the user to rotate the inner housing portion 753 in relation to the outer housing portion 754 about the central axis 706. In the depicted embodiment, the user rotates the inner housing portion 753 in relation to the outer housing portion 754 by about 180°. In some embodiments, the fluid coupling system 700 may be configured such that other amounts of rotation between the housing portions 753 and 754 (e.g., about 90°, about 120°, about 150°, and the like) are used in preparation for establishing a sterile fluid pathway between end ports 711 and 751. In some embodiments, built in structural travel-stop features serve to limit the relative rotational movements of the inner housing portion 753 in relation to the outer housing portion 754. In the depicted embodiment, after the rotation of the inner housing portion 753 in relation to the outer housing portion 754, the latches 758a and 758b become longitudinally realigned with mating members (e.g., notches, and the like) of the inner housing portion 753 in preparation for re-latching the inner housing portion 753 in relation to the outer housing portion 754.

Completion of the rotation of the inner housing portion 753 in relation to the outer housing portion 754 causes the longitudinal axis 702 to become coincident with the longitudinal axis 704. In other words, the rotation results in the valve members 718 and 757 becoming positioned and oriented in longitudinal alignment with each other. The sterile regions 724 and 764 are now in fluid communication with each other.

Figure 40:
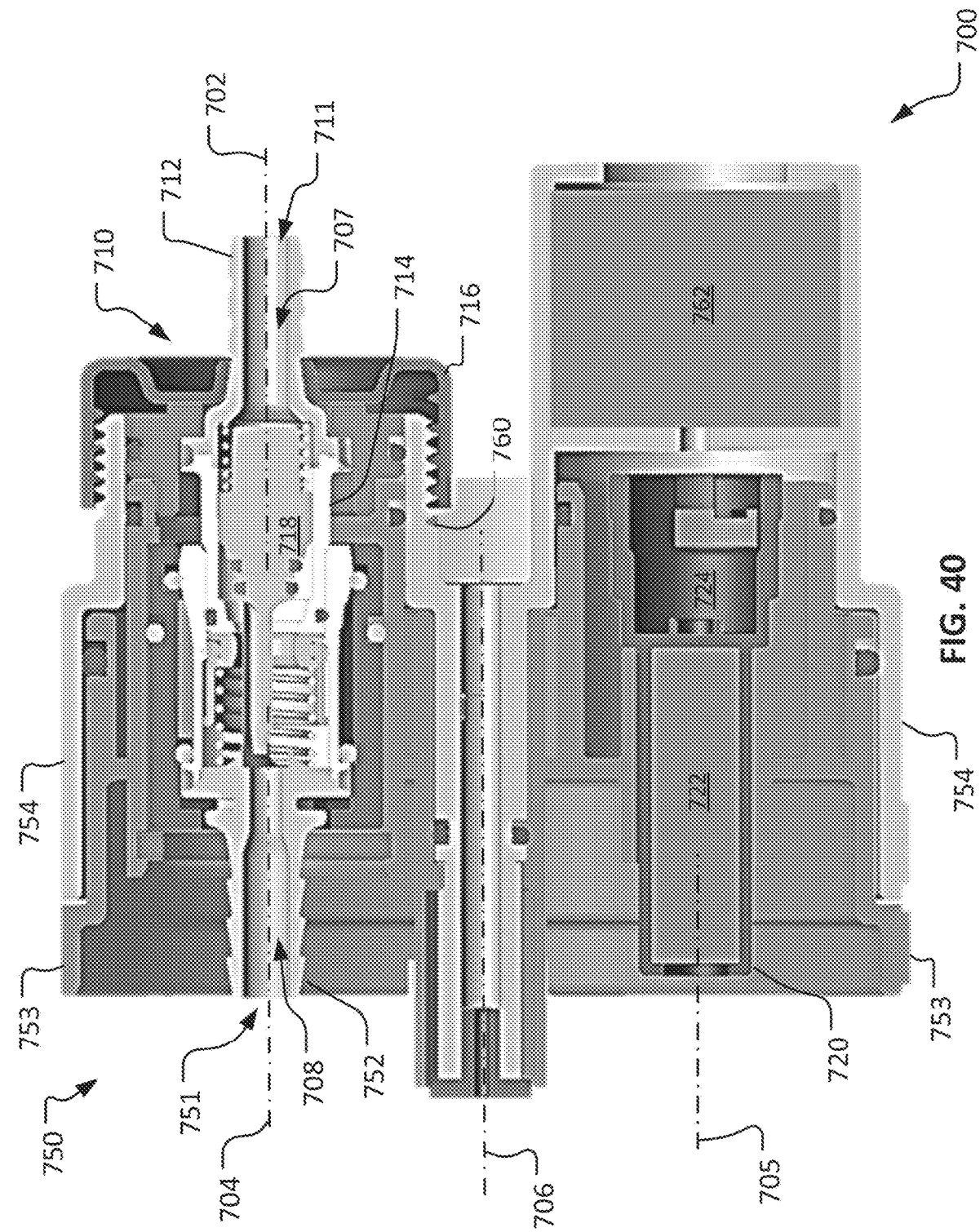
FIG. 40 is a longitudinal cross-sectional side view of the repeatable sterile fluid coupling system of FIG. 33 in a fifth configuration.
Figure 41:
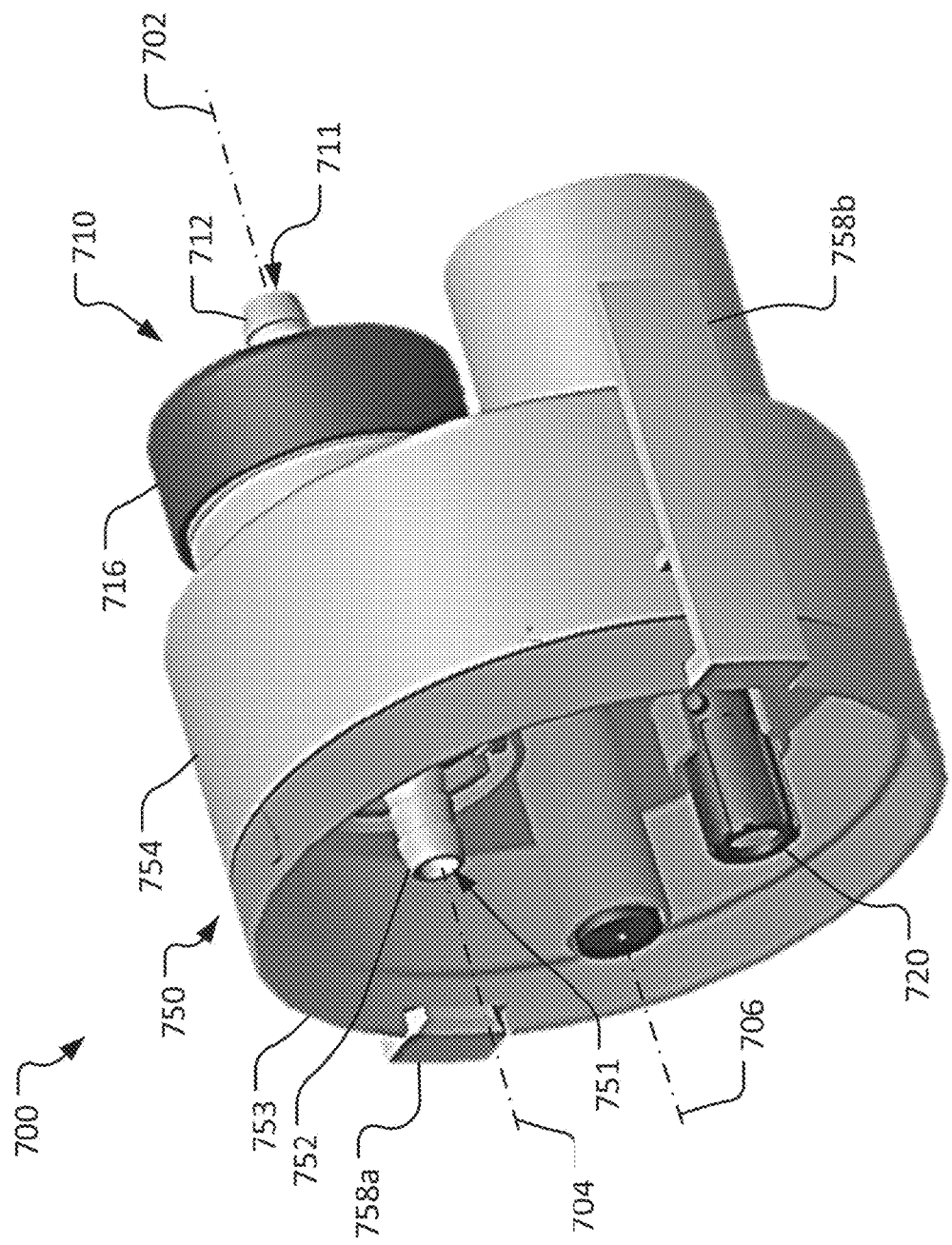
FIG. 41 is a perspective view of the repeatable sterile fluid coupling system of FIG. 33 in the fifth configuration.

Referring to FIGS. 40 and 41, the next step in the process of connecting the first coupling portion 710 with the second coupling portion 750 so as to establish a sterile fluid pathway between end ports 711 and 751 is for the user to longitudinally compress the inner housing portion 753 in relation to the outer housing portion 754.

As the fluid coupling system 700 is longitudinally compressed by the user, the spring members of the valve members 718 and 757 will become compressed and provide resistance to the compression. The inner housing portion 753 and the outer housing portion 754 can be configured to allow the fluid coupling system 700 to be releasably locked while the spring members of the valve members 718 and 757 are compressed. For example, in the depicted embodiment, after compressing the inner housing portion 753 and the outer housing portion 754 toward each other, the latches 758a and 758b can lock the fluid coupling system 700 in the compressed configuration. In result, the user can release the fluid coupling system 700 and the sterile fluid flow pathway will remain open between end ports 711 and 751. In some embodiments, other types of mechanisms can be used to releasably lock the inner housing portion 753 in relation to the outer housing portion 754 such as, but not limited to, a pin/hole, a clip, a bayonet-style connection, a threaded connection, and the like, and combinations thereof.

With the fluid coupling system 700 arranged in the illustrated configuration, fluids can flow through the fluid coupling system 700 between the end ports 711 and 751. The fluid pathway between the end ports 711 and 751 is a sterile fluid pathway.

It should be understood that, to stop fluid flow between the end ports 711 and 751, the user can simply unlatch the latches 758a and 758b and elongate the fluid coupling system 700 to attain the configuration of FIGS. 38 and 39 (such that valve members 718 and 757 are no longer engaged with each other). No rotation of inner housing portion 753 relative to the outer housing portion 754 is required in order to interrupt the fluid pathway between the end ports 711 and 751 (unless the user wants to fully uncouple the first coupling portion 710 from the second coupling portion 750). Thereafter, the fluid pathway between the end ports 711 and 751 can be reestablished by compressing the inner housing portion 753 and the outer housing portion 754 toward each other. Again, the latches 758a and 758b can lock the fluid coupling system 700 in the compressed configuration.

If desired, the fluid coupling system 700 can be fully uncoupled by following the reverse of the process described above for coupling the fluid coupling system 700. As the fluid coupling system 700 is uncoupled (such that the first coupling portion 710 is separated from the second coupling portion 750), the sterility/isolation of the first sterile region 724 and the second sterile region 764 is maintained. For example, as part of the process for separating the first coupling portion 710 from the second coupling portion 750, the cap 720 is reinstalled on the first coupling portion 710, and the coupling portions 710 and 750 are configured as shown in FIG. 33 once again. Thereafter, if desired, the fluid coupling system 700 can be recoupled by following the process described above for coupling the fluid coupling system 700. Once again, a sterile fluid pathway between the end ports 711 and 751 will be established. One of skill in the art will recognize that the repeatable, aseptic fluid coupling system 700 can be connected, disconnected, reconnected, and so on, for multiple cycles. In each case, while the first coupling portion 710 is connected to the second coupling portion 750, and the fluid coupling system 700 is configured as shown in FIGS. 40-41, a sterile/isolated fluid pathway between the end ports 711 and 751 exists.

Figure 42:
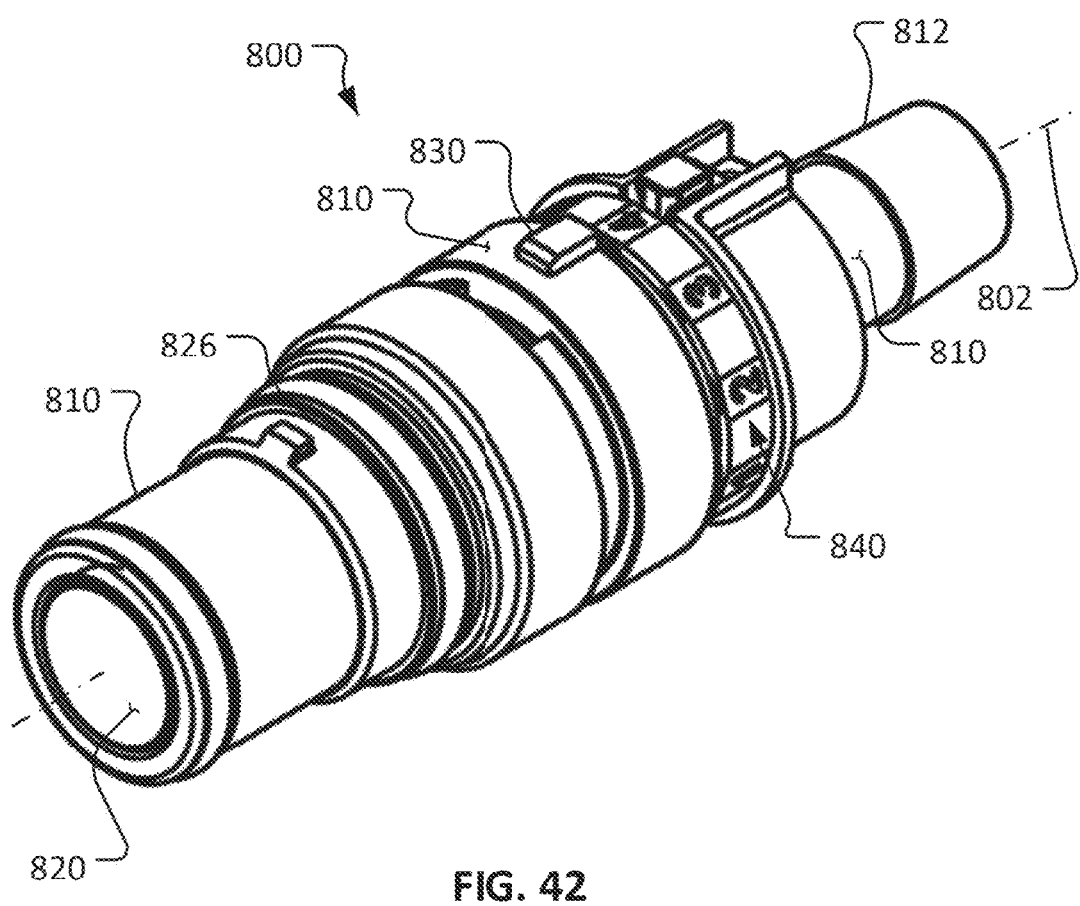
FIG. 42 is a perspective view of another fluid coupling device, in accordance with some embodiments provided herein.
Figure 43:
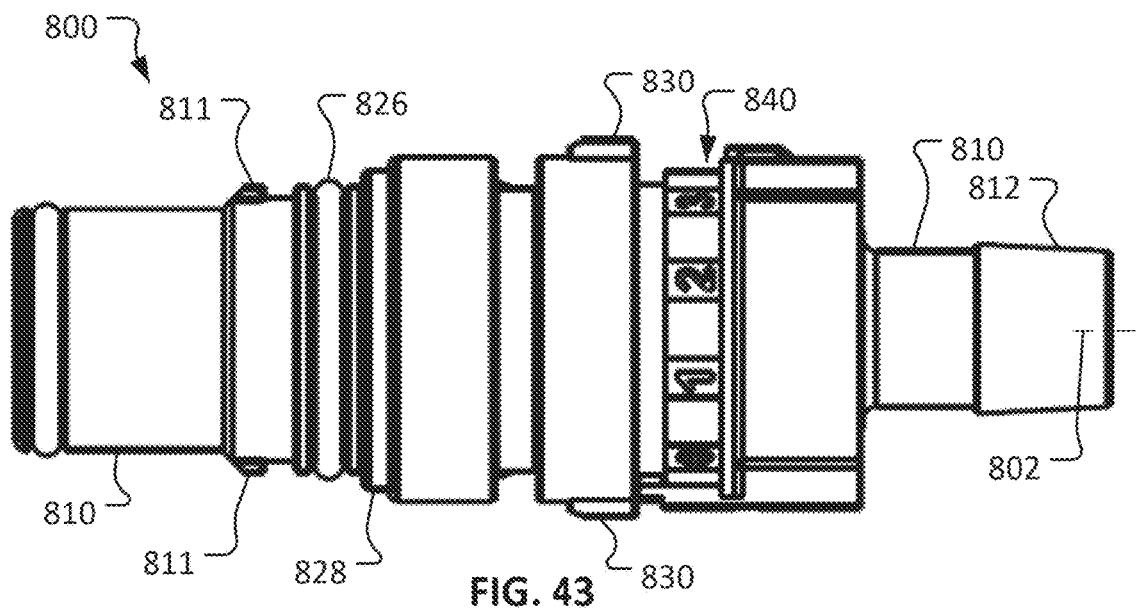
FIG. 43 is a longitudinal side view of the fluid coupling device of FIG. 42.
Figure 44:
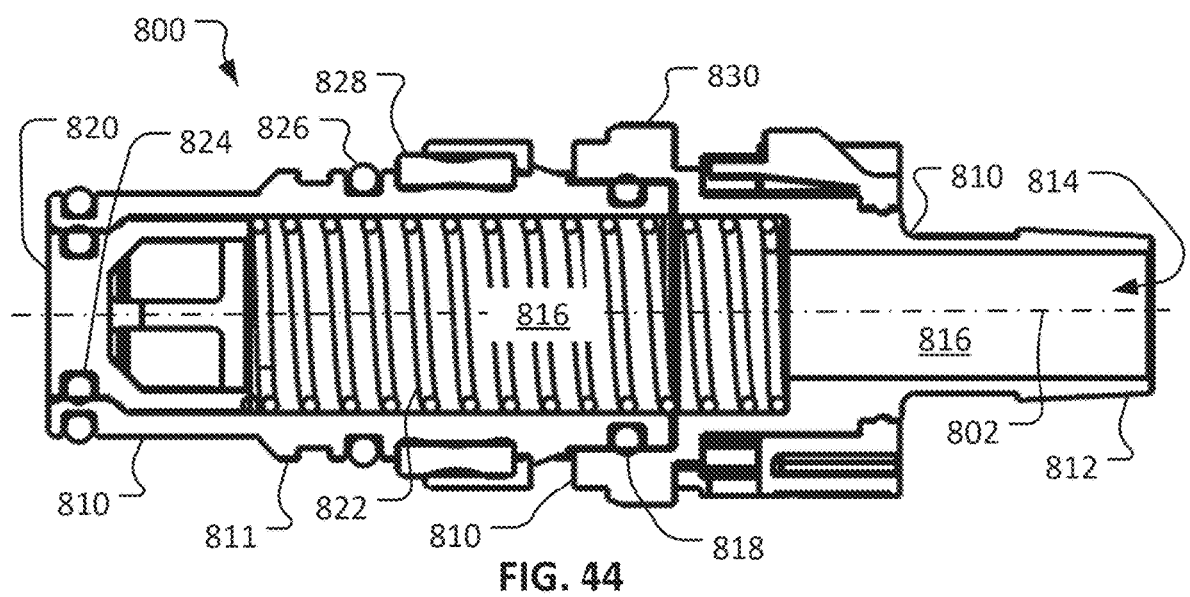
FIG. 44 is a longitudinal cross-section view of the fluid coupling device of FIG. 42.

Referring to FIGS. 42-44, some embodiments of a reusable aseptic fluid coupling system include a fluid coupling device 800 (which is also referred to herein as an insert 800). As described further below, the insert 800 may be releasably coupleable with a cap that protects the sterility/isolation of the fluid flow path within the insert 800 prior to mating the insert 800 with another fluid coupling.

In the depicted embodiment, the insert 800 includes a valve body 810, a valve member 820, and a connection structure 830. The valve member 820 is movably coupled in relation to the valve body 810. The connection structure 830 is coupled to the valve body 810.

In the depicted embodiment, the valve body 810 includes an end portion 812 that defines an end port 814. The end portion 812 may be configured for connecting the insert 800 to another element of a fluid system, such as a tube, container, valve, fitting, and other types of fluid system components. Accordingly, end portion 812 may include various configurations such as, but not limited to, a barbed fitting (as shown), a luer fitting, a compression fitting, a threaded fitting (internal or external), a sanitary fitting, a pigtail, a T-fitting, a Y-fitting, a bag fitment, and any other suitable type of configuration such that the insert 800 is suitable for connection to a fluid system as desired. In some embodiments, the insert 800 may be supplied with a removable cap (not shown), or another type of component, that is releasably coupled with the end portion 812, and that covers end port 814.

The valve body 810 defines a fluid pathway 816 that terminates at the end port 814. In the depicted embodiment, the patency of the fluid pathway 816 is determined by the position of the valve member 820 in relation to the valve body 810. That is, the valve member 820 can move in relation to the valve body 810 to open the fluid pathway 816 through the insert 800, or to close the fluid pathway 816 through the insert 800. In the illustrated, non-limiting configuration, the valve member 820 can translate along a longitudinal axis 802 defined by the valve body 810. In some embodiments, the longitudinal axis 802 is coaxial with the fluid pathway 816, but such an arrangement is not required in all embodiments.

In the illustrated arrangement, the valve member 820 is positioned in a closed position in which the valve member 820 provides a fluidic-sealed occlusion of the fluid pathway 816. A spring member 822 is included, in the depicted embodiment, to bias the valve member 820 to the closed position. A peripheral elastomeric seal 824 (e.g., an o-ring or one or more annular seals with other cross-sectional shapes such as, but not limited to, D-shaped, polygonal, ovular, U-shaped, W-shaped, a four-lobed seal, and the like) is included such that the fluid pathway 816 is sealed closed while the valve member 820 is in the closed position.

As described further below, in some embodiments the valve member 820 can be engaged by another valve member to force the valve member 820 to move in relation to the valve body 810 (e.g., toward the end portion 814), and to thereby open the fluid pathway 816 through the insert 800.

In the depicted embodiment, the valve member 820 is a poppet valve. In some embodiments, other types of valve members 820 are alternatively or additionally used in the valve body 810. For example, in some embodiments the valve member 820 is a type of valve such as, but not limited to, a butterfly valve, a ball valve, a duckbill valve, a diaphragm valve, a needle valve, a pinch valve, a plug valve, and the like.

As with the fluid coupling device 100 described above, the materials from which one or more of the components of the insert 800 are made of include thermoplastics and/or metals (see example materials described above in reference to the fluid coupling device 100). In some embodiments, the insert 800 is metallic-free. That is, in some embodiments no metallic materials are included in the insert 800. For example, in some embodiments no metallic springs are included in the insert 800. Alternatively, in some embodiments the spring member 822 is a metallic spring (e.g., spring steel, stainless steel, and the like). In some embodiments, the seals (e.g., seal 824 et al.) are made of materials such as, but not limited to, silicone, fluoroelastomers (FKM), ethylene propylene diene monomer (EPDM), and the like.

As described further below, in some embodiments portions of the insert 800 are sterile, while other portions of the insert 800 are non-sterile. For example, in some embodiments at least valve member 820 and fluid pathway 816 are sterile, whereas at least some other portions of the insert 800 (e.g., connection structure 830) are non-sterile. Moreover, a cap component (as described immediately below) can be coupled with the insert 800 and can serve to maintain the sterility of portions of the insert 800 such as, but not limited to, the face of the valve member 820.

Figure 45:
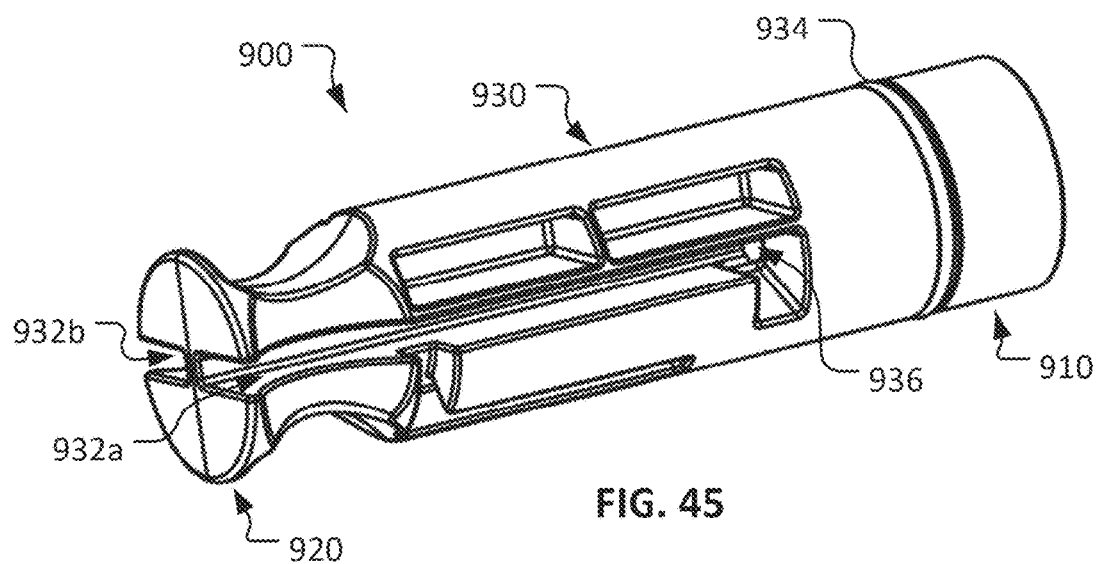
FIG. 45 is a perspective view of a cap that mates with the fluid coupling device of FIG. 42, in accordance with some embodiments provided herein.
Figure 46:
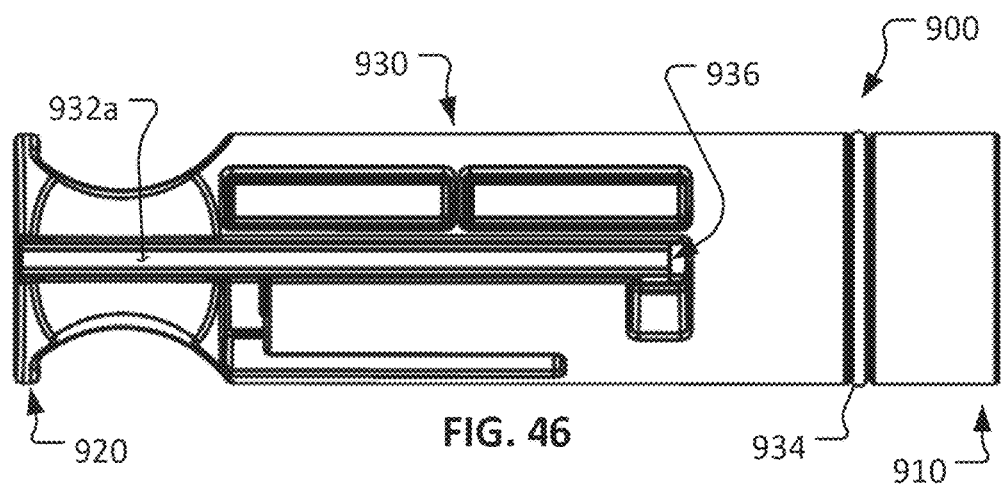
FIG. 46 is a longitudinal side view of the cap of FIG. 45.
Figure 47:
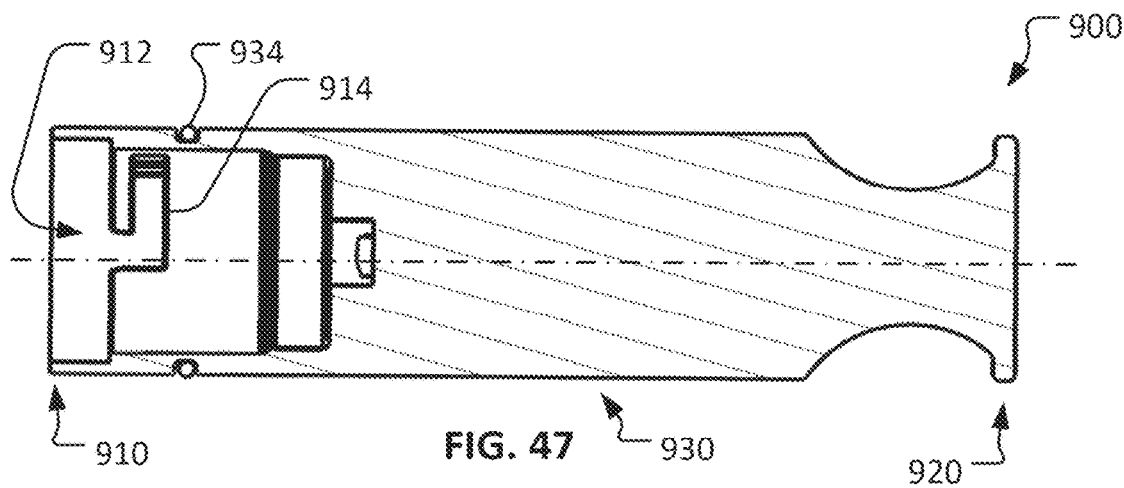
FIG. 47 is a longitudinal cross-sectional view of the cap of FIG. 45.
Figure 48:
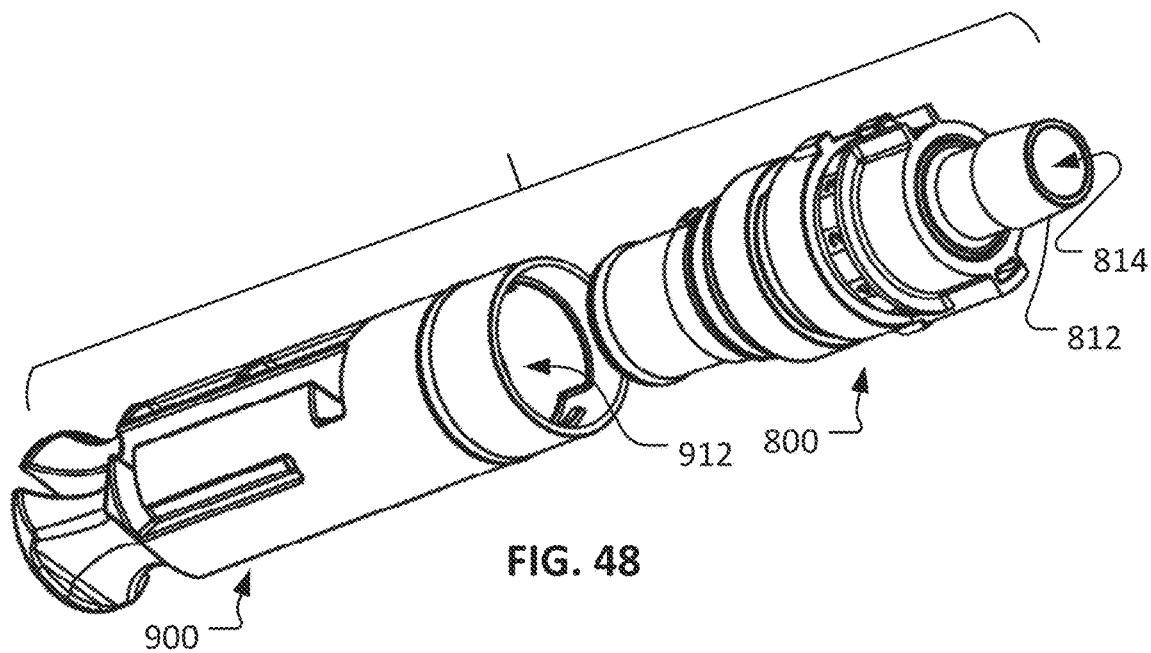
FIG. 48 is an exploded perspective view of the fluid coupling device of FIG. 42 and the cap of FIG. 45.
Figure 49:
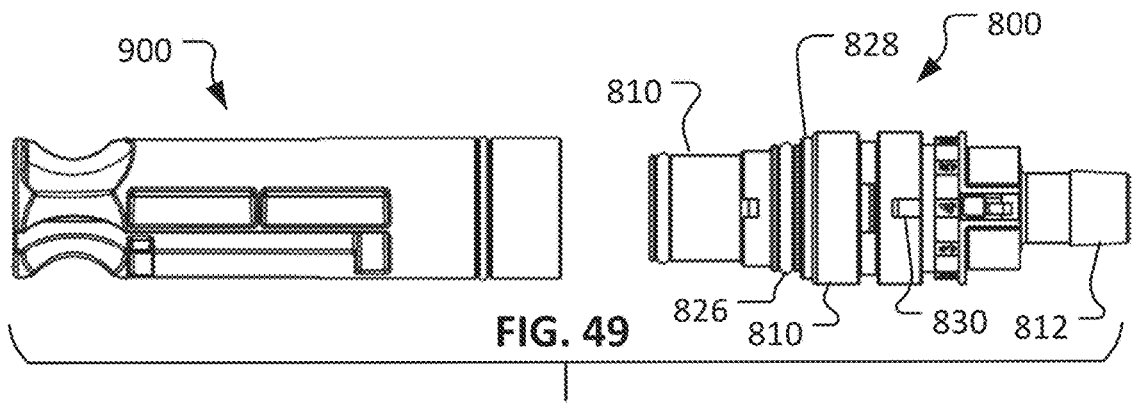
FIG. 49 is an exploded longitudinal side view of the fluid coupling device of FIG. 42 and the cap of FIG. 45.
Figure 50:
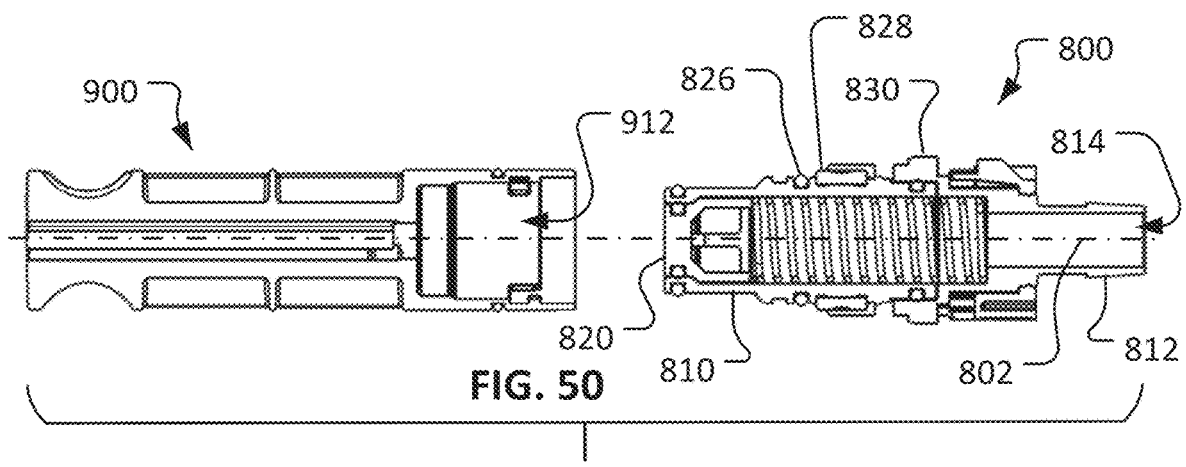
FIG. 50 is an exploded longitudinal cross-sectional view of the fluid coupling device of FIG. 42 and the cap of FIG. 45.
Figure 51:
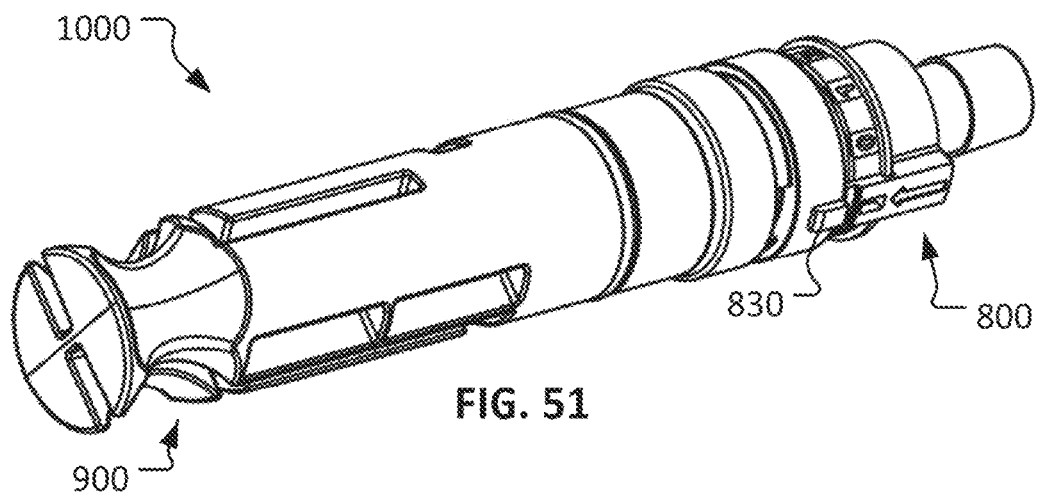
FIG. 51 is a perspective view of the fluid coupling device of FIG. 42 coupled with the cap of FIG. 45 to form a first fluid coupling portion of a repeatable sterile fluid coupling system in accordance with some embodiments.
Figure 52:
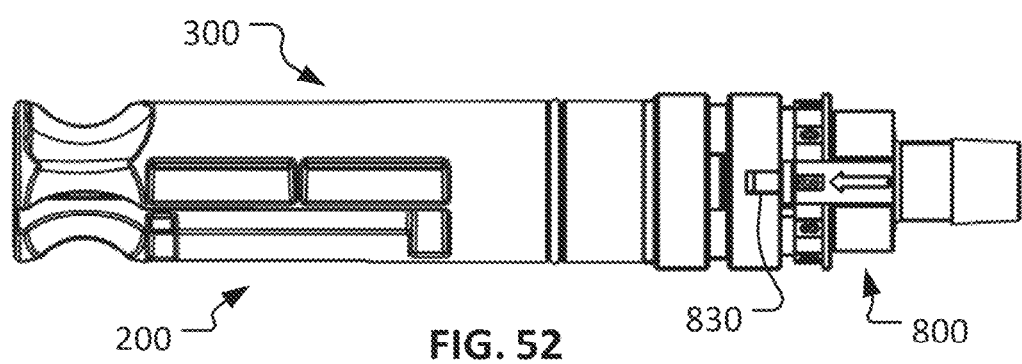
FIG. 52 is a longitudinal side view of the fluid coupling portion of FIG. 51.
Figure 53:
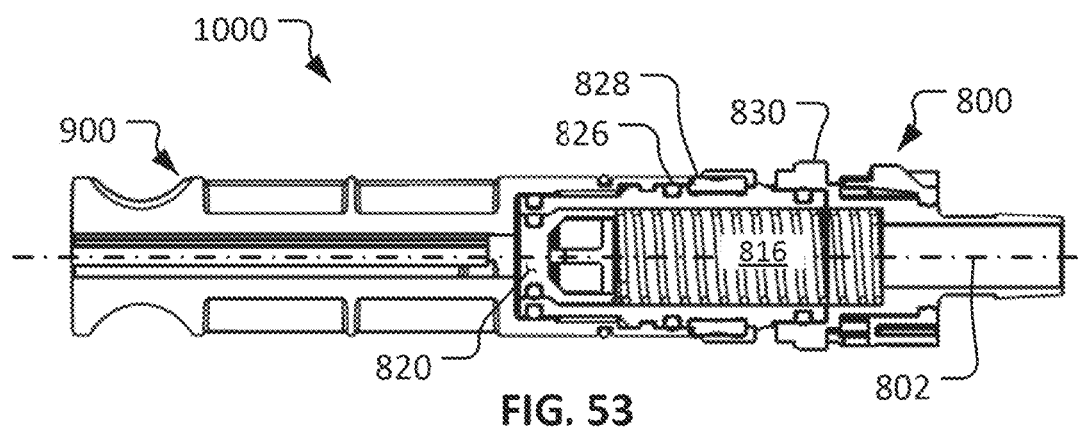
FIG. 53 is a longitudinal cross-sectional side view of the fluid coupling portion of FIG. 51.

Referring also to FIGS. 45-47, a cap 900 can be configured to releasably couple with the insert 800. The cap 900 includes a first end 910, a second end 920, and a cap body 930 therebetween. In the depicted embodiment, an optional vent 936 is included.

The first end 910 can be configured to releasably couple (e.g., mate or engage) with the insert 800. For example, in the depicted embodiment the first end 910 includes a bore 912 that is configured to receive a portion of the valve body 810, and to releasably couple with the valve body 810. In the depicted embodiment, the first end 910 and the valve body 810 are configured for interconnection using a bayonet-style coupling arrangement. The bayonet-style coupling arrangement includes one or more radial projections 811 on the valve body 810 that are releasably engageable with one or more complementary slots 914 defined in the bore 912 of the cap 900. The one or more complementary slots 914 defined in the bore 912 are L-shaped so that the process of engaging the one or more radial projections 811 within the slots includes a relative longitudinal movement followed by a relative rotational movement (i.e., a push-together motion and a turn-to-latch motion). The rotational movement is typically about a ¼ turn or less, but may be more than a ¼ turn in some embodiments. The bayonet-style coupling arrangement can include a detention aspect that provides a positive lock between the insert 800 and the cap 900 when fully mated together. Additionally, in some embodiments the insert 800 and the cap 900 are designed to provide audible and/or tactile feedback to the user to confirm that the insert 800 and the cap 900 are fully mated together. In some embodiments, other types of interconnections can be used such as, but not limited to, threaded connections, detent pin connections, latches, hinges, and the like, and combinations thereof.

In the depicted embodiment, the second end 920 is configured for convenient manual manipulation. That is, in the depicted embodiment the second end 920 includes surface contours that facilitate manual gripping and manipulations such as turning, pulling, pushing, and the like. In some embodiments, other types of features may be additionally or alternatively included to facilitate convenient manual gripping and manipulations of cap 900. Such features may include, but are not limited to, knurling, stippling, other types of texturing, flexible elastomeric inserts, and the like, and combinations thereof.

In some embodiments, such as the depicted embodiment, the cap 900 includes features that configure the cap 900 to restrictively mate with another coupling portion in one or more desired relative orientations (as described further below). For example, in the depicted embodiment the cap 900 includes slots 932a and 932b. The slots 932a and 932b are configured to receive one or more projections of the other coupling portion, and to thereby restrict the relative movements between the cap 900 and the other coupling portion to only particular relative movements as desired (e.g., like a key and keyway arrangement). In some embodiments, other features can be included on the cap 900 to achieve the purpose of restrictively mating with another coupling portion in one or more desired relative orientations. For example, in some embodiments features such as, but not limited to, gear teeth, splines, threads, compression fits, and the like, and combinations thereof can be included as part of the cap 900.

In the depicted embodiment, the cap 900 also includes the seal member 934. The seal member 934 surrounds the outer periphery of the cap body 930, and projects at least slightly proud therefrom. As described further below, the seal member 934 is configured to seal with a portion of another coupling portion, and to maintain the sterility of sterile portions of insert 800 and/or the isolation of portions of the insert 800 as desired.

The cap 900 can also include the optional vent 936 in some embodiments. The vent 936 provides an air-transmissible pathway between the bore 912 and the regions exterior of the cap 900. In some embodiments, a filter media or porous element is included within the vent 936. Such a filter or porous element can serve to inhibit transmission of particles and/or microorganisms, while still allowing transmission of air therethrough. In some embodiments, the filter media or porous element of the vent 936 allows the transmission of materials that are smaller than about 0.2 µm in size, while inhibiting the transmission of materials that are larger. In some embodiments, the filter media or porous element of the vent 936 inhibits the transmission of materials that are larger than about 0.1 µm, or about 0.3 µm, or about 0.4 µm, or about 0.5 µm, or larger than 0.5 µm, while allowing the transmission of materials that are smaller.

The cap 900 can be constructed of any of the materials described above in reference to the insert 800.

Referring to FIGS. 48-53, the insert 800 and the cap 900 are configured to releasably couple with each other to become an assembled first coupling portion 1000. In the coupled configuration of the first coupling portion 1000, at least the portion of the valve body 810 that houses the valve member 820 is received in the bore 912 of the cap 900.

In some implementations, the assembled coupling portion 1000 (and the other coupling portions described herein) is sterilized prior to use (e.g., using any suitable sterilization method such as gamma sterilization, ethylene oxide sterilization, e-beam sterilization, Noxilizer™ sterilization, Revox® sterilization, or using an autoclave, and the like). In some cases during the sterilization, a cap (not shown) may be included on the end portion 812 to seal the end port 814 (and, hence, the fluid pathway 816). In some cases the assembled coupling portion 1000 may be coupled with tubing and/or other components prior to sterilization, and the assembly is sterilized in the coupled configuration. After sterilization, the cap 900 maintains the sterility of the portions of the insert 800 that are within the bore 912, and of the fluid pathway 816. The sterility is maintained, while the cap 900 is coupled with the insert 800, at least in part because of a seal 826 and/or an optional seal 828 located between the cap 900 and the valve body 810. Hence, even while the sterilized coupling portion 1000 is exposed to a non-sterile environment, the cap 900 can serve to maintain the sterility of the portions of the insert 800 that will contact a fluid being transmitted through the insert 800 (in the manner described further below).

In the depicted embodiment, the coupling mechanism between the cap 900 and the insert 800 is a bayonet-style connection. In some embodiments, other types of coupling mechanisms are used such as, but not limited to, threaded connections, press-fit connections, latch connections, cam-lock connections, over-center connections, and the like, and combinations thereof.

Figure 54:
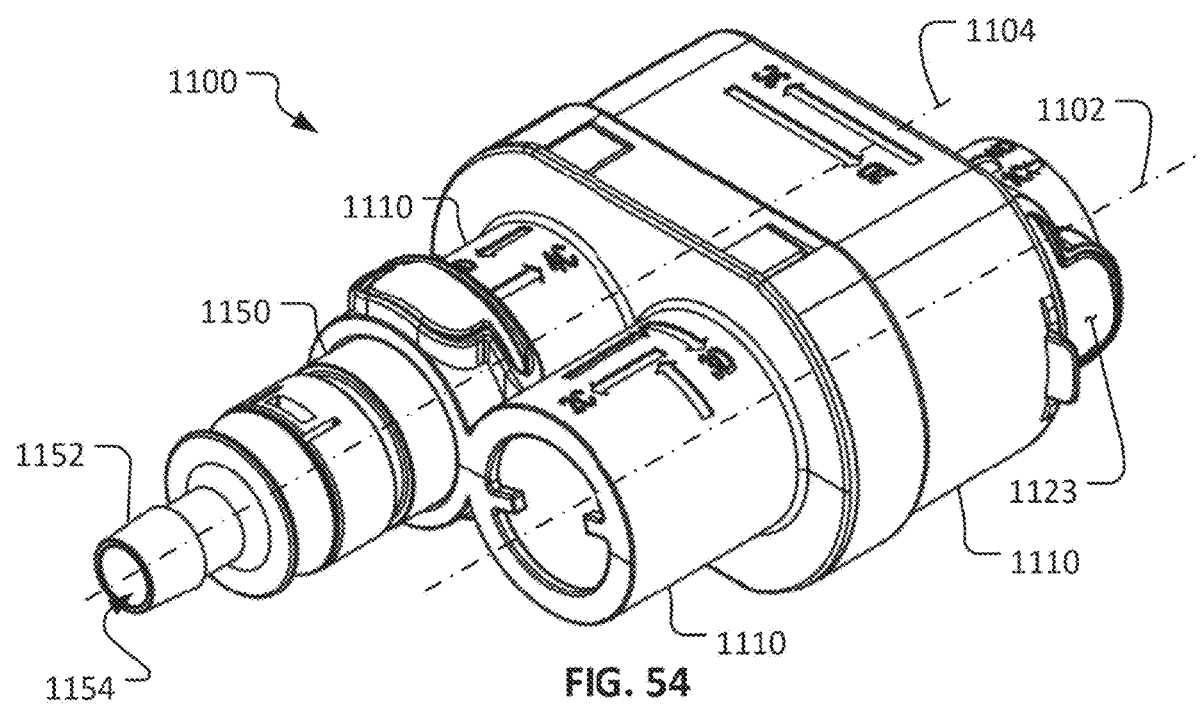
FIG. 54 is a perspective view of a second fluid coupling portion of a repeatable sterile fluid coupling, in accordance with some embodiments.
Figure 55:
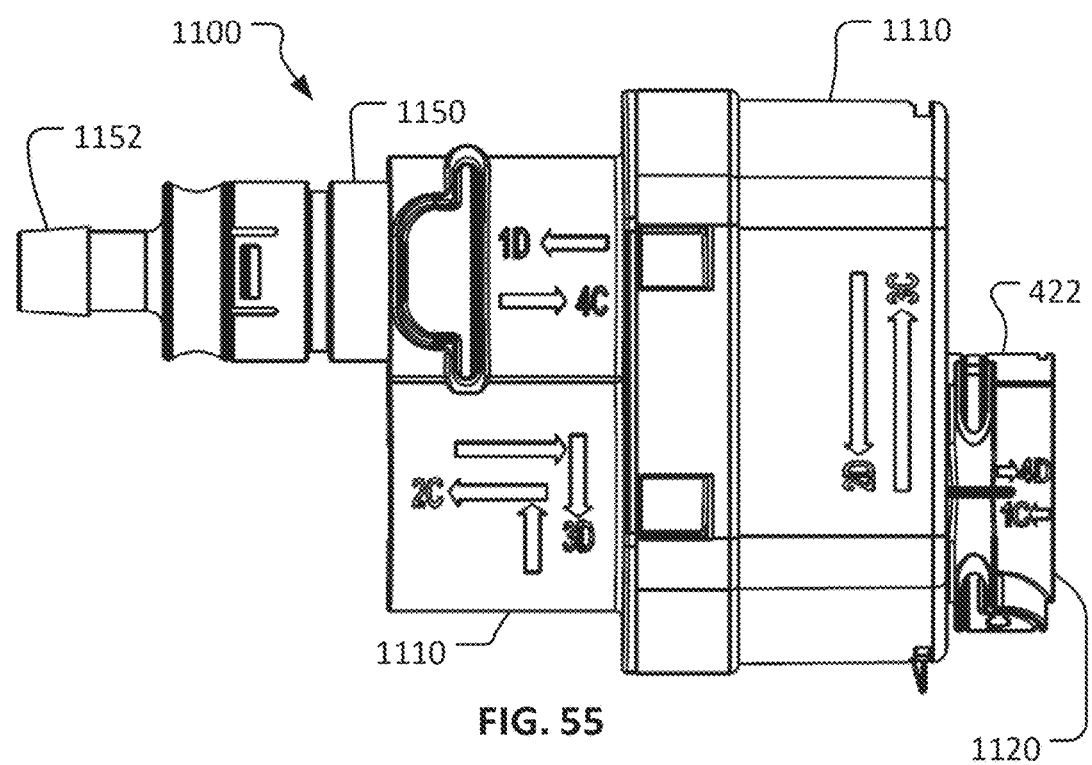
FIG. 55 is a longitudinal side view of the fluid coupling portion of FIG. 54.
Figure 56:
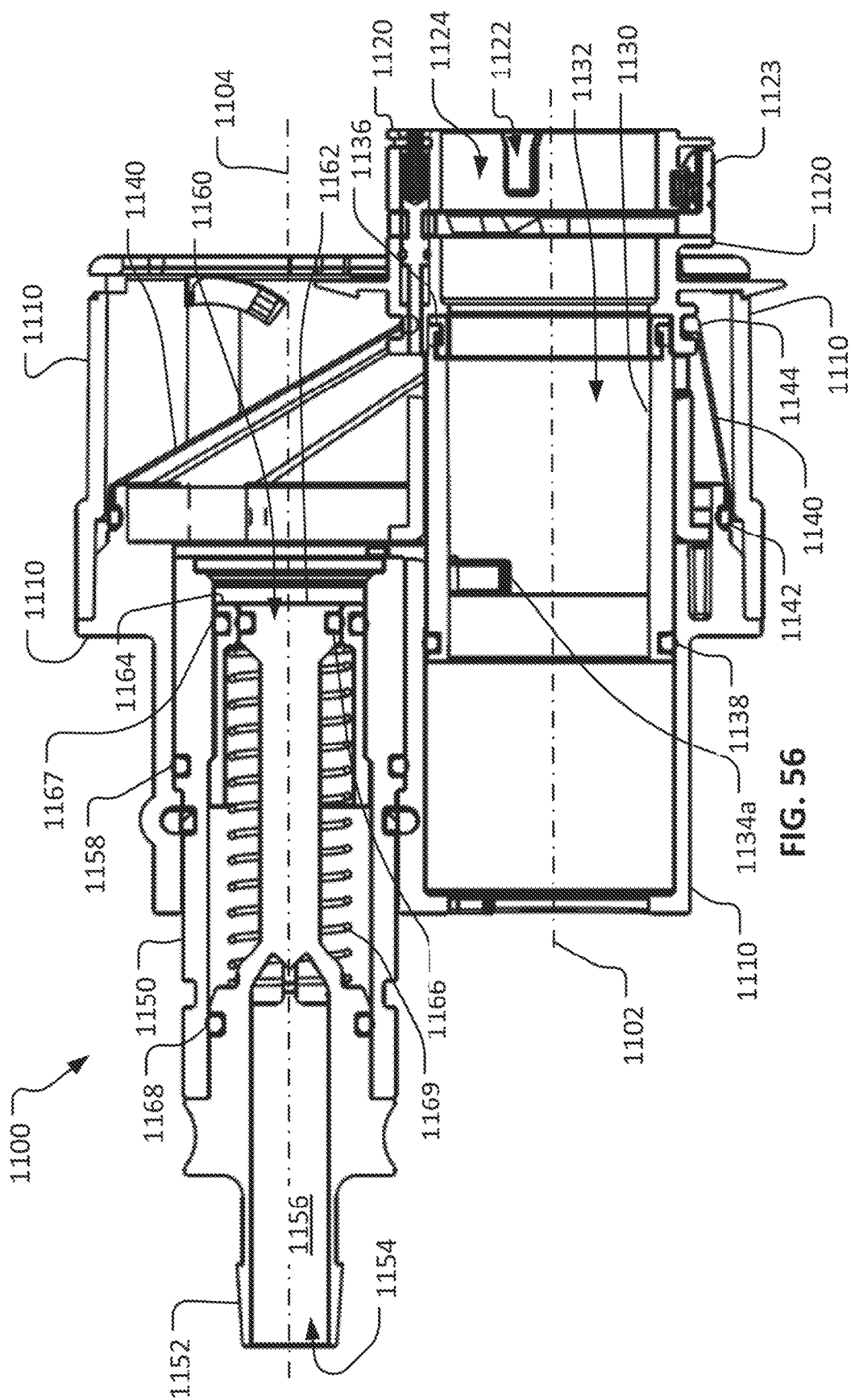
FIG. 56 is a longitudinal cross-sectional side view of the fluid coupling portion of FIG. 54.

Referring to FIGS. 54-56, a second coupling portion 1100 (which is also referred to herein as a main body assembly 1100) can be configured to releasably mate with the first coupling portion 1000 described above. As described further below, the coupling portions 1000 and 1100 provide a repeatably connectable aseptic fluid coupling system. In other words, the coupling portions 1000 and 1100 (when previously sterilized) can be connected to establish a sterile fluid flow path therethrough, and coupling portions 1000 and 1100 can thereafter be disconnected and reconnected multiple times such that the sterile fluid flow path is repeatably established. That sterile fluid flow path can be repeatably established through the coupling portions 1000 and 1100 even though the coupling portions 1000 and 1100 are disconnected and reconnected multiple times in a non-sterile environment.

In the depicted embodiment, the main body assembly 1100 includes a housing 1110, a connection member 1120 (also referred to herein as a shuttle 1120), a sleeve 1130 (also referred to herein as a slider 1130), a flexible member 1140, a body valve 1150, and a valve member 1160. The housing 1110 defines a first longitudinal axis 1102 and a second longitudinal axis 1104. In the depicted embodiment, the first longitudinal axis 1102 is parallel with the second longitudinal axis 1104. The parallelism between the axes 1102 and 1104 is not required in all embodiments.

The shuttle 1120 can be movably coupled with the housing 1110. In the depicted embodiment, the shuttle 1120 is slidably coupled with the housing 1110. In particular (as described further below), the shuttle 1120 can translate laterally between a first position (as shown) that is coaxial with the first longitudinal axis 1102 and a second position (e.g., FIGS. 66-71) that is coaxial with the second longitudinal axis 1104. The shuttle 1120 can translate along a path that is transverse to one or both of the axes 1102 and 1104. In the depicted embodiment, the shuttle 1120 can translate along a path that is orthogonal to the axes 1102 and 1104.

The shuttle 1120 includes a connection structure 1122 that is configured to releasably mate with the connection structure 830 of the insert 800 (e.g., FIGS. 42-44). In the depicted embodiment, connection structures 830 and 1122 are projections and slots, respectively, that releasably mate with each other. When the connection structures 830 and 1122 are fully coupled with each other, the coupling portions 1000 and 1100 releasably latch together. Thereafter, to separate the coupling portions 1000 and 1100, the user must depress a release button 1123. The release button 1123 will only be actuatable if the cap 900 is properly coupled with the insert 800. In some embodiments, the connection structures 830 and 1122 include other types of connection mechanisms such as, but not limited to, a snap connection, a thumb latch connection, a bayonet-style connection, a luer connection, a threaded connection, a luer-lock connection, and the like, and combinations thereof.

The shuttle 1120 defines a connection member bore 1124. In the depicted embodiment, the slider 1130 is located within the connection member bore 1124. The slider 1130 is slidably engageable within the shuttle 1120. While the slider 1130 is engaged with the shuttle 1120 (as shown), the slider 1130 mechanically interferes with the shuttle 1120 such that the shuttle 1120 cannot move from the first position (as shown) that is coaxial with the first longitudinal axis 1102.

As described further below, the slider 1130 can be moved away from the shuttle 1120 such that the slider 1130 becomes disengaged from the shuttle 1120. For example, in the depicted embodiment the slider 1130 can be slidably translated (to the left in FIG. 56) along the first longitudinal axis 1102 away from the shuttle 1120. When the slider 1130 has been disengaged from the shuttle 1120, in some embodiments the shuttle 1120 is free to be moved from the first position that is coaxial with the first longitudinal axis 1102 toward the second position that is coaxial with the second longitudinal axis 1104.

The slider 1130 defines a sleeve bore 1132. The sleeve bore 1132 can be configured to receive the cap 900 (FIGS. 45-53). The slider 1130 can include features to releasably mate with the cap 900. For example, in the depicted embodiment the slider 1130 includes a first projection 1134a and a second projection 1134b (not visible) that extend within the sleeve bore 1132. The first projection 1134a and the second projection 1134b can releasably mate with the slots 932a and 932b of the cap 900. While in the depicted embodiment projections and slots are used as the features whereby the slider 1130 and the cap 900 can releasably mate with each other, in some embodiments other types of features can be included. Such features can include, but are not limited to, threads, snap-together connections, bayonet-style connections, compression connections, and the like, and combinations thereof.

The slider 1130 may include one or more seals. For example, in the depicted embodiment the slider 1130 includes a first seal 1136 that can slidably engage with the bore 1124 of the shuttle 1120 and/or the housing 1110, and a second seal 1138 that slidably engages with the housing 1110. The seals 1136 and 1138 can extend around the entire periphery of the slider 1130. As described further below, the seals 1136 and 1138 can provide sterility barriers and/or isolation barriers between sterile areas/surfaces and non-sterile areas/surfaces.

The main body assembly 1100 can also include the flexible member 1140. The flexible member 1140 acts as a seal that provides a sterility/isolation barrier between particular regions interior to the coupling portion 1100, and regions external to the coupling portion 1100. Moreover, the flexible member 1140 provides the seal while accommodating the aforementioned movement of the shuttle 1120 in relation to the housing 1110. Accordingly, at least some portions of the flexible member 1140 are extendable and contractible to accommodate the movement of the shuttle 1120. In some embodiments, the flexible member 1140 is elastic or otherwise reconfigurable such that the flexible member 1140 stretches to accommodate the movement of the shuttle 1120. In some embodiments, the flexible member 1140 may include folds, pleats, bellows, spring members, and the like, to help accommodate the movement of the shuttle 1120.

In the depicted embodiment, the flexible member 1140 includes an outer periphery 1142 and an inner periphery 1144. The outer periphery 1142 is affixed to the housing 1110. The inner periphery 1144 is affixed to the shuttle 1120.

The flexible member 1140 can be made of any suitable material. For example, the flexible member 1140 can be made of materials such as, but not limited to, silicone, ePTFE, EPDM, urethane, fluorosilicone, neoprene, nitrile, latex, and the like, and combinations thereof.

The main body assembly 1100 can also include the body valve 1150 that houses the valve member 1160. The body valve 1150 includes an end portion 1152 that defines an end port 1154. As with the end portion 812 described above, end portion 1152 can be configured for any suitable type of connection. Accordingly, end portion 1152 may have various configurations such as, but not limited to, a barbed fitting (as shown), a luer fitting, a compression fitting, a threaded fitting (internal or external), a sanitary fitting, a pigtail, a T-fitting, a Y-fitting, a bag fitment, and any other suitable type of configuration such that the coupling portion 1100 is suitable for connection to a fluid system as desired. In some embodiments, the main body assembly 1100 may be supplied with a removable cap (not shown) that is releasably coupled with the end portion 1152, and that covers end port 1154.

The body valve 1150 defines a fluid pathway 1156 that terminates at the end port 1154. In the depicted embodiment, the patency of the fluid pathway 1156 is determined by the positions of the components of the valve member 1160 in relation to the body valve 1150. That is, the components of the valve member 1160 can move in relation to the body valve 1150 to open the fluid pathway 1156 through the main body assembly 1100, or to close the fluid pathway 1156 through the main body assembly 1100. In the depicted arrangement of the components of the valve member 1160, the fluid pathway 1156 is occluded by the valve member 1160. As described further below, while the shuttle 1120 is coaxial with the second longitudinal axis 1104, and while the first coupling portion 1000 and the main body assembly 1100 are mated together, the valve member 1160 can engage with the valve member 820 (FIG. 44) to open a fluid pathway between end ports 814 and 1154. In that manner a sterile fluid pathway can be established through both of the first coupling portion 1000 and the main body assembly 1100, while the coupling portions 1000 and 1100 are mated together.

In the depicted embodiment, the valve member 1160 includes a center stem 1162, a spring-loaded movable valve sleeve 1164, and a spring 1169. In the illustrated arrangement, the valve member 1160 is oriented in a closed position in which the valve member 1160 provides a fluidic-sealed occlusion of the fluid pathway 1156. The valve sleeve 1164 can be forced away from the end of the center stem 1162 (i.e., to the left in FIG. 56) to allow fluid flow past the valve member 1160. The spring member 1169 is included, in the depicted embodiment, to bias the movable valve sleeve 1164 to the closed position. Peripheral elastomeric seals 1166, 1167, and 1168 (e.g., o-rings or one or more annular seals with other cross-sectional shapes such as, but not limited to, D-shaped, polygonal, ovular, U-shaped, W-shaped, a four-lobed seal, and the like) are included such that the fluid pathway 1156 is sealed closed while the valve member 1160 is in the closed orientation.

In some embodiments, the valve member 1160 is a poppet valve. In some embodiments, other types of valve members 1160 are alternatively or additionally used in the body valve 1150. For example, in some embodiments the valve member 1160 is a type of valve such as, but not limited to, a butterfly valve, a ball valve, a duckbill valve, a diaphragm valve, a needle valve, a pinch valve, a plug valve, and the like.

In some embodiments, the body valve 1150 is movable in relation to the housing 1110. In the depicted embodiment, the body valve 1150 can be slidably translated along the second longitudinal axis 1104. For example, in the depicted embodiment the body valve 1150 can be slidably translated (to the right in FIG. 56) along the first longitudinal axis 1102 generally toward the shuttle 1120.

In the depicted embodiment, the body valve 1150 is physically prevented (blocked) from being translated longitudinally toward the shuttle 1120 unless the connector member 1120 is coaxial with the body valve 1150. That is, unless the shuttle 1120 is in its second position (coaxial with the second longitudinal axis 1104), the body valve 1150 cannot move from its position as shown in FIG. 56.

The body valve 1150 may include one or more seals. For example, in the depicted embodiment the body valve 1150 includes a seal 1158 that can slidably engage with the housing 1110. The seal 1158 can extend around the entire periphery of the body valve 1150. As described further below, the seal 1158 can provide sterility/isolation barriers between sterile areas/surfaces and non-sterile areas/surfaces.

As with second coupling portion 400 described above in reference to FIGS. 13-15, the materials from which the components of the main body assembly 1100 can be made of include thermoplastics and/or metals (see example materials described above in reference to the fluid coupling device 400). In some embodiments, the main body assembly 1100 is metallic-free. That is, in some embodiments no metallic materials are included in the main body assembly 1100. For example, in some embodiments no metallic springs are included in the main body assembly 1100. Alternatively, in some embodiments the spring member 1169 is a metallic spring (e.g., spring steel, stainless steel, and the like). In some embodiments, the spring member 1169 is made of a polymeric material. In some embodiments, the seals (e.g., seal 1136 et al.) are made of materials such as, but not limited to, silicone, fluoroelastomers (FKM), ethylene propylene diene monomer (EPDM), and the like.

In some implementations, the assembled coupling portion 1100 (and the other coupling portions described herein) is sterilized prior to use (e.g., using any suitable sterilization method such as gamma sterilization, ethylene oxide sterilization, e-beam sterilization, Noxilizer™ sterilization, Revox® sterilization, or using an autoclave, and the like). In some cases during the sterilization, a cap (not shown) may be included on the end portion 1152 to seal the end port 1154. In some cases the assembled coupling portion 1100 may be coupled with tubing and/or other components prior to sterilization, and the assembly is sterilized in the coupled configuration.

As described further below, in some embodiments portions of the main body assembly 1100 are sterile, while other portions of the main body assembly 1100 are non-sterile. For example, in some embodiments at least valve member 1160 and fluid pathway 1156 are sterile, whereas at least some other portions of the main body assembly 1100 (e.g., connection structure 1122) are non-sterile.

FIGS. 57-71 illustrate a sequential process of connecting the first coupling portion 1000 with the main body assembly 1100 so as to establish a sterile/isolated fluid pathway therethrough (between end ports 814 and 1154). Thereafter, to disconnect the first coupling portion 1000 from the main body assembly 1100, the process can be reversed. It should be understood that the steps for the connection and disconnection processes are described primarily in relation to a particular example embodiment (the first coupling portion 1000 with the main body assembly 1100), and that variations of the steps are also envisioned within the scope of this disclosure.

The coupling portions 1000 and 1100 (and the other coupling portions of the other coupling embodiments described herein) are designed to be functionally interchangeable coupling portions. For example, the coupling portion 1000 is designed such that it can be coupled with two or more of the coupling portions 1100 (at individual times), if so desired. That is, the first coupling portion 1000 may be coupled with a particular main body assembly 1100, then uncoupled, and then coupled with a different main body assembly 1100, and so on for still other second coupling portions 1100 as desired. Likewise, the main body assembly 1100 may be coupled with a particular first coupling portion 1000, then uncoupled, and then coupled with a different first coupling portion 1000, and so on for still other first coupling portions 1000 as desired. In each instance of coupling and uncoupling, the isolation from the surrounding environment of the fluids in the various coupling portions 1000 and 1100 can be maintained.

Referring to FIGS. 57-59, the first coupling portion 1000 and the main body assembly 1100 can be selectively mated with each other, and unmated from each other. In the depicted embodiment, the cap 900 of the first coupling portion 1000 can be inserted into the bores 1124 and 1132 of the shuttle 1120 and the slider 1130 respectively (FIG. 56). The projections 1134*a* and 1134*b* can be oriented in alignment with the slots 932*a* and 932*b* (FIG. 45) to facilitate proper, full engagement between the first coupling portion 1000 and the main body assembly 1100. To initiate the process of releasably coupling the first coupling portion 1000 and the main body assembly 1100, the connection structures 830 and 1122 can be mated together. For example, in the depicted embodiment the connection structure 830 is aligned with the connection structure 1122 such that connection structure 830 is slid into engagement with the connection structure 1122. When the first coupling portion 1000 and the main body assembly 1100 are fully engaged with each other, a latching action between the two will result and the first coupling portion 1000 and the main body assembly 1100 will be releasably mated with each other. Tactile and/or audible feedback may be provided when the first coupling portion 1000 and the main body assembly 1100 are properly releasably mated with each other. To decouple the first coupling portion 1000 from the main body assembly 1100, the user will need to depress the release button 1123 and then separate the two. Such decoupling will only be possible while the cap 900 is fully engaged with the insert 800.

In some implementations, the first coupling portion 1000 and the main body assembly 1100 are each sterilized prior to use. That is, at least some interior regions/surfaces of the first coupling portion 1000 and the main body assembly 1100 are sterile prior to mating the first coupling portion 1000 and the main body assembly 1100 together. As described further below, the first coupling portion 1000 and the main body assembly 1100 are configured such that the sterile regions/surfaces remain sterile throughout the processes of connecting and disconnecting the first coupling portion 1000 and the main body assembly 1100.

In some implementations, the repeatable sterile fluid coupling system made up of the first coupling portion 1000 mated with the main body assembly 1100 is configured to, for example, releasably connect a first fluid system equipment or container to a second fluid system equipment or container. In one non-limiting example, the repeatable sterile fluid coupling systems described herein can provide a reusable, aseptic connection and disconnection capability for a fluid path between a bioreactor system (e.g., connected directly to one coupling portion 1000/1100, or connected via a fluid tube) and a fluid container in the form of a media bag (e.g., connected directly to the other coupling portion 1000/1100, or connected via a fluid tube).

Referring to FIGS. 60-62, after completing the interconnection of the first coupling portion 1000 and the main body assembly 1100 as described above, the depicted fluid coupling system 1200 is arranged in the configuration as shown. In this arrangement, the longitudinal axis 802 of the first coupling portion 1000 is coincident with the first longitudinal axis 1102 of the main body assembly 1100. The seal 828 provides an airtight seal between the first coupling portion 1000 and the main body assembly 1100. The slider 1130 is positioned so as to restrict the movement of the shuttle 1120 away from the position shown (e.g., a translational movement of the shuttle 1120 and first fluid coupling portion 1000 toward the second longitudinal axis 1104).

As described above, the first coupling portion 1000 and the main body assembly 1100 can be previously sterilized. Accordingly, the first coupling portion 1000 can have a first sterile region 1001, and the main body assembly 1100 can have a second sterile region 1101. The sterile regions 1001 and 1101 are in addition to the sterile fluid pathways 816 and 1156. The first sterile region 1001 includes the spaces and surfaces between the cap 900 and the insert 800. In some embodiments, the gasket 826 serves to seal the first sterile region 1001 from the other, outer surfaces of the first coupling portion 1000 that may be unsterile. The second sterile region 1101, in general, includes the spaces and surfaces defined between the flexible member 1140, the shuttle 1120, and the housing 1110.

In the configuration as shown, the cap 900 is still engaged with the insert 800. The second end 920 of the cap 900 is projecting out from the housing 1110 of the main body assembly 1100. In this arrangement, the second end 920 is accessible to a user such that the cap 900 can be manipulated.

The next step in the process of coupling the first coupling portion 1000 with the main body assembly 1100 to create a fluid flow pathway therethrough is to remove the cap 900 from the insert 800. In the depicted embodiment, the cap 900 can be removed from the insert 800 by first rotating the cap 900 (e.g., without limitation, about 10° to about 45°, or about 20° to about 40°, or about 25° to about 35°) and then pulling the cap 900 off from the insert 800 along the first longitudinal axis 1102. When the cap 900 has been rotated (including both prior to pulling the cap 900 off from the insert 800 and after pulling the cap 900 off from the insert 800), the insert 800 is prevented from becoming separated from the main body assembly 1100. That is, rotation of the cap 900 relative to the insert 800 results in locking the insert 800 in relation to the main body assembly 1100 so that the insert 800 cannot be removed from engagement with the main body assembly 1100. Moreover, even attempts to actuate the release button 1123 will not allow the insert 800 to be unlocked from the main body assembly 1100.

As the cap 900 is rotated and then pulled (by a user of the fluid coupling system 1200), the projections 1134*a* and 1134*b* (FIG. 56) travel within the slots 932*a* and 932*b* (FIG. 45). The projections 1134*a* and 1134*b* and slots 932*a* and 932*b* are configured to facilitate the desired movements of the cap 900 in relation to the first and second coupling portions 1000/1100, so as to properly remove the cap 900 from the insert 800. As the cap 900 is pulled away from engagement with the insert 800, the slider 1130 will also travel with the cap 900.

When the cap 900 is pulled away from the insert 800 to the extent that the cap reaches its fully disengaged position (i.e., fully disengaged from the insert 800), the cap 900 can be releasably detained using a detent mechanism in that fully disengaged position. That is, the cap 900 can be detained relative to the housing 1110. In some embodiments, audible and/or tactile feedback is provided to indicate that the cap 900 has reached its fully disengaged position at which the cap is detained relative to the housing 1110.

Referring to FIGS. 63-65, after completing the disengagement of the cap 900 from the insert 800 as described above, the depicted fluid coupling system 1200 is then arranged in the configuration as shown. The cap 900 and the slider 1130 have been fully pulled away from engagement with the first coupling portion 1000. Consequently, the slider 1130 will no longer restrict the movement of the shuttle 1120 away from the connection member's first position that is coaxial with the first longitudinal axis 1102. That is, with the slider 1130 located in the position shown, the shuttle 1120 and the insert 800 are free to be slid towards the second position of the shuttle 1120 where the shuttle 1120 is coaxial with the second longitudinal axis 1104. It should be understood that until the shuttle 1120 is located in the second position where the shuttle 1120 is coaxial with the second longitudinal axis 1104, the body valve 1150 is physically restricted from moving from the orientation as shown.

In some embodiments, the shuttle 1120 is releasably detained in one or both of its end-of-travel positions (i.e., (1) positioned coaxial with the longitudinal axis 802 and (2) positioned coaxial with the second longitudinal axis 1104). That is, in some embodiments as the shuttle 1120 is slid into an end-of-travel position, the shuttle 1120 will become releasably latched into a detained relationship with the housing 1110. Audible and/or tactile feedback may be provided when the shuttle 1120 becomes releasably detained in its end-of-travel position(s). In some embodiments, a mechanical unlatching (e.g., by actuating a release mechanism) must occur to move the shuttle 1120 from a detained end-of-travel position. Alternatively, in some embodiments merely physically forcing the shuttle 1120 away from a detained end-of-travel position will forcibly overcome the detention of the shuttle 1120 relative to the housing 1110.

Figure 66:
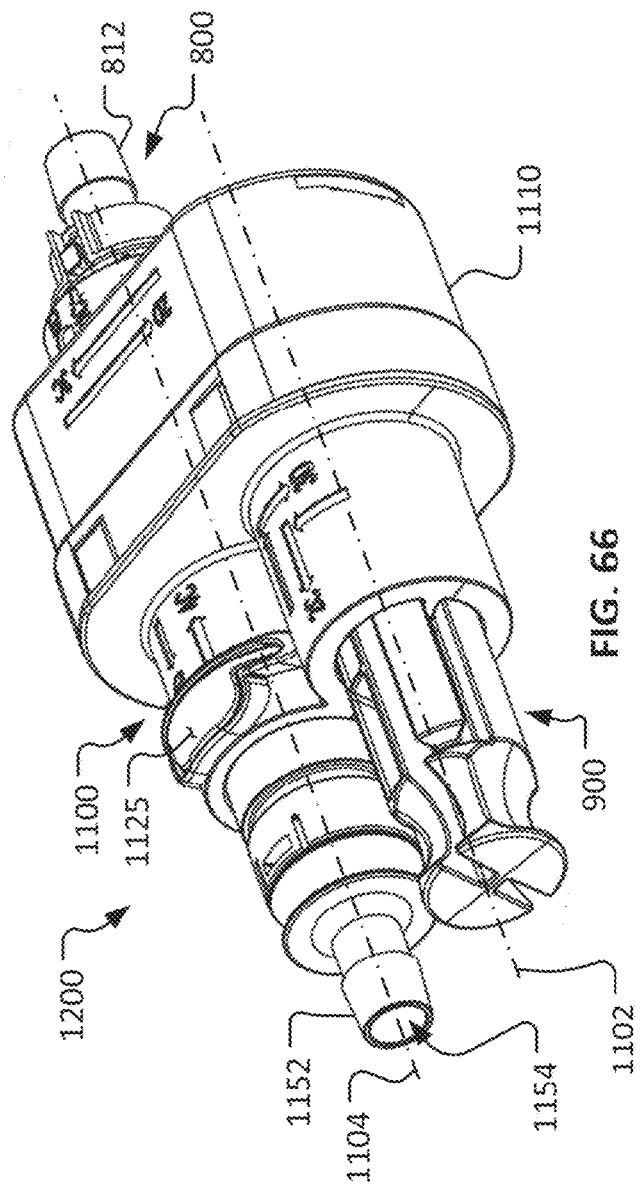
FIG. 66 is a perspective view of the repeatable sterile fluid coupling system of FIG. 57 in a third configuration.
Figure 68:
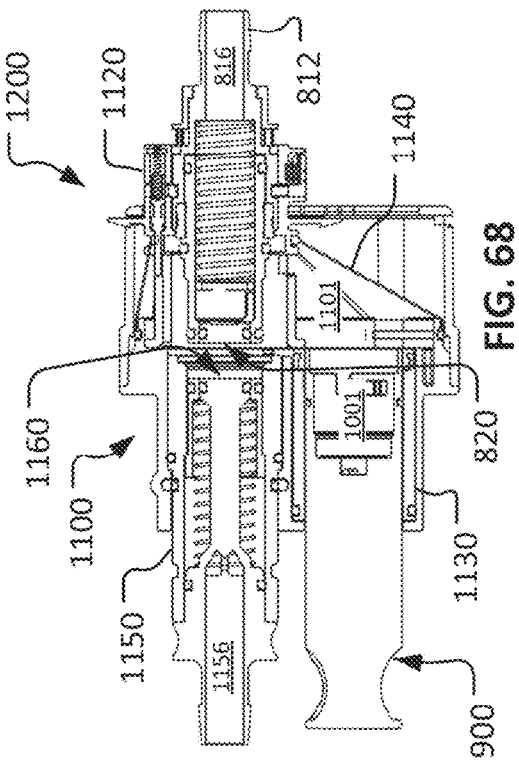
FIG. 68 is a longitudinal cross-sectional side view of the repeatable sterile fluid coupling system as configured in FIG. 66.
Figure 67:
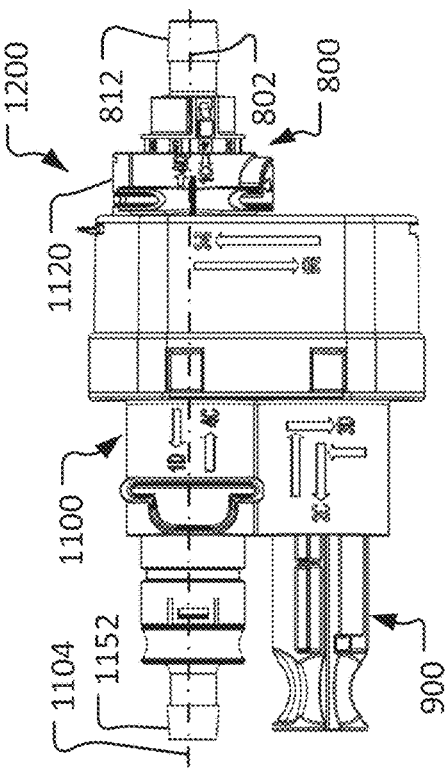
FIG. 67 is a longitudinal side view of the repeatable sterile fluid coupling system as configured in FIG. 66.

Referring to FIGS. 66-68, after the user moves the shuttle 1120 and the insert 800 to the connection member's second position that is coaxial with the second longitudinal axis 1104, the depicted fluid coupling system 1200 is then arranged in the configuration as shown. The sterile regions 1001 and 1101 are now in fluid communication with each other.

As the shuttle 1120 and the insert 800 are moved between the first position that is coaxial with the first longitudinal axis 1102 and the second position that is coaxial with the second longitudinal axis 1104, the flexible member 1140 conforms as needed to facilitate the movement, while maintaining a sterile barrier and/or isolation barrier.

While the shuttle 1120 and the insert 800 are in the second position as shown, the longitudinal axis 802 of the insert 800 is coincident with the second longitudinal axis 1104. In that arrangement, the valve member 820 of the first coupling portion 1000 is in alignment with the valve member 1160 of the main body assembly 1100. Therefore, by moving the body valve 1150 that houses the valve member 1160 toward the valve member 820 of the first coupling portion 1000, the two valve members 820 and 1160 can engage with each other so that a fluid flow pathway is opened. In other words, in some embodiments valve member 820 can be opened by valve member 1160.

Referring to FIGS. 69-71, after the user moves the body valve 1150 toward the valve member 820 of the first coupling portion 1000, the two valve members 820 and 1160 engage with each other to open a fluid flow pathway, and the depicted fluid coupling system 1200 is then arranged in the configuration as shown. Additionally, in some embodiments the body valve 1150 will become releasably latched in relation to the housing 1110 (when the body valve 1150 is fully engaged with the insert 800). To thereafter unlatch the body valve 1150, in some embodiments the user will need to depress a body valve unlatching mechanism 1125 and concurrently pull the body valve 1150 away from the housing 1110. In some embodiments, when the user depresses the body valve unlatching mechanism 1125, the body valve 1150 will spontaneously move away from the housing 1110 (without a need for physically pulling the body valve 1150 away from the housing 1110). The latching of the body valve 1150 in relation to the housing 1110 can be accompanied by audible and/or tactile feedback to indicate that full engagement has been accomplished.

As the two valve members 820 and 1160 engage with each other, the center stem 1162 (FIG. 56) of the valve member 1160 makes face-to-face contact with the valve member 820. In addition, the spring-loaded movable valve sleeve 1164 makes contact with a portion of the valve body 810 that surrounds the valve member 820. Such contact results in compression of spring member 822 and of spring member 1169, and a sterile/isolated fluid flow pathway is opened between the end ports 814 and 1154.

In the depicted embodiment, the user can push the body valve 1150 toward the first coupling portion 1000. As the body valve 1150 is pushed by the user, the spring members 822 and 1169 will become compressed and provide resistance to the movement. The body valve 1150 and the housing 1110 can be configured to allow the body valve 1150 to be releasably locked in relation to the housing 1110 while the spring members 822 and 1169 are compressed. For example, in the depicted embodiment, after pushing the body valve 1150 toward the first coupling portion 1000 along the longitudinal axis 1104 so as to compress the spring members 822 and 1169, the user can then twist the body valve 1150 to lock the body valve 1150 to the housing 1110. In result, the user can release the body valve 1150 and housing 1110 and the sterile fluid flow pathway will remain open between end ports 814 and 1154. In the depicted embodiment, a bayonet-style coupling is used to releasably lock the body valve 1150 to the housing 1110. In some embodiments, other types of mechanisms can be used to releasably lock the body valve 1150 to the housing 1110 such as, but not limited to, a pin/hole, a clip, a latch, a threaded connection, and the like, and combinations thereof.

While in the depicted embodiment the two valve members 820 and 1160 are made to engage with each other by pushing the body valve 1150 toward the first coupling portion 1000, in some embodiments the engagement can be made by pushing the first coupling portion 1000 (or portions thereof) toward the body valve 1150. That is, in some embodiments the body valve 1150 is fixed in relation to the housing 1110, and the first coupling portion 1000 is translatable along axes 802 and 1104 when the first coupling portion 1000 is in the second portion (where the two valve members 820 and 1160 are coaxial).

With the fluid coupling system 1200 arranged in the illustrated configuration, fluids can flow through the fluid coupling system 1200 between the end ports 814 and 1154. The fluid pathway between the end ports 814 and 1154 is a sterile/isolated fluid pathway.

If desired, the fluid coupling system 1200 can be uncoupled by following the reverse of the process described above for coupling the fluid coupling system 1200. For example, the body valve unlatching mechanism 1125 can be actuated and the body valve 1150 can be concurrently pulled away from the housing 1110. Then the shuttle 1120 (with the insert 800 coupled thereto) can be translated to become coaxial with the first longitudinal axis 1102. At that point, the cap 900 can be pushed toward the insert 800 and rotated into engagement with the insert 800. With the cap 900 properly engaged with the insert 800, the release button 1123 can be actuated and the coupling portions 1000 and 1100 can be separated.

As the fluid coupling system 1200 is uncoupled (such that the first coupling portion 1000 is separated from the main body assembly 1100), the sterility/isolation of the first sterile region 1001 and the second sterile region 1101 is maintained. For example, as part of the process for separating the first coupling portion 1000 from the main body assembly 1100, the cap 900 is reinstalled on the insert 800, and the coupling portions 1000 and 1100 are configured as shown in FIGS. 57-59 once again. Then, the release button 1123 can be depressed to unlatch the coupling portions 1000 and 1100 from each other. The release button 1123 can only be actuated effectively if the coupling portion 1000 is properly assembled. Thereafter, if desired, the fluid coupling system 1200 can be recoupled by following the process described above for coupling the fluid coupling system 1200. Once again, a sterile/isolated fluid pathway between the end ports 814 and 1154 will be established. One of skill in the art will recognize that the repeatable, aseptic fluid coupling system 1200 can be connected, disconnected, reconnected, and so on, for multiple cycles. In each case, while the first coupling portion 1000 is connected to the main body assembly 1100 as shown in FIGS. 69-71, a sterile/isolated fluid pathway between the end ports 814 and 1154 exists.

Figure 72:
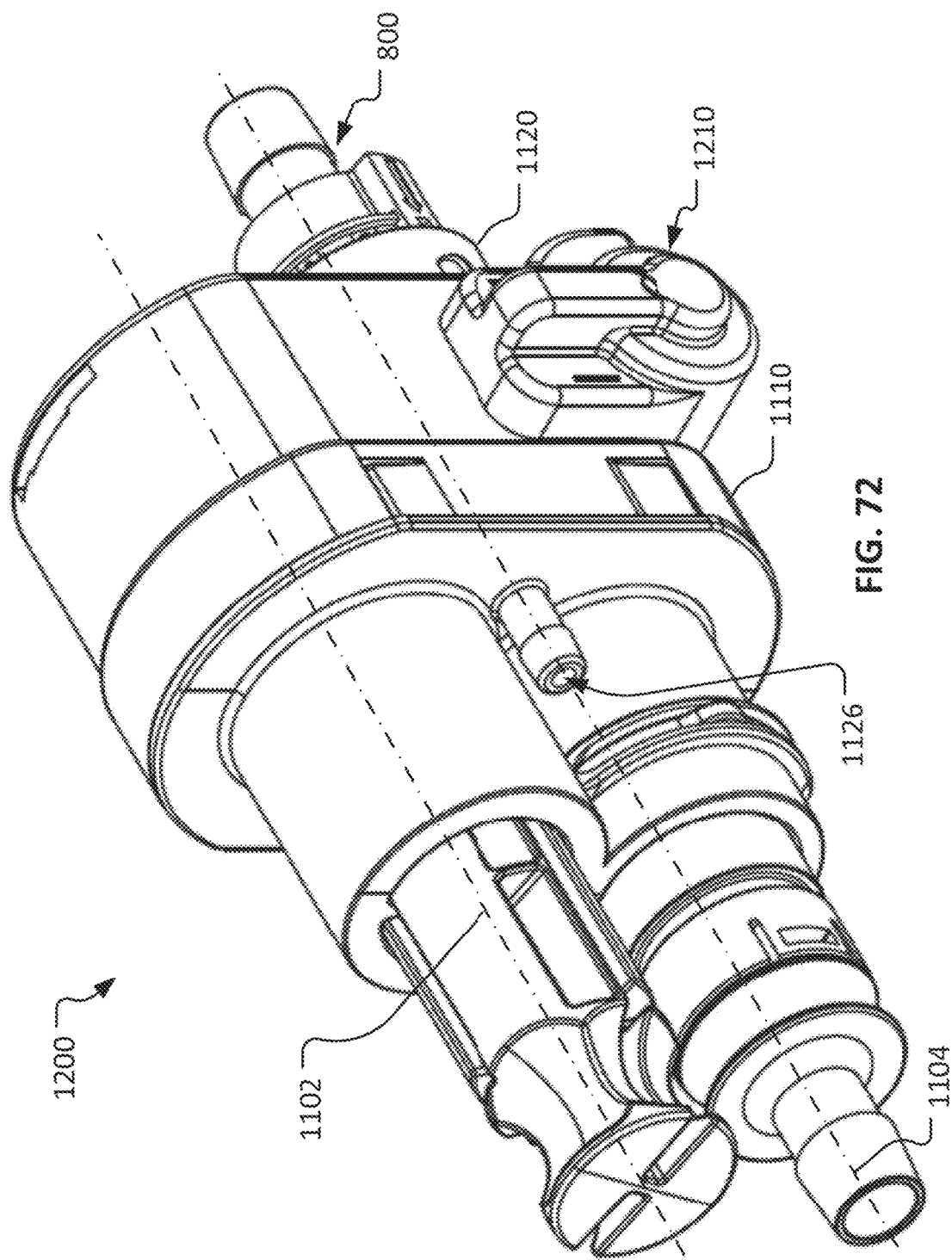
FIG. 72 is a perspective view of a repeatable sterile fluid coupling system that includes a cycle counter mechanism in accordance with some embodiments.

Referring to FIG. 72, in some embodiments a cycle counter 1210 is included in conjunction with the fluid coupling system 1200. The cycle counter 1210 can be used to quantify a number of times that the fluid coupling system 1200 has been operated. Moreover, in some embodiments an upper limit of permissible cycles can be selectively established, and the cycle counter 1210 can lock-out the fluid coupling system 1200 from further operation once the upper limit has been reached. The upper limit of permissible cycles can be any selected integer (e.g., 1, 2, 3, 4, 5, 6, 7, 8, 9, 10, 11, 12, 13, 14, and so on).

For example, in the depicted embodiment, the cycle counter 1210 is coupled to the housing 1110. In some embodiments, the cycle counter 1210 is releasably coupled to the housing 1110. The cycle counter 1210 will be indexed each time the shuttle 1120 is placed into its end-of-travel position where it is coaxial with the second longitudinal axis 1104. A visual indicator (e.g., a numeric indicator or a color indicator) of the number of spent cycles or the number of remaining cycles can be provided by the cycle counter 1210. Hence, the user can be informed of how many times the fluid coupling system 1200 has been used or how many more cycles the fluid coupling system 1200 can be used.

In some embodiments, when the upper limit of cycles have been spent, a mechanism will prevent any further usage of fluid coupling system 1200. For example, in the depicted embodiment the cycle counter 1210 will mechanically interfere with the translation of the shuttle 1120 as it is being slid toward its end-of-travel position where it is coaxial with the second longitudinal axis 1104. In other words, the cycle counter 1210 will not permit the shuttle 1120 to be positioned at its end-of-travel position coaxial with the second longitudinal axis 1104. Therefore, the fluid coupling system 1200 will not be further useable when the upper limit of usage cycles have been spent.

Similarly, in some embodiments the insert 800 can alternatively or additionally include a cycle counter mechanism. Referring again to FIGS. 42-44, an optional cycle counter mechanism 840 is movably coupled to the valve body 810. In the depicted embodiment, the cycle counter mechanism 840 is designed to be manually indexed (rotationally) prior to each use (i.e., prior to coupling the first coupling portion 1000 comprising the insert 800 and the cap 900 to the main body assembly 1100). The cycle counter mechanism 840 can only be rotated in one rotational direction. As with the cycle counter 1210 described above, an upper limit of permissible cycles can be selectively established, and the cycle counter mechanism 840 can lock-out the fluid coupling system 1200 from further operation once the upper limit has been reached. For example, in some embodiments when the upper limit of permissible cycles of the insert 800 has been reached, the cycle counter mechanism 840 can thereafter mechanically prevent proper coupling of the first coupling portion 1000 to the main body assembly 1100. Hence, the fluid coupling system 1200 will not be further useable when the upper limit of usage cycles have been spent.

In some embodiments, the main body assembly 1100 can also include an optional vent 1126. The vent 1126 provides an air-transmissible pathway between the second sterile region 1101 and the regions exterior of the main body assembly 1100. In some embodiments, a filter media or porous element is included within the vent 1126. Such a filter or porous element can serve to inhibit transmission of particles and/or microorganisms, while still allowing transmission of air therethrough. In some embodiments, the filter media or porous element of the vent 1126 allows the transmission of materials that are smaller than about 0.2 µm in size, while inhibiting the transmission of materials that are larger. In some embodiments, the filter media or porous element of the vent 1126 inhibits the transmission of materials that are larger than about 0.1 µm, or about 0.3 µm, or about 0.4 µm, or about 0.5 µm, or larger than 0.5 µm, while allowing the transmission of materials that are smaller.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A fluid coupling device comprising:
   a valve body with a first end portion and a second end portion, the valve body defining a longitudinal axis and a fluid pathway extending along the longitudinal axis between the first and second end portions of the valve body, the fluid pathway terminating at an end port defined by the second end portion of the valve body;
   a valve member disposed within the valve body, the valve member being movable relative to the valve body along the longitudinal axis between: (i) an open position in which the fluid pathway is open through the valve body and (ii) a closed position in which the fluid pathway through the valve body is blocked by the valve member;
   a spring disposed within the valve body and arranged to bias the valve member to the closed position;
   a connection structure coupled to the valve body and configured for releasably mating the fluid coupling device to another fluid coupling device; and
   a cap with a first end portion and a second end portion, the first end portion of the cap defining a bore configured to removably receive the first end portion of the valve body therein,
   wherein the cap defines one or more longitudinally-extending slots along an exterior of the cap, each longitudinally-extending slot defining an open end at the second end portion of the cap, and
   wherein the first end portion of the valve body includes one or more radial projections, and wherein the bore of the cap includes one or more complementary L-shaped slots configured to removably receive the one or more radial projections.

2. The fluid coupling of claim 1, wherein the cap includes a seal member surrounding an outer periphery of the cap.

3. The fluid coupling of claim 1, wherein the first end portion of the cap includes a seal member surrounding an outer periphery of the cap.

4. The fluid coupling of claim 1, wherein the cap includes a vent that inhibits transmission of particles and/or microorganisms therethrough while allowing transmission of air therethrough.

5. The fluid coupling of claim 1, wherein the connection structure is movably coupled to the valve body.

6. The fluid coupling of claim 5, wherein the connection structure includes threads by which the connection structure is configured for releasably mating the fluid coupling device to another fluid coupling device.

7. The fluid coupling of claim 1, wherein the valve body includes at least two seals disposed around an outer periphery of the valve body.

8. The fluid coupling of claim 1, wherein there are at least two seals between the valve body and the cap while the cap is coupled to the valve body.

9. The fluid coupling of claim 1, wherein the fluid pathway is sterile.

10. A fluid coupling device comprising:
    a valve body with a first end portion and a second end portion, the valve body defining a longitudinal axis and a fluid pathway extending along the longitudinal axis between the first and second end portions of the valve body, the fluid pathway terminating at an end port defined by the second end portion of the valve body;
    a valve member disposed within the valve body, the valve member being movable relative to the valve body along the longitudinal axis between: (i) an open position in which the fluid pathway is open through the valve body and (ii) a closed position in which the fluid pathway through the valve body is blocked by the valve member;
    a spring disposed within the valve body and arranged to bias the valve member to the closed position;
    a connection structure coupled to the valve body and configured for releasably mating the fluid coupling device to another fluid coupling device; and
    a cap with a first end portion and a second end portion, the first end portion of the cap defining a bore configured to removably receive the first end portion of the valve body therein,
    wherein the cap defines one or more longitudinally-extending slots along an exterior of the cap, each longitudinally-extending slot defining an open end at the second end portion of the cap, and
    wherein the cap includes a vent that inhibits transmission of particles and/or microorganisms therethrough while allowing transmission of air therethrough.

11. The fluid coupling of claim 10, wherein the first end portion of the valve body includes one or more radial projections, and wherein the bore of the cap includes one or more complementary slots configured to removably receive the one or more radial projections.

12. The fluid coupling of claim 11, wherein the one or more complementary slots are L-shaped.

13. The fluid coupling of claim 10, wherein the cap includes a seal member surrounding an outer periphery of the cap.

14. The fluid coupling of claim 10, wherein the first end portion of the cap includes a seal member surrounding an outer periphery of the cap.

15. The fluid coupling of claim 10, wherein the connection structure is movably coupled to the valve body.

16. The fluid coupling of claim 15, wherein the connection structure includes threads by which the connection structure is configured for releasably mating the fluid coupling device to another fluid coupling device.

17. The fluid coupling of claim 10, wherein the valve body includes at least two seals disposed around an outer periphery of the valve body.

18. The fluid coupling of claim 10, wherein there are at least two seals between the valve body and the cap while the cap is coupled to the valve body.

19. The fluid coupling of claim 10, wherein the fluid pathway is sterile.

20. The fluid coupling of claim 10, wherein the first end portion of the valve body includes one or more radial projections.

* * * * *